US008507690B2

(12) United States Patent
Matsukawa et al.

(10) Patent No.: US 8,507,690 B2
(45) Date of Patent: Aug. 13, 2013

(54) THIAZOLE DERIVATIVE AND USE THEREOF AS VAP-1 INHIBITOR

(75) Inventors: Tatsuya Matsukawa, Tokyo (JP); Kazuhiro Masuzaki, Tokyo (JP); Yosuke Kawai, Tokyo (JP); Akiko Kawasaki, Tokyo (JP); Akiko Akasaka, Tokyo (JP); Makoto Takewaki, Tokyo (JP)

(73) Assignee: R-Tech Ueno, Ltd., Tokyo (JP)

( * ) Notice: Subject to any disclaimer, the term of this patent is extended or adjusted under 35 U.S.C. 154(b) by 28 days.

(21) Appl. No.: 12/864,773

(22) PCT Filed: Jan. 30, 2009

(86) PCT No.: PCT/JP2009/052015
§ 371 (c)(1),
(2), (4) Date: Sep. 29, 2010

(87) PCT Pub. No.: WO2009/096609
PCT Pub. Date: Aug. 6, 2009

(65) Prior Publication Data
US 2011/0015240 A1  Jan. 20, 2011

(30) Foreign Application Priority Data

Jan. 31, 2008 (JP) ................................ 2008-021588

(51) Int. Cl.
*C07D 277/38* (2006.01)
*A61K 31/427* (2006.01)
*A61K 31/426* (2006.01)

(52) U.S. Cl.
USPC ............ 548/192; 548/195; 514/369; 514/371

(58) Field of Classification Search
None
See application file for complete search history.

(56) References Cited

U.S. PATENT DOCUMENTS

| 4,888,283 | A | 12/1989 | Bertini et al. | |
|---|---|---|---|---|
| 7,125,901 | B2 * | 10/2006 | Inoue et al. | 514/371 |
| 2002/0173521 | A1 | 11/2002 | Smith et al. | |
| 2010/0190834 | A1 | 7/2010 | Mashima et al. | |
| 2010/0210697 | A1 | 8/2010 | Mashima et al. | |

FOREIGN PATENT DOCUMENTS

| EP | 0 210 140 A2 | 1/1987 |
|---|---|---|
| EP | 1 338 280 A1 | 8/2003 |
| JP | 61-239891 A | 10/1986 |
| WO | WO 93/23023 A1 | 11/1993 |
| WO | WO 02/02090 A2 | 1/2002 |
| WO | WO 02/02541 A2 | 1/2002 |
| WO | WO 02/38152 A1 | 5/2002 |
| WO | WO 02/38153 A1 | 5/2002 |
| WO | WO 2004/067521 A1 | 8/2004 |
| WO | WO 2004/087138 A1 | 10/2004 |
| WO | WO 2005/089755 A1 | 9/2005 |
| WO | WO 2006/011631 A2 | 2/2006 |
| WO | WO 2006/028269 A2 | 3/2006 |
| WO | WO 2008/066145 A1 | 6/2008 |
| WO | WO 2009/001857 A1 | 12/2008 |
| WO | WO 2009/051223 A1 | 4/2009 |

OTHER PUBLICATIONS

Michel Goedert et al., "A Century of Alzheimer's Disease" Science vol. 314. No. 5800, pp. 777-781 (Nov. 3, 2006).*
Boomsma et al., *Diabetologia*, 42: 233-237 (1999).
Garpenstrand et al., *Diabetic Medicine*, 16: 514-521 (1999).
European Patent Office, International Search Report in International Patent Application No. PCT/JP2009/052015 (Jul. 7, 2009).

* cited by examiner

*Primary Examiner* — Nyeemah A Grazier
(74) *Attorney, Agent, or Firm* — Leydig, Voit & Mayer, Ltd.

(57) ABSTRACT

The invention provides a thiazole derivative useful as a VAP-1 inhibitor, as well as a pharmaceutical agent for the prophylaxis or treatment of VAP-1 associated diseases and the like, a method of inhibiting VAP-1 in a subject, and a method for the prophylaxis or treatment of VAP-1 associated disease in a subject. The thiazole derivative is a compound represented by the formula (I): $R^1$—NH—X—Y—Z wherein each symbol is as defined in the specification, or a pharmaceutically acceptable salt thereof.

35 Claims, No Drawings

THIAZOLE DERIVATIVE AND USE THEREOF AS VAP-1 INHIBITOR

TECHNICAL FIELD OF THE INVENTION

The present invention relates to a novel thiazole derivative (compounds represented by the below-mentioned formula (I) (hereinafter to be also referred to as compound (I)) and a pharmaceutically acceptable salt thereof, hereinafter to be sometimes collectively referred to as the compound of the present invention). In addition, the present invention relates to a vascular adhesion protein-1 inhibitor, a pharmaceutical agent for the prophylaxis or treatment of vascular adhesion protein-1 associated disease and the like, which comprise the compound of the present invention as an active ingredient.

BACKGROUND OF THE INVENTION

The vascular adhesion protein-1 (hereinafter to be abbreviated as VAP-1) is amine oxidase (semicarbazide sensitive amine oxidase, SSAO) abundantly existing in human plasma, which shows a remarkably increased expression in vascular endothelium and vascular smooth muscle in the inflammatory lesion. Although the physiological role of VAP-1 has not been elucidated until recently, VAP-1 gene was cloned in 1998, and VAP-1 was reported to be a membrane protein which, as an adhesion molecule, controls rolling and migration of lymphocytes and NK cells under the expression control of inflammatory cytokine. Although amine to be the substrate is unknown, it is considered to be methylamine produced in any part in the living body. It is also known that hydrogen peroxide and aldehyde produced due to the intramolecular amine oxidase activity are important factors for adhesion activity.

Recent reports have demonstrated that VAP-1 enzyme activity in plasma increases both in type I and type II diabetic patients, and the increase is particularly noticeable in diabetic patients affected with retinopathy complications (Diabetologia, 42 (1999) 233-237 (non-patent document 1), Diabetes Medicine, 16 (1999) 514-521 (non-patent document 2)).

Furthermore, VAP-1 has also been reported to relate to the following diseases (1)-(6): (1) cirrhosis, essential stabilized hypertension, diabetes, arteriosclerosis (see JP-A-61-239891 (patent document 1) and U.S. Pat. No. 4,888,283 (patent document 2)); (2) endothelial injury (in diabetes, arteriosclerosis and hypertension), cardiovascular disease relating to diabetes or uremia, pain relating to gout and arthritis, retinopathy (in diabetic patients) (see WO 1993/23023 (patent document 3)); (3) inflammatory disease or symptom (of binding tissue) (rheumatoid arthritis, ankylosing spondylitis, psoriatic arthritis and osteoarthritis or degenerative joint disease, Reiter's syndrome, Sjogren's syndrome, Behcet's syndrome, relapsing polychondritis, systemic lupus erythematosus, discoid lupus erythematodes, systemic sclerosis, eosinophilic fasciitis, polymyositis, dermatomyositis, polymyalgia rheumatica, vasculitis, temporal arthritis, polyarteritis nodosa, Wegener's granulomatosis, mixed connective tissue diseases and juvenile rheumatoid arthritis); inflammatory disease or symptom of gastrointestinal tract [Crohn's disease, ulcerative colitis, irritable bowel syndrome (spastic colon), fibrosis of liver, inflammation (stomatitis) of oral mucous membrane and recurrent aphthous stomatitis]; inflammatory disease or symptom of central nervous system (multiple sclerosis, Alzheimer's disease, and ischemia-reperfusion injury relating to ischemic stroke); pulmonary inflammatory disease or symptom (asthma, adult respiratory distress syndrome, chronic obliterative pulmonary diseases); (chronic) inflammatory disease or symptom of the skin (psoriasis, allergic lesion, lichen planus, pityriasis rosea, contact dermatitis, atopic dermatitis, pityriasis rubra pilaris); disease relating to carbohydrate metabolism (diabetes and complications derived from diabetes) including disease of microvessel and large vessel (arteriosclerosis, vascular retinopathy, retinopathy, nephropathy, nephrotic syndrome and neuropathy (multiple neuropathy, mononeuropathy and autonomic neuropathy), foot ulcer, articular problem and increase in infection risk); disease relating to abnormality in the differentiation or function of adipocyte or function of smooth muscle cell (arteriosclerosis and obesity); vascular disease [atherosclerosis, nonatherosclerotic disease, ischemic cardiac diseases including myocardial infarction and peripheral arterial obstruction, Raynaud's disease and Raynaud's phenomenon, thromboangiitis obliterans (Buerger's disease)]; chronic arthritis; inflammatory bowel disease; skin disease (see WO 2002/02090 (patent document 4), WO 2002/02541 (patent document 5) and US 2002/0173521 A (patent document 6)); (4) diabetes (see WO 2002/38152 (patent document 7)); (5) SSAO-mediated complications [diabetes (insulin-dependent diabetes (IDDM) and noninsulin-dependent diabetes (NIDDM)) and vascular complications (heart attack, angina pectoris, apoplexy, adamption, blindness and renal failure)] (see WO 2002/38153 (patent document 8)); (6) vascular hyperpermeable disease [aged macular degeneration, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, ocular inflammatory disease caused by bacterial or viral infection, and by ophthalmic operation, ocular inflammatory disease caused by physical injury to the eye, symptom caused by ocular inflammatory disease including itching, flare, edema and ulcer, erythema, erythema exsudativum multiforme, erythema nodosum, erythema annulare, scleredema, dermatitis, angioneurotic edema, laryngeal edema, glottic edema, subglottic laryngitis, bronchitis, rhinitis, pharyngitis, sinusitis and laryngitis or otitis media] (see WO 2004/087138 (patent document 9)); and the like.

WO 2004/067521 (patent document 10), WO 2004/087138% (patent document 9), WO 2006/011631 (patent document 11) and WO 2006/028269 (patent document 12) describe thiazole derivatives having specific structures and that they can be used for the prophylaxis or treatment of VAP-1 associated disease such as macular edema, vascular hyperpermeable disease and the like.

The thiazole derivatives having specific structures, which are described in WO 2004/067521 (patent document 10), WO 2004/087138 (patent document 9) and WO 2006/028269 (patent document 12), also conceptually encompass a compound having a hydrazino group or a hydrazinocarbonyl group at the molecular terminal. However, they do not disclose a novel compound having the specific functional group of the present invention (carbazic acid ester group, carbazic acid thioester group or semicarbazide group).

While WO 2008/066145 (patent document 13) describes a thiazole derivative having a particular structure, it does not disclose the novel compound of the present invention.

patent document 1: JP-A-61-239891
patent document 2: U.S. Pat. No. 4,888,283
patent document 3: WO 1993/23023 patent document 4: WO 2002/02090
patent document 5: WO 2002/02541
patent document 6: US 2002/0173521 A
patent document 7: WO 2002/38152
patent document 8: WO 2002/38153
patent document 9: WO 2004/087138
patent document 10: WO 2004/067521
patent document 11: WO 2006/011631
patent document 12: WO 2006/028269
patent document 13: WO 2008/066145
non-patent document 1: Diabetologia, 42 (1999) 233-237
non-patent document 2: Diabetes Medicine, 16 (1999) 514-521

DISCLOSURE OF THE INVENTION

Problems to be Solved by the Invention

The present invention aims to provide a novel thiazole derivative useful as a VAP-1 inhibitor, a pharmaceutical agent for the prophylaxis or treatment of VAP-1 associated diseases and the like.

Means of Solving the Problems

As a result of intensive studies, the present inventors have found that a thiazole derivative having a specific functional group (carbazic acid ester group, carbazic acid thioester group or semicarbazide group) at the molecular terminal has superior VAP-1 inhibitory action, is superior in enzyme selectivity and can eliminate feared side effects, and conducted further studies, which resulted in the completion of the present invention.

Accordingly, the present invention is as follows.

(1) A compound represented by the formula (I):

R¹—NH—X—Y—Z    (I)

wherein
R¹ is acyl;
X is a divalent residue derived from optionally substituted thiazole;
Y is the formula (III):

J-L-M    (III)

wherein J is a bond, lower alkylene, lower alkenylene, lower alkynylene, —(CH$_2$)$_n$—O—, —(CH$_2$)$_n$—NH—, —(CH$_2$)$_n$—CO— or —(CH$_2$)$_n$—SO$_2$— (wherein n is an integer of 0 to 6);
L is a bond, —O—, —NH—, —CO— or —SO$_2$—;
M is a bond, lower alkylene, lower alkenylene or lower alkynylene, provided that when J is —(CH$_2$)$_n$—O—, L is not —O—, —NH— and —SO$_2$—, when J is —(CH$_2$)$_n$—NH—, L is not —O— and —NH—, when J is —(CH$_2$)$_n$—CO—, L is not —CO—, when J is —(CH$_2$)$_n$—SO$_2$—, L is not —O— and —SO$_2$— (wherein n is as defined above),
Z is the formula (II):

A-B-D-E    (II)

wherein A is a divalent residue derived from optionally substituted benzene, or a divalent residue derived from optionally substituted thiophene;
B is —(CH$_2$)$_l$—NR$^2$—CO— wherein R$^2$ is hydrogen, lower alkyl or acyl, l is an integer of 1 to 6, —(CH$_2$)$_m$—O—CO— or —(CH$_2$)$_m$—S—CO— (wherein m is an integer of 0 to 6);
D is —NR$^3$— wherein R$^3$ is hydrogen, lower alkyl, alkoxycarbonyl or acyl; and
E is optionally substituted amino; or a pharmaceutically acceptable salt thereof.

(2) The compound of the above-mentioned (1), wherein the compound represented by the aforementioned formula (I) is
4-{2-[2-(acetylamino)-1,3-thiazol-4-yl]ethyl}phenyl hydrazinecarboxylate,
4-{2-[2-(acetylamino)-1,3-thiazol-4-yl]ethyl}benzyl hydrazinecarboxylate,
2-(4-{2-[2-(acetylamino)-1,3-thiazol-4-yl]ethyl}phenyl) ethyl hydrazinecarboxylate,
4-{2-[2-(acetylamino)-1,3-thiazol-4-yl]ethyl}-2-fluorobenzyl hydrazinecarboxylate,
4-{2-[2-(acetylamino)-1,3-thiazol-4-yl]ethyl}-3-fluorobenzyl hydrazinecarboxylate,
4-{2-[2-(acetylamino)-1,3-thiazol-4-yl]ethyl}-2,3-difluorobenzyl hydrazinecarboxylate,
2-(4-{[2-(acetylamino)-1,3-thiazol-4-yl]methoxy}phenyl) ethyl hydrazinecarboxylate,
4-{2-[(hydrazinocarbonyl)oxy]ethyl}phenyl 2-(acetylamino)-1,3-thiazole-4-carboxylate,
2-[4-({[2-(acetylamino)-1,3-thiazol-4-yl]carbonyl}amino) phenyl]ethyl hydrazinecarboxylate,
3-{2-[2-(acetylamino)-1,3-thiazol-4-yl]ethyl}phenyl hydrazinecarboxylate,
3-{2-[2-(acetylamino)-1,3-thiazol-4-yl]ethyl}benzyl hydrazinecarboxylate,
2-(3-{2-[2-(acetylamino)-1,3-thiazol-4-yl]ethyl}phenyl) ethyl hydrazinecarboxylate,
{5-[2-(2-acetylamino-1,3-thiazol-4-yl)ethyl]thiophen-2-yl}methyl hydrazinecarboxylate,
2-(5-{2-[2-(acetylamino)-1,3-thiazol-4-yl]ethyl}thiophen-2-yl)ethyl hydrazinecarboxylate,
3-(4-{2-[2-(acetylamino)-1,3-thiazol-4-yl]ethyl}thiophen-2-yl)propyl hydrazinecarboxylate,
3-(5-{2-[2-(acetylamino)-1,3-thiazol-4-yl]ethyl}thiophen-3-yl)propyl hydrazinecarboxylate,
3-(5-{2-[2-(acetylamino)-1,3-thiazol-4-yl]ethyl}-3-methylthiophen-2-yl)propyl hydrazinecarboxylate,
N-(4-{2-[2-(acetylamino)-1,3-thiazol-4-yl]ethyl}benzyl)hydrazinecarboxamide,
N-[2-(4-{2-[2-(acetylamino)-1,3-thiazol-4-yl]ethyl}phenyl) ethyl]hydrazinecarboxamide,
N-(4-{2-[2-(acetylamino)-1,3-thiazol-4-yl]ethyl}-2-fluorobenzyl)hydrazinecarboxamide,
N-(4-{2-[2-(acetylamino)-1,3-thiazol-4-yl]ethyl}-3-fluorobenzyl)hydrazinecarboxamide,
N-(4-{2-[2-(acetylamino)-1,3-thiazol-4-yl]ethyl}-2,3-difluorobenzyl)hydrazinecarboxamide,
N-[4-({[2-(acetylamino)-1,3-thiazol-4-yl]methyl}amino) benzyl]hydrazinecarboxamide,
2-(acetylamino)-N-(4-{[(hydrazinocarbonyl)amino] methyl}phenyl)-1,3-thiazole-4-carboxamide,
N-[2-(4-{[2-(acetylamino)-1,3-thiazol-4-yl] methoxy}phenyl)ethyl]hydrazinecarboxamide,
4-{2-[(hydrazinocarbonyl)amino]ethyl}phenyl 2-(acetylamino)-1,3-thiazole-4-carboxylate,
N-(3-{2-[2-(acetylamino)-1,3-thiazol-4-yl]ethyl}benzyl)hydrazinecarboxamide,
N-[2-(3-{2-[2-(acetylamino)-1,3-thiazol-4-yl]ethyl}phenyl) ethyl]hydrazinecarboxamide,
N-[2-(5-{2-[2-(acetylamino)-1,3-thiazol-4-yl] ethyl}thiophen-2-yl)methyl]hydrazinecarboxamide,
N-[2-(5-{2-[2-(acetylamino)-1,3-thiazol-4-yl] ethyl}thiophen-2-yl)ethyl]hydrazinecarboxamide,
N-[3-(4-{2-[2-(acetylamino)-1,3-thiazol-4-yl] ethyl}thiophen-2-yl)propyl]hydrazinecarboxamide, N-[3-(5-{2-[2-(acetylamino)-1,3-thiazol-4-yl] ethyl}thiophen-3-yl)propyl]hydrazinecarboxamide, N-[3-(5-{2-[2-(acetylamino)-1,3-thiazol-4-yl]ethyl}-3-methylthiophen-2-yl)propyl]hydrazinecarboxamide, S-(4-{2-[2-(acetylamino)-1,3-thiazol-4-yl]ethyl}benzyl) hydrazinecarbothioate, S-[2-(4-{2-[2-(acetylamino)-1,3-thiazol-4-yl]ethyl}phenyl) ethyl]hydrazinecarbothioate, or S-[(5-{2-[2-(acetylamino)-1,3-thiazol-4-yl]ethyl}thiophen-2-yl)methyl]hydrazinecarbothioate, or a pharmaceutically acceptable salt thereof.

(3) The compound of the above-mentioned (1), wherein the compound represented by the aforementioned formula (I) is 4-{2-[2-(acetylamino)-1,3-thiazol-4-yl]ethyl}phenyl hydrazinecarboxylate, 4-{2-[2-(acetylamino)-1,3-thiazol-4-yl]ethyl}benzyl hydrazinecarboxylate or N-(4-{2-[2-(acetylamino)-1,3-thiazol-4-yl]ethyl}benzyl)hydrazinecarboxamide, or a pharmaceutically acceptable salt thereof.

(4) The compound of any one of the above-mentioned (1) to (3), which is used as a pharmaceutical agent, or a pharmaceutically acceptable salt thereof.

(5) A pharmaceutical composition comprising the compound of any one of the above-mentioned (1) to (3) or a pharmaceutically acceptable salt thereof as an active ingredient.

(6) A VAP-1 inhibitor comprising the compound of any one of the above-mentioned (1) to (3) or a pharmaceutically acceptable salt thereof as an active ingredient.

(7) A pharmaceutical agent for the prophylaxis or treatment of VAP-1 associated disease, which comprises the compound of any one of the above-mentioned (1) to (3) or a pharmaceutically acceptable salt thereof as an active ingredient.

(8) The pharmaceutical agent of the above-mentioned (7), wherein the aforementioned VAP-1 associated disease is macular edema (diabetic and nondiabetic macular edema), aged macular degeneration, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, ocular inflammatory disease caused by bacterial or viral infection, and by ophthalmic operation, ocular inflammatory disease caused by physical injury to the eye, symptom caused by ocular inflammatory disease including itching, flare, edema and ulcer, erythema, erythema exsudativum multiforme, erythema nodosum, erythema annulare, scleredema, dermatitis (psoriasis, allergic lesion, lichen planus, pityriasis rosea, contact dermatitis, atopic dermatitis, pityriasis rubra pilaris), angioneurotic edema, laryngeal edema, glottic edema, subglottic laryngitis, bronchitis, rhinitis, pharyngitis, sinusitis and laryngitis or otitis media, cirrhosis, essential stabilized hypertension, diabetes, arteriosclerosis, endothelial injury (in diabetes, arteriosclerosis and hypertension), cardiovascular disease relating to diabetes or uremia, pain relating to gout and arthritis, inflammatory disease or symptom of binding tissue (rheumatoid arthritis, ankylosing spondylitis, psoriatic arthritis and osteoarthritis or degenerative joint disease, Reiter's syndrome, Sjogren's syndrome, Behcet's syndrome, relapsing polychondritis, systemic lupus erythematosus, discoid lupus erythematodes, systemic sclerosis, eosinophilic fasciitis, polymyositis, dermatomyositis, polymyalgia rheumatica, vasculitis, temporal arthritis, polyarteritis nodosa, Wegener's granulomatosis, mixed connective tissue diseases and juvenile rheumatoid arthritis), inflammatory disease or symptom of gastrointestinal tract [Crohn's disease, ulcerative colitis, irritable bowel syndrome (spastic colon), fibrosis of the liver, inflammation of the oral mucous membrane (stomatitis and recurrent aphthous stomatitis)], inflammatory disease or symptom of central nervous system (multiple sclerosis, Alzheimer's disease, and ischemia-reperfusion injury relating to ischemic stroke), pulmonary inflammatory disease or symptom (asthma, adult respiratory distress syndrome, chronic obliterative pulmonary diseases), disease relating to carbohydrate metabolism (diabetes and complications derived from diabetes (diabetic neuropathy, diabetic nephropathy)) including disease of microvessel and large vessel (arteriosclerosis, retinopathy, nephropathy, nephrotic syndrome and neuropathy (multiple neuropathy, mononeuropathy and autonomic neuropathy), foot ulcer, articular problem and increase in infection risk), disease relating to abnormality in the differentiation or function of adipocyte or function of smooth muscle cell (arteriosclerosis and obesity), vascular disease [atheromatous atherosclerosis, nonatheromatous atherosclerotic disease, ischemic cardiac diseases including myocardial infarction and peripheral arterial obstruction, Raynaud's disease and Raynaud's phenomenon, thromboangiitis obliterans (Buerger's disease)], chronic arthritis, inflammatory bowel disease, or SSAO-mediated complications [diabetes (insulin-dependent diabetes (IDDM) and noninsulin-dependent diabetes (NIDDM)) and vascular complications (heart attack, angina pectoris, apoplexy, amputation, blindness and renal failure)], ophthalmic disease associated with hypoxia or ischemia [retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency] or cataract.

(9) Use of the compound of any one of the above-mentioned (1) to (3), or a pharmaceutically acceptable salt thereof, for the production of a pharmaceutical agent as a VAP-1 inhibitor.

(10) Use of the compound of any one of the above-mentioned (1) to (3), or a pharmaceutically acceptable salt thereof, for the production of a pharmaceutical agent for the prophylaxis or treatment of a VAP-1 associated disease.

(11) Use of the above-mentioned (10), wherein the aforementioned VAP-1 associated disease is macular edema (diabetic and nondiabetic macular edema), aged macular degeneration, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal, pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, ocular inflammatory disease caused by bacterial or viral infection, and by ophthalmic operation, ocular inflammatory disease caused by physical injury to the eye, symptom caused by ocular inflammatory disease including itching, flare, edema and ulcer, erythema, erythema exsudativum multiforme, erythema nodosum, erythema annulare, scleredema, dermatitis (psoriasis, allergic lesion, lichen planus, pityriasis rosea, contact dermatitis, atopic dermatitis, pityriasis rubra pilaris), angioneurotic edema, laryngeal edema, glottic edema, subglottic laryngitis, bronchitis, rhinitis, pharyngitis, sinusitis and laryngitis or otitis media, cirrhosis, essential stabilized hypertension, diabetes, arteriosclerosis, endothelial injury (in diabetes, arteriosclerosis and hypertension), cardiovascular disease relating to diabetes or uremia, pain relating to gout and arthritis, inflammatory disease or symptom of binding tissue (rheumatoid arthritis, ankylosing spondylitis, psoriatic arthritis and osteoarthritis or degenerative joint disease, Reiter's syndrome, Sjogren's syndrome, Behcet's syndrome, relapsing polychondritis, systemic lupus erythematosus, discoid lupus erythematodes, systemic sclerosis, eosinophilic fasciitis, polymyositis, dermatomyositis, polymyalgia rheumatica, vasculitis, temporal arthritis, polyarteritis nodosa, Wegener's granulomatosis, mixed connective tissue diseases and juvenile rheumatoid arthritis), inflammatory disease or symptom of gastrointestinal tract [Crohn's disease, ulcerative colitis, irritable bowel syndrome (spastic colon), fibrosis of the liver, inflammation of the oral mucous membrane (stomatitis and recurrent aphthous stomatitis)], inflammatory disease or symptom of central nervous system (multiple sclerosis, Alzheimer's disease, and ischemia-reperfusion injury relating to ischemic stroke), pulmonary inflammatory disease or symptom (asthma, adult respiratory distress syndrome, chronic obliterative pulmonary diseases), disease relating to carbohydrate metabolism (diabetes and complications derived from diabetes (diabetic neuropathy, diabetic nephropathy)) including disease of microvessel and large vessel (arteriosclerosis, retinopathy, nephropathy, nephrotic syndrome and neuropathy (multiple neuropathy, mononeuropathy and autonomic neuropathy), foot ulcer, articular problem and increase in infection risk), disease relating to abnormality in the differentiation or function of adipocyte or function of smooth muscle cell (arteriosclerosis and obesity), vascular disease [atheromatous atherosclerosis, nonatheromatous atherosclerotic disease, ischemic cardiac diseases including myocardial infarction and peripheral arterial obstruction, Raynaud's disease and Raynaud's phenomenon, thromboangiitis obliterans (Buerger's disease)], chronic arthritis, inflammatory bowel disease, or SSAO-mediated complications [diabetes (insulin-dependent diabetes (IDDM) and noninsulin-dependent diabetes (NIDDM)) and vascular complications (heart attack, angina pectoris, apoplexy, amputation, blindness and renal failure)], ophthalmic disease associated with hypoxia or ischemia [retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency] or cataract.

(12) A method of inhibiting VAP-1 in a subject, which comprises administering an effective amount of the compound of any one of the above-mentioned (1) to (3) or a pharmaceutically acceptable salt thereof to the subject.

(13) A method for the prophylaxis or treatment of VAP-1 associated disease in a subject, which comprises administering an effective amount of the compound of any one of the above-mentioned (1) to (3) or a pharmaceutically acceptable salt thereof to the subject.

(14) The method of the above-mentioned (13), wherein the aforementioned VAP-1 associated disease is macular edema (diabetic and nondiabetic macular edema), aged macular degeneration, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, ocular inflammatory disease caused by bacterial or viral infection, and by ophthalmic operation, ocular inflammatory disease caused by physical injury to the eye, symptom caused by ocular inflammatory disease including itching, flare, edema and ulcer, erythema, erythema exsudativum multiforme, erythema nodosum, erythema annulare, scleredema, dermatitis (psoriasis, allergic lesion, lichen planus, pityriasis rosea, contact dermatitis, atopic dermatitis, pityriasis rubra pilaris), angioneurotic edema, laryngeal edema, glottic edema, subglottic laryngitis, bronchitis, rhinitis, pharyngitis, sinusitis and laryngitis or otitis media, cirrhosis, essential stabilized hypertension, diabetes, arteriosclerosis, endothelial injury (in diabetes, arteriosclerosis and hypertension), cardiovascular disease relating to diabetes or uremia, pain relating to gout and arthritis, inflammatory disease or symptom of binding tissue (rheumatoid arthritis, ankylosing spondylitis, psoriatic arthritis and osteoarthritis or degenerative joint disease, Reiter's syndrome, Sjogren's syndrome, Behcet's syndrome, relapsing polychondritis, systemic lupus erythematosus, discoid lupus erythematodes, systemic sclerosis, eosinophilic fasciitis, polymyositis, dermatomyositis, polymyalgia rheumatica, vasculitis, temporal arthritis, polyarteritis nodosa, Wegener's granulomatosis, mixed connective tissue diseases and juvenile rheumatoid arthritis), inflammatory disease or symptom of gastrointestinal tract [Crohn's disease, ulcerative colitis, irritable bowel syndrome (spastic colon), fibrosis of the liver, inflammation of the oral mucous membrane (stomatitis and recurrent aphthous stomatitis)], inflammatory disease or symptom of central nervous system (multiple sclerosis, Alzheimer's disease, and ischemia-reperfusion injury relating to ischemic stroke), pulmonary inflammatory disease or symptom (asthma, adult respiratory distress syndrome, chronic obliterative pulmonary diseases), disease relating to carbohydrate metabolism (diabetes and complications derived from diabetes (diabetic neuropathy, diabetic nephropathy)) including disease of microvessel and large vessel (arteriosclerosis, retinopathy, nephropathy, nephrotic syndrome and neuropathy (multiple neuropathy, mononeuropathy and autonomic neuropathy), foot ulcer, articular problem and increase in infection risk), disease relating to abnormality in the differentiation or function of adipocyte or function of smooth muscle cell (arteriosclerosis and obesity), vascular disease [atheromatous atherosclerosis, nonatheromatous atherosclerotic disease, ischemic cardiac diseases including myocardial infarction and peripheral arterial obstruction, Raynaud's disease and Raynaud's phenomenon, thromboangiitis obliterans (Buerger's disease)], chronic arthritis, inflammatory bowel disease, or SSAO-mediated complications [diabetes (insulin-dependent diabetes (IDDM) and noninsulin-dependent diabetes (NIDDM)) and vascular complications (heart attack, angina pectoris, apoplexy, amputation, blindness and renal failure)], ophthalmic disease associated with hypoxia or ischemia [retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency] or cataract.

Effect of the Invention

The compound of the present invention has superior VAP-1 inhibitory activity and superior enzyme selectivity, and therefore, can remove side effects and the like which are undesirable as a pharmaceutical product. Therefore, the compound is useful as a VAP-1 inhibitor, a pharmaceutical agent for the prophylaxis or treatment of a VAP-1 associated disease and the like.

BEST MODE FOR CARRYING OUT THE INVENTION

The terms used for the present invention in the above- and below-mentioned descriptions of the present specification are explained in detail in the following.

The term "lower" is used to mean a group having a carbon number of 1 to 6, preferably 1 to 4, unless otherwise specified.

Examples of the "lower alkyl" include a straight chain or branched chain alkyl having a carbon number of 1 to 6 (e.g., methyl, ethyl, propyl, isopropyl, butyl, isobutyl, sec-butyl, tert-butyl, pentyl, tert-pentyl and hexyl) and the like. Among these, $C_1$-$C_4$ alkyl is more preferable.

Examples of the "lower alkylene" include a straight chain or branched chain alkylene having a carbon number of 1 to 6 (e.g., methylene, ethylene, trimethylene, propylene, ethylidene and propylidene) and the like. Among these, $C_1$-$C_4$ alkylene is more preferable.

Examples of the "lower alkenylene" include a straight chain or branched chain alkenylene having a carbon number of 2 to 6 (e.g., vinylene, 1-propenylene, 1-methyl-1-propenylene, 2-methyl-1-propenylene, 2-propenylene, 2-butenylene, 1-butenylene, 3-butenylene, 2-pentenylene, 1-pentenylene, 3-pentenylene, 4-pentenylene, 1,3-butadienylene, 1,3-pentadienylene, 2-penten-4-ynylene, 2-hexenylene, 1-hexenylene, 5-hexenylene, 3-hexenylene, 4-hexenylene, 3,3-dimethyl-1-propenylene, 2-ethyl-1-propenylene, 1,3,5-hexatrienylene, 1,3-hexadienylene, 1,4-hexadienylene) and the like. Among these, $C_2$-$C_4$ alkenylene is more preferable.

The above-mentioned lower alkenylene may be an E-form or Z-form. When the compound of the present invention has a lower alkenylene moiety, the compound of the present invention encompasses any stereoisomer wherein the lower alkenylene moiety is an E-structure or Z-structure.

Examples of the "lower alkynylene" include a straight chain or branched chain alkynylene having a carbon number of 2 to 6, which has 1 to 3 triple bonds (e.g., ethynylene, 1-propynylene, 1-methyl-1-propynylene, 2-methyl-1-propynylene, 2-propynylene, 2-butynylene, 1-butynylene, 3-butynylene, 2-pentynylene, 1-pentynylene, 3-pentynylene, 4-pentynylene, 2-pentyn-4-ynylene, 2-hexynylene, 1-hexynylene, 5-hexynylene, 3-hexynylene, 4-hexynylene, 3,3-diethyl-1-propynylene, 2-ethyl-1-propynylene) and the like. Among these, $C_2$-$C_4$ alkynylene is more preferable.

Examples of the "aryl" include $C_6$-$C_{10}$ aryl (e.g., phenyl and naphthyl) and the like, where the "aryl" may be substituted by 1 to 3 substituents and the position of substitution is not particularly limited.

Examples of the "aralkyl" include aralkyl wherein the aryl moiety has a carbon number of 6 to 10 [that is, the aryl moiety is $C_6$-$C_{10}$ aryl of the above-mentioned "aryl"], and the alkyl moiety has a carbon number of 1 to 6 [that is, the alkyl moiety is $C_1$-$C_6$ alkyl of the above-mentioned "lower alkyl"] (e.g., benzyl, phenethyl, 1-naphthylmethyl, 2-naphthylmethyl, 3-phenylpropyl, 4-phenylbutyl and 5-phenylpentyl) and the like.

Examples of the "cyclo lower alkyl" include cycloalkyl having a carbon number of 3 to 6 (e.g., cyclopropyl, cyclobutyl, cyclopentyl, cyclohexyl) and the like.

Examples of the "cyclo lower alkoxycarbonyl" include cycloalkoxycarbonyl wherein the cycloalkyl moiety has a carbon number of 3 to 6 (e.g., cyclopropyloxycarbonyl, cyclobutyloxycarbonyl, cyclopentyloxycarbonyl, cyclohexyloxycarbonyl) and the like.

Examples of the "heterocycle" include "aromatic heterocycle" and "non-aromatic heterocycle". Examples of the "aromatic heterocycle" include a 5- to 10-membered aromatic heterocycle containing, besides carbon atoms, 1 to 3 hetero atoms selected from nitrogen, oxygen and sulfur atom and the like, for example, thiophene, furan, pyrrole, imidazole, pyrazole, thiazole, isothiazole, oxazole, isoxazole, pyridine, pyridazine, pyrimidine, pyrazine and the like. Examples of the "non-aromatic heterocycle" include a 5- to 10-membered non-aromatic heterocycle containing, besides carbon atoms, 1 to 3 hetero atom selected from nitrogen, oxygen and sulfur atom and the like, for example, pyrrolidine, imidazoline, pyrazolidine, pyrazoline, piperidine, piperazine, morpholine, thiomorpholine, dioxolane, oxazolidine, thiazolidine, triazolysine and the like.

Examples of the "acyl" include alkylcarbonyl, arylcarbonyl and the like.

Examples of the "alkylcarbonyl" include alkylcarbonyl wherein the alkyl moiety has 1 to 6 carbon atoms [that is, the alkyl moiety is $C_1$-$C_6$ alkyl of the above-mentioned "lower alkyl"] (e.g., acetyl, propionyl, butyryl, isobutyryl, valeryl, isovaleryl, pivaloyl, hexanoyl, heptanoyl and decanoyl) and the like.

Examples of the "arylcarbonyl" include arylcarbonyl wherein the aryl moiety has 6 to 10 carbon atoms [that is, the aryl moiety is $C_6$-$C_{10}$ aryl of the above-mentioned "aryl"] (e.g., benzoyl and naphthoyl) and the like.

Examples of the "alkoxycarbonyl" include alkyloxycarbonyl, aralkyloxycarbonyl and the like.

Examples of the "alkyloxycarbonyl" include alkyloxycarbonyl wherein the alkyl moiety has a carbon number of 1 to 10 (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, tert-pentyloxycarbonyl, hexyloxycarbonyl and decyloxycarbonyl etc.) and the like.

Examples of the "aralkyloxycarbonyl" include aralkyloxycarbonyl wherein the aryl moiety has a carbon number of 6 to 10 [that is, the aryl moiety is $C_6$-$C_{10}$ aryl of the above-mentioned "aryl"], and the alkyl moiety has a carbon number of 1 to 6 [that is, the alkyl moiety is $C_1$-$C_6$ alkyl of the above-mentioned "lower alkyl"] (e.g., benzyloxycarbonyl, phenethyloxycarbonyl, 1-naphthylmethyloxycarbonyl, 2-naphthylmethyloxycarbonyl, 3-phenylpropyloxycarbonyl, 4-phenylbutyloxycarbonyl and 5-phenylpentyloxycarbonyl etc.) and the like.

Examples of the "acyl" for $R^1$ in the formula (I) include those defined above and the like, preferably alkylcarbonyl (the alkylcarbonyl is as defined above) and the like, particularly preferably acetyl and the like.

Examples of the "divalent residue derived from the optionally substituted thiazole" for X in the formula (I) include

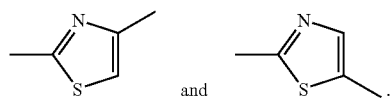

The "thiazole" may have a substituent, and the position of substitution is not particularly limited. Examples of the "substituent" of the above-mentioned "optionally substituted thiazole" include a group described in the following (1)-(12) and the like.

(1) halogen (e.g., fluorine, chlorine, bromine);
(2) alkoxycarbonyl defined above (e.g., ethoxycarbonyl);
(3) optionally substituted aryl (aryl is as defined above, and may be substituted by —$SO_2$-(lower alkyl) wherein the lower alkyl is as defined above and the like, where the position of substitution is not particularly limited) (e.g., phenyl and 4-(methylsulfonyl)phenyl);
(4) a group of the formula: —$CONR^aR^b$ wherein $R^a$ is hydrogen, lower alkyl, aryl or aralkyl, $R^b$ is hydrogen, lower alkyl, aryl or aralkyl, where the lower alkyl, aryl and aralkyl are as defined above (e.g., N-methylaminocarbonyl, N-phenylaminocarbonyl, N,N-dimethylaminocarbonyl and N-benzylaminocarbonyl);
(5) a group of the formula: —CONH—$(CH_2)_k$-aryl wherein k is an integer of 0 to 6; aryl is as defined above, optionally has 1 to 5 substituents selected from the group consisting of —$NO_2$, —$SO_2$-(lower alkyl) wherein the lower alkyl is as defined above, —$CF_3$ and —O-aryl wherein aryl is as defined above, where the position of substitution is not particularly limited;
(6) a group of the formula: —CONH—$(CH_2)_s$-heterocycle wherein s is an integer of 0 to 6; and heterocycle is as defined above (e.g., pyridine);
(7) a group of the formula: —CO-heterocycle wherein heterocycle is as defined above (e.g., pyrrolidine, piperidine, piperazine, thiomorpholine), and heterocycle optionally has 1 to 5 substituents selected from the group consisting of —CO-(lower alkyl) wherein the lower alkyl is as defined above, —CO—O-(lower alkyl) wherein the lower alkyl is as defined above, —$SO_2$-(lower alkyl) wherein the lower alkyl is as defined above, oxo (i.e., =O) and a group of the formula: —$CONR^cR^d$ wherein $R^c$ is hydrogen, lower alkyl, aryl or aralkyl, $R^d$ is hydrogen, lower alkyl, aryl or aralkyl, and lower alkyl, aryl and aralkyl are as defined above, where the position of substitution is not particularly limited;
(8) a group of the formula: —$(CH_2)_t$-aryl wherein t is an integer of 1 to 6; aryl is as defined above, and optionally has 1 to 5 substituents selected from the group consisting of —S-(lower alkyl) wherein lower alkyl is as defined above, —$SO_2$-(lower alkyl) wherein lower alkyl is as defined above, —$SO_2$—$NR^vR^w$ wherein $R^v$ is hydrogen, lower alkyl, aryl or aralkyl, $R^w$ is hydrogen, lower alkyl, aryl or aralkyl, and lower alkyl, aryl and aralkyl are as defined above, —$CO_2$-(lower alkyl) wherein lower alkyl is as defined above, —NHCO—O-(lower alkyl) wherein lower alkyl is as defined above and a group of the formula: —$CONR^eR^f$ wherein $R^e$ is hydrogen, lower alkyl, aryl or aralkyl, $R^f$ is hydrogen, lower alkyl, aryl or aralkyl, and lower alkyl, aryl and aralkyl are as defined above, where the position of substitution is not particularly limited;
(9) a group of the formula: —$(CH^2)_o$-heterocycle wherein o is an integer of 0 to 6; heterocycle is as defined above (e.g., pyrrolidine, piperidine, piperazine, morpholine, thiomorpholine), and optionally has 1 to 5 substituents selected from the group consisting of oxo (that is, =O); —CO-(lower alkyl) wherein lower alkyl is as defined above; —CO—O-(lower alkyl) wherein lower alkyl is as defined above; —$SO_2$-(lower alkyl) wherein lower alkyl is as defined above; —CO-(heterocycle) wherein heterocycle is as defined above (e.g., pyrrolidine, piperazine and morpholine), and optionally has 1 to 5 substituents selected from the group consisting of lower alkyl (lower alkyl is as defined above) and halogen (e.g., fluorine, chlorine, bromine), where the position of substitution is not particularly limited; and a group of the formula: —$CONR^gR^h$ wherein $R^g$ is hydrogen, lower alkyl, aryl or aralkyl, $R^h$ is hydrogen, lower alkyl, aryl or aralkyl, and lower alkyl, aryl and aralkyl are as defined above, where the position of substitution is not particularly limited;
(10) a group of the formula: —$(CH_2)_p$—$NR^iR^j$ wherein p is an integer of 0-6; $R^i$ is hydrogen, acyl, lower alkyl, aryl or aralkyl, $R^j$ is hydrogen, acyl, lower alkyl, aryl or aralkyl, and acyl, lower alkyl, aryl and aralkyl are as defined above, and lower alkyl optionally has 1 to 5 substituents selected from the group consisting of a group of the formula: —$CONR^kR^l$ wherein $R^k$ is hydrogen, lower alkyl, aryl or aralkyl, $R^l$ is hydrogen, lower alkyl, aryl or aralkyl, and lower alkyl, aryl and aralkyl are as defined above, where the position of substitution is not particularly limited;
(11) a group of the formula: —CON(H or lower alkyl)-$(CHR^m)_q$-T wherein q is an integer of 0 to 6; lower alkyl is as defined above; $R^m$ is hydrogen, aralkyl defined above or alkyl defined above (particularly lower alkyl), these are optionally substituted by 1 to 3 substituents selected from the group consisting of —OH and —$CONH_2$, where the position of substitution is not particularly limited; T is hydrogen; a group of the formula: —$CONR^nR^o$ wherein $R^n$ is hydrogen, lower alkyl, aryl or aralkyl, $R^o$ is hydrogen, lower alkyl, aryl or aralkyl, and lower alkyl, aryl and aralkyl are as defined above; —NH—CO—$R^p$ wherein $R^p$ is lower alkyl defined above or aralkyl defined above; —NH—$SO_2$—(lower alkyl) wherein lower alkyl is as defined above; —$SO_2$—(lower alkyl) wherein lower alkyl is as defined above; -heterocycle wherein heterocycle is as defined above (e.g., pyridine, pyrrolidine and morpholine), optionally has 1 to 3 substituents (e.g., oxo (that is, =O)), where the position of substitution is not particularly limited; or —CO-(heterocycle) wherein heterocycle is as defined above (e.g., piperidine and morpholine)); and
(12) a group of the formula: —$(CH_2)_r$—CO—$NR^tR^u$ wherein r is an integer of 1 to 6; $R^t$ is hydrogen, lower alkyl, aryl or aralkyl, $R^u$ is hydrogen, lower alkyl, aryl or aralkyl, and lower alkyl, aryl and aralkyl are as defined above.

The position of substitution on aryl or heterocycle may be any and is not particularly limited. Preferable "substituent" of the above-mentioned "optionally substituted thiazole" is methylsulfonylbenzyl, sulfamoylbenzyl (e.g., 4-sulfamoylbenzyl) and the like. The position of substitution of the methylsulfonyl group, sulfamoyl group and the like is not particularly limited.

As the "divalent residue derived from thiazole" moiety of the "divalent residue derived from optionally substituted thiazole" for X in the formula (I),

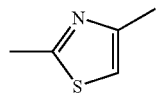

is preferable. As the "substituent" of the "divalent residue derived from optionally substituted thiazole", methylsulfonylbenzyl, sulfamoylbenzyl (e.g., 4-sulfamoylbenzyl) and the like are preferable.

The lower alkylene, lower alkenylene and lower alkynylene for J or M of the formula (III): J-L-M for Y in the formula (I) may be those defined above and the like.

Specific examples of the formula (III): J-L-M for Y in the formula (I) include —$(CH_2)_n$—, —$(CH_2)_n$—NH—$(CH_2)_{n'}$—, —$(CH_2)_n$—O—$(CH_2)_{n'}$—, —$(CH_2)_n$—CO—O—$(CH_2)_{n'}$—, —$(CH_2)_n$—O—CO—$(CH_2)_{n'}$—, —$(CH_2)_n$—CO—NH—$(CH_2)_{n'}$—, —$(CH_2)_n$—NH—CO—$(CH_2)_{n'}$—, —$(CH_2)_n$—SO_2—NH—$(CH_2)_{n'}$—, and —$(CH_2)_n$—NH—SO_2—$(CH_2)_{n'}$— (wherein n and n' are each an integer of 0 to 6, n is preferably an integer of 0 to 3, and n' is preferably an integer of 0 to 3) and the like. Among these, —$(CH_2)_n$—, —$(CH_2)_n$—NH—$(CH_2)_{n'}$—, —$(CH_2)_n$—O—$(CH_2)_{n'}$—, —$(CH_2)_n$—CO—O—$(CH_2)_{n'}$—, and —$(CH_2)_n$—CO—NH—$(CH_2)_{n'}$— are preferable, and —$(CH_2)_n$— is particularly preferable. Specifically, —$(CH_2)_2$—, —$CH_2$—CO—, —$CH_2$—NH—, —$CH_2$—O—, —CO—O—, —CO—NH— and the like can also be mentioned.

Specific examples of the divalent residue derived from optionally substituted benzene or divalent residue derived from optionally substituted thiophene for A in the formula (II): A-B-D-E for Z in the formula (I) include

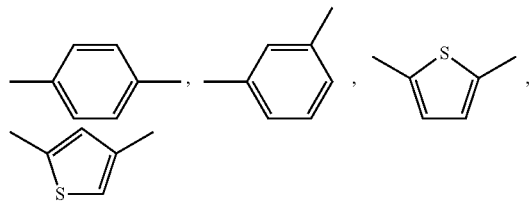

and the like.

"Benzene" and "thiophene" may have a substituent, and the position of substitution is not particularly limited. Examples of the "substituent" of the above-mentioned "optionally substituted benzene" and "optionally substituted thiophene" include halogen (e.g., fluorine, chlorine, bromine), lower alkyl (e.g., methyl, ethyl), lower alkoxy (e.g., methoxy), acyl (e.g., acetyl), halogenated alkyl (e.g., trifluoromethyl) and the like.

Examples of the lower alkyl and acyl for $R^2$ of —$(CH_2)_l$—$NR^2$—CO— represented by B include those defined above and the like.

l in —$(CH_2)_l$—$NR_2$—CO— represented by B is an integer of 1 to 6 (preferably 1 to 3).

m in —$(CH_2)_m$—O—CO— and —$(CH_2)_m$—S—CO— represented by B is an integer of 0 to 6 (preferably 0 to 3).

Specific examples of B include —O—CO—, —$CH_2$—O—CO—, —$(CH_2)_2$—O—CO—, —$(CH_2)_3$—O—CO—, —$CH_2$—NH—CO—, —$(CH_2)_2$—NH—CO—, —$(CH_2)_3$—NH—CO—, —S—CO—, —$CH_2$—S—CO— and —$(CH_2)_2$—S—CO— and the like.

Examples of the lower alkyl, alkoxycarbonyl and acyl for $R^3$ in —$NR^3$— represented by D include those defined above and the like. Specific examples of D include —NH—, —N($CH_3$)— and the like.

Examples of the "optionally substituted amino" for E include unsubstituted amino, and amino substituted by 1 or 2 substituents. The "optionally substituted amino" is represented by the formula —$NR^4R^5$.

Examples of $R^4$ and $R^5$ include groups of lower alkyl, acyl (particularly, lower alkylcarbonyl, hydroxy lower alkylcarbonyl), alkoxycarbonyl, hydroxyalkoxycarbonyl, aryl, aralkyl, cyclo lower alkyl, cyclo lower alkoxycarbonyl, sulfuryl, sulfinyl, phosphoryl, heterocycle and the like, which are each unsubstituted or optionally substituted by hydroxy etc., hydrogen and the like. The lower alkyl, acyl (particularly, lower alkylcarbonyl), alkoxycarbonyl, aryl, aralkyl, cyclo lower alkyl, cyclo lower alkoxycarbonyl and heterocycle are as defined above.

Specific examples of $R^4$ and $R^5$ include hydrogen, lower alkyl (e.g., methyl, ethyl and the like), acetyl, butanoyl, decanoyl, 3-hydroxypropanoyl, 6-hydroxyhexanoyl, ethoxycarbonyl, butoxycarbonyl, decyloxycarbonyl, 2-hydroxyethoxycarbonyl and the like.

The amino moiety of "optionally substituted amino" for E may be protected (i.e., substituted) according to the method described in "Protective Groups in Organic Synthesis 3rd Edition" (John Wiley and Sons, 1999), and the like. $R^4$ and $R^5$ may be the same or different.

As the —B-D-E part (molecule terminal) of the formula (II): A-B-D-E which is shown by Z in the formula (I), B is —O—CO—, —$CH_2$—O—CO—, —$(CH_2)_2$—O—CO—, —$(CH_2)_3$—O—CO—, —$CH_2$—NH—CO—, —$(CH_2)_2$—NH—CO—, —$(CH_2)_3$—NH—CO—, —S—CO—, —$CH_2$—S—CO— or —$(CH_2)_2$—S—CO—; D is —NH—; and E is —$NH_2$ and the like. Specifically, the —B-D-E part is, for example, —O—CO—NH—$NH_2$, —$CH_2$—O—CO—NH—$NH_2$, —$(CH_2)_2$—O—CO—NH—$NH_2$, —$(CH_2)_3$—O—CO—NH—$NH_2$, —$CH_2$—NH—CO—NH—$NH_2$, —$(CH_2)_2$—NH—CO—NH—$NH_2$, —$(CH_2)_3$—NH—CO—NH—$NH_2$, —$CH_2$—S—CO—NH—$NH_2$, —$(CH_2)_2$—S—CO—NH—$NH_2$ and the like. Preferred is —O—CO—NH—$NH_2$, —$CH_2$—O—CO—NH—$NH_2$, —$(CH_2)_2$—O—CO—, —$(CH_2)_3$—O—CO—NH—$NH_2$, —$CH_2$—NH—CO—NH—$NH_2$, —$(CH_2)_2$—NH—CO— or —$CH_2$—S—CO—. Particularly preferred is —$CH_2$—O—CO—NH—$NH_2$ or —$CH_2$—NH—CO—NH—$NH_2$.

Examples of compound (I) include
4-{2-[2-(acetylamino)-1,3-thiazol-4-yl]ethyl}phenyl hydrazinecarboxylate,
4-{2-[2-(acetylamino)-1,3-thiazol-4-yl]ethyl}benzyl hydrazinecarboxylate,
2-(4-{2-[2-(acetylamino)-1,3-thiazol-4-yl]ethyl}phenyl) ethyl hydrazinecarboxylate,
4-{2-[2-(acetylamino)-1,3-thiazol-4-yl]ethyl}-2-fluorobenzyl hydrazinecarboxylate,
4-{2-[2-(acetylamino)-1,3-thiazol-4-yl]ethyl}-3-fluorobenzyl hydrazinecarboxylate,
4-{2-[2-(acetylamino)-1,3-thiazol-4-yl]ethyl}-2,3-difluorobenzyl hydrazinecarboxylate,
2-(4-{[2-(acetylamino)-1,3-thiazol-4-yl]methoxy}phenyl) ethyl hydrazinecarboxylate, 4-{2-[(hydrazinocarbonyl)oxy]ethyl}phenyl 2-(acetylamino)-1,3-thiazole-4-carboxylate,
2-[4-({[2-(acetylamino)-1,3-thiazol-4-yl]carbonyl}amino)phenyl]ethyl hydrazinecarboxylate,
3-{2-[2-(acetylamino)-1,3-thiazol-4-yl]ethyl}phenyl hydrazinecarboxylate,
3-{2-[2-(acetylamino)-1,3-thiazol-4-yl]ethyl}benzyl hydrazinecarboxylate,
2-(3-{2-[2-(acetylamino)-1,3-thiazol-4-yl]ethyl}phenyl)ethyl hydrazinecarboxylate,
{5-[2-(2-acetylamino-1,3-thiazol-4-yl)ethyl]thiophen-2-yl}methyl hydrazinecarboxylate,
2-(5-{2-[2-(acetylamino)-1,3-thiazol-4-yl]ethyl}thiophen-2-yl)ethyl hydrazinecarboxylate,
3-(4-{2-[2-(acetylamino)-1,3-thiazol-4-yl]ethyl}thiophen-2-yl)propyl hydrazinecarboxylate,
3-(5-{2-[2-(acetylamino)-1,3-thiazol-4-yl]ethyl}thiophen-3-yl)propyl hydrazinecarboxylate,
3-(5-{2-[2-(acetylamino)-1,3-thiazol-4-yl]ethyl}-3-methylthiophen-2-yl)propyl hydrazinecarboxylate,
N-(4-{2-[2-(acetylamino)-1,3-thiazol-4-yl]ethyl}benzyl)hydrazinecarboxamide,
N-[2-(4-{2-[2-(acetylamino)-1,3-thiazol-4-yl]ethyl}phenyl)ethyl]hydrazinecarboxamide,
N-(4-{2-[2-(acetylamino)-1,3-thiazol-4-yl]ethyl}-2-fluorobenzyl)hydrazinecarboxamide,
N-(4-{2-[2-(acetylamino)-1,3-thiazol-4-yl]ethyl}-3-fluorobenzyl)hydrazinecarboxamide,
N-(4-{2-[2-(acetylamino)-1,3-thiazol-4-yl]ethyl}-2,3-difluorobenzyl)hydrazinecarboxamide,
N-[4-({[2-(acetylamino)-1,3-thiazol-4-yl]methyl}amino)benzyl]hydrazinecarboxamide,
2-(acetylamino)-N-(4-{[(hydrazinocarbonyl)amino]methyl}phenyl)-1,3-thiazole-4-carboxamide,
N-[2-(4-{[2-(acetylamino)-1,3-thiazol-4-yl]methoxy}phenyl)ethyl]hydrazinecarboxamide,
4-{2-[(hydrazinocarbonyl)amino]ethyl}phenyl 2-(acetylamino)-1,3-thiazole-4-carboxylate,
N-(3-{2-[2-(acetylamino)-1,3-thiazol-4-yl]ethyl}benzyl)hydrazinecarboxamide,
N-[2-(3-{2-[2-(acetylamino)-1,3-thiazol-4-yl]ethyl}phenyl)ethyl]hydrazinecarboxamide,
N-[2-(5-{2-[2-(acetylamino)-1,3-thiazol-4-yl]ethyl}thiophen-2-yl)methyl]hydrazinecarboxamide,
N-[2-(5-{2-[2-(acetylamino)-1,3-thiazol-4-yl]ethyl}thiophen-2-yl)ethyl]hydrazinecarboxamide,
N-[3-(4-{2-[2-(acetylamino)-1,3-thiazol-4-yl]ethyl}thiophen-2-yl)propyl]hydrazinecarboxamide,
N-[3-(5-{2-[2-(acetylamino)-1,3-thiazol-4-yl]ethyl}thiophen-3-yl)propyl]hydrazinecarboxamide,
N-[3-(5-{2-[2-(acetylamino)-1,3-thiazol-4-yl]ethyl}-3-methylthiophen-2-yl)propyl]hydrazinecarboxamide,
S-(4-{2-[2-(acetylamino)-1,3-thiazol-4-yl]ethyl}benzyl) hydrazinecarbothioate,
S-[2-(4-{2-[2-(acetylamino)-1,3-thiazol-4-yl]ethyl}phenyl)ethyl]hydrazinecarbothioate,
S-[(5-{2-[2-(acetylamino)-1,3-thiazol-4-yl]ethyl}thiophen-2-yl)methyl]hydrazinecarbothioate and the like can be mentioned.

Preferred are 4-{2-[2-(acetylamino)-1,3-thiazol-4-yl]ethyl}phenyl hydrazinecarboxylate, 4-{2-[2-(acetylamino)-1,3-thiazol-4-yl]ethyl}benzyl hydrazinecarboxylate, N-(4-{2-[2-(acetylamino)-1,3-thiazol-4-yl]ethyl}benzyl) hydrazinecarboxamide and the like.

When compound (I) has an asymmetric carbon atom in the structure, the present invention encompasses all enantiomers and diastereomers.

Compound (I) can also be converted to a pharmaceutically acceptable salt. The pharmaceutically acceptable salt in the present invention is not particularly limited as long as it is a nontoxic pharmaceutically acceptable general salt, and a salt with an inorganic or organic base, acid addition salt and the like can be mentioned. Examples of the salt with an inorganic or organic base include alkali metal salt (e.g., sodium salt, potassium salt and the like), alkaline earth metal salt (e.g., calcium salt, magnesium salt and the like), ammonium salt, and amine salt (e.g., triethylamine salt, N-benzyl-N-methylamine salt and the like) and the like. Examples of the acid addition salt include salts derived from mineral acid (e.g., hydrochloric acid, hydrobromic acid, hydroiodic acid, phosphoric acid, metaphosphoric acid, nitric acid and sulfuric acid), and salts derived from organic acid (e.g., tartaric acid, acetic acid, trifluoroacetic acid, citric acid, malic acid, lactic acid, fumaric acid, maleic acid, benzoic acid, glycol acid, gluconic acid, succinic acid and arylsulfonic acid (e.g., p-toluenesulfonic acid)) and the like.

The compound of the present invention can be used as a prodrug for the below-mentioned pharmaceutical agent and the like. The term "prodrug" means any compound that can be converted to a VAP-1 inhibitor in the body after administration. The prodrug may be any optionally pharmaceutically acceptable prodrug of the compound of the present invention.

The compound of the present invention can be used as an active ingredient of a pharmaceutical agent such as a VAP-1 inhibitor, a pharmaceutical agent for the prophylaxis or treatment of a VAP-1 associated disease and the like.

The "vascular adhesion protein-1 (VAP-1) associated disease" is not particularly limited as long as it is a disease wherein VAP-1 is related to the expression and/or progress of the disease, and includes a disease selected from the group consisting of vascular hyperpermeable disease [e.g., macular edema (e.g., diabetic and nondiabetic macular edema), aged macular degeneration, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, ocular inflammatory disease caused by bacterial or viral infection, and by ophthalmic operation, ocular inflammatory disease caused by physical injury to the eye, symptom caused by ocular inflammatory disease including itching, flare, edema and ulcer, erythema, erythema exsudativum multiforme, erythema nodosum, erythema annulare, scleredema, dermatitis (e.g., psoriasis, allergic lesion, lichen planus, pityriasis rosea, contact dermatitis, atopic dermatitis, pityriasis rubra pilaris), angioneurotic edema, laryngeal edema, glottic edema, subglottic laryngitis, bronchitis, rhinitis, pharyngitis, sinusitis and laryngitis or otitis media], cirrhosis, essential stabilized hypertension, diabetes, arteriosclerosis, endothelial injury (in, for example, diabetes, arteriosclerosis and hypertension), cardiovascular disease relating to diabetes or uremia, pain relating to gout and arthritis, inflammatory disease or symptom of binding tissue (e.g., rheumatoid arthritis, ankylosing spondylitis, psoriatic arthritis and osteoarthritis or degenerative joint disease, Reiter's syndrome, Sjogren's syndrome, Behcet's syndrome, relapsing polychondritis, systemic lupus erythematosus, discoid lupus erythematodes, systemic sclerosis, eosinophilic fasciitis, polymyositis, dermatomyositis, polymyalgia rheumatica, vasculitis, temporal arthritis, polyarteritis nodosa, Wegener's granulomatosis, mixed connective tissue diseases and juvenile rheumatoid arthritis), inflammatory disease or symptom of gastrointestinal tract [e.g., Crohn's disease, ulcerative colitis, irritable bowel syndrome (e.g., spastic colon), fibrosis of the liver, inflammation of the oral mucous membrane (e.g., stomatitis and recurrent aphthous stomatitis)], inflammatory disease or symptom of central nervous system (e.g., multiple sclerosis, Alzheimer's disease, and ischemia-reperfusion injury relating to ischemic stroke), pulmonary inflammatory disease or symptom (e.g., asthma, adult respiratory distress syndrome, chronic obliterative pulmonary diseases), disease relating to carbohydrate metabolism (e.g., diabetes and complications derived from diabetes (e.g., diabetic neuropathy, diabetic nephropathy)) including disease of microvessel and large vessel (e.g., arteriosclerosis, retinopathy, nephropathy, nephrotic syndrome and neuropathy (e.g., multiple neuropathy, mononeuropathy and autonomic neuropathy), foot ulcer, articular problem and increase in infection risk), disease relating to abnormality in the differentiation or function of adipocyte or function of smooth muscle cell (e.g., arteriosclerosis and obesity), vascular disease [e.g., artheromatous atherosclerosis, nonartheromatous atherosclerotic disease, ischemic cardiac diseases including myocardial infarction and peripheral arterial obstruction, Raynaud's disease and Raynaud's phenomenon, thromboangiitis obliterans (Buerger's disease)], chronic arthritis, inflammatory bowel disease, SSAO-mediated complications [e.g., diabetes (e.g., insulin-dependent diabetes (IDDM) and noninsulin-dependent diabetes (NIDDM)) and vascular complications (e.g., heart attack, angina pectoris, apoplexy, amputation, blindness and renal failure)], ophthalmic disease associated with hypoxia or ischemia [e.g., retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency] and cataract, and the like.

The "prophylaxis or treatment of a vascular adhesion protein-1 (VAP-1) associated disease" means administration of the compound of the present invention having a VAP-1 inhibitory action (i.e., VAP-1 inhibitor) to a subject of administration for the purpose of the treatment (including prophylaxis, amelioration of symptom, reduction of symptom, prevention of progress and cure) of the above-mentioned VAP-1 associated disease.

The subjects of the administration of the pharmaceutical agent, pharmaceutical composition, VAP-1 inhibitor, pharmaceutical agent for the prophylaxis or treatment of a VAP-1 associated disease in the present invention (hereinafter these are also collectively referred to as the pharmaceutical agent of the present invention) are various animals (e.g., mammals such as human, mouse, rat, swine, dog, cat, horse, bovine and the like, particularly human) and the like.

The pharmaceutical agent of the present invention can be administered by any route. The administration route in the present invention includes systemic administration (e.g., oral administration or injection administration), topical administration (e.g., instillation administration, intraocular administration and transdermal administration) and the like. The administration route of the pharmaceutical agent of the present invention can be appropriately determined according to whether the application to a VAP-1 associated disease is prophylactic or therapeutic and the like.

The pharmaceutical agent of the present invention is preferably administered rapidly after a subject of administration such as a mammal, particularly human, is diagnosed to have a risk of a VAP-1 associated disease (prophylactic treatment), or administered rapidly after the subject of administration shows the onset of a VAP-1 associated disease (therapeutic treatment). The treatment plan can be appropriately determined according to the kind of the active ingredient to be used, dose, administration route, cause and, where necessary, level of awareness of the VAP-1 associated disease and the like.

As an administration method of the pharmaceutical agent of the present invention, a method known per se for general pharmaceutical agents can be used. The administration route may be an appropriately effective one and one or more routes can be used. Accordingly, the above-mentioned administration routes are mere exemplifications free of any limitation.

The dose of the pharmaceutical agent of the present invention for a subject of administration such as animal including human, particularly human, is an amount sufficient to provide a desired response in the subject of administration for a reasonable period of time. The dose is appropriately determined according to various factors including the strength of the active ingredient to be used, age, kind, symptom, disease state, body weight and severity of disease of the subject of administration, the route, timing and frequency of the administration and the like. The dose can also be appropriately controlled according to the route, timing and frequency of the administration and the like. Depending on the symptom or disease state, a long-term treatment involving plural times of administration may be necessary.

The dose and administration schedule can be determined by a technique within the range known to those of ordinary skill in the art. In general, the treatment or prophylaxis is started from a dose lower than the optimal dose of the compound. Thereafter, the dose is gradually increased until the optimal effect is obtained under the circumstances. The pharmaceutical agent of the present invention (VAP-1 inhibitor and the like) can be administered generally at a dose of about 0.03 ng/kg body weight/day-about 300 mg/kg body weight/day, preferably about 0.003 µg/kg body weight/day-about 10 mg/kg body weight/day, by a single administration or 2-4 portions a day or in a sustained manner.

The pharmaceutical composition of the present invention preferably contains a "pharmaceutically acceptable carrier" and, as an active ingredient, the compound of the present invention (VAP-1 inhibitor) in an amount sufficient for the prophylactic or therapeutic treatment of a VAP-1 associated disease. The carrier may be any which is generally used as a pharmaceutical agent and is not particularly limited except when limited by physicochemical items for consideration (e.g., solubility, and lack of reactivity with the compound) and administration route.

While the amount of the compound of the present invention in the pharmaceutical agent of the present invention varies depending on the formulation of the composition, it is generally 0.00001-10.0 wt %, preferably 0.001-5 wt %, more preferably 0.001-1 wt %.

The administration form of the pharmaceutical agent of the present invention is not particularly limited, and can be administered in various forms to achieve the desired VAP-1 inhibitory action. The pharmaceutical agent of the present invention is formulated using the compound of the present invention alone or in a combination with a pharmaceutically acceptable carrier or an additive such as diluent and the like, and orally or parenterally administered. The characteristics and property of the preparation are determined by the solubility and chemical property of the active ingredient, selected administration route and standard pharmaceutical practice. The preparation to be used for oral administration may be a solid dosage forms (e.g., capsule, tablet, powder) or a liquid form (e.g., solution or suspension) and the like. The preparation to be used for parenteral administration may be an injection, drip infusion, and the like, which are in the form of an aseptic solution or suspension. The solid oral preparation can contain a general excipient and the like. The liquid oral preparation can contain various aromatic, colorant, preservative, stabilizer, solubilizer, suspending agent and the like. The parenteral preparation is, for example, an aseptic aqueous or nonaqueous solution or suspension, and can contain particular various preservatives, stabilizer, buffer agent, solubilizer, suspending agent and the like. Where necessary, various isotonicity agents may be added.

The pharmaceutical agent of the present invention may contain other pharmaceutically active compound as long as it does not inhibit the effect of the invention.

The pharmaceutical agent of the present invention can be simultaneously administered with other pharmaceutically active compound as long as it does not inhibit the effect of the invention. The "simultaneous administration" means administration of other pharmaceutically active compound before or simultaneous (e.g., in the same or different preparation) or after administration of the pharmaceutical agent of the present invention. For example, corticosteroid, prednisone, methyl prednisone, dexamethasone or triamcinolone acetonide or noncorticosteroid anti-inflammatory compound (e.g., ibuprofen or flurbiprofen) can be simultaneously administered. Similarly, vitamin and mineral (e.g., zinc, antioxidant (e.g., carotenoid (e.g., xanthophyll carotenoid-like zeaxanthine or lutein))) and micronutrient and the like can be simultaneously administered.

The compound of the present invention is useful for the production of a pharmaceutical agent such as a VAP-1 inhibitor and a pharmaceutical agent for the prophylaxis or treatment of a VAP-1 associated disease.

Compound (I) can be produced by the following procedures. However, the procedures are not limited thereto. The procedures can be modified according to a general method known per se.

Compound (I) can also be represented by the formula:

$R^1$—NH—X—Y-A-B-D-E wherein each symbol is as defined above.

The steps of the production procedure of compound (I) are shown in the following scheme 1.

Compound (I) can be produced by chemically binding four compounds (1), (2), (3), and carbon monoxide equivalent (4) as partial structures shown in the following scheme 1. Compounds (1), (2), (3) may be in the form of salts.

The order of binding may be binding (1) and (2) and thereafter (3) via carbon monoxide equivalent (4), or first binding (2) and (3) via carbon monoxide equivalent (4) and finally (1). Compound (I) can be produced by both orders. Where necessary, deprotection of D-E, conversion into a pharmaceutically acceptable salt and the like may be performed. The production method of compound (I) is not limited to have the above, and can appropriately modify the steps according to a general method known per se.

Scheme 1

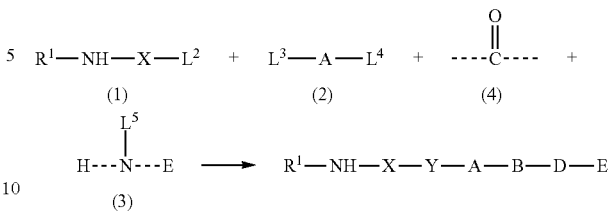

wherein $R^1$, X, Y, A, B, D, and E are as defined above. $L^2$ is a reactive functional group which forms a chemical bond with $L^3$ of compound (2) to form Y. $L^3$ is a reactive functional group which forms a chemical bond with $L^2$ of compound (1) to form Y. $L^4$ is a functional group that reacts with compound (3) via carbon monoxide equivalent (4) to form B, whereby a carbazic acid ester structure, a carbazic acid thioester structure and a semicarbazide structure are constructed at the molecule terminal of compound (I). $L^5$ is hydrogen, lower alkyl, alkoxycarbonyl, acyl or a protecting group.

$L^2$ of compound (1) is a reactive functional group which forms a chemical bond with $L^3$ of compound (2) to form Y. Examples thereof include, but are not limited to, —$(CH_2)_u$—CHO, —$(CH_2)_u$—OH, —$(CH_2)_u$-halogen, —$(CH_2)_u$—COOH, —$(CH_2)_u$—CO-halogen, —$(CH_2)_u$—$NH_2$, —$(CH_2)_u$—$SO_3H$, —$(CH_2)_u$—$SO_2$-halogen, —$(CH_2)_u$—O-acyl derived from —$(CH_2)_u$—OH (e.g., —$(CH_2)_u$—O-acetyl and the like), —$(CH_2)_u$-sulfonic acid ester (e.g., —$(CH_2)_u$—$OSO_2CH_3$ and the like), Wittig reagent derived from —$(CH_2)_u$-halogen and the like, and the like (wherein u is an integer of 0-6 and halogen is chlorine, bromine or iodine).

Compound (1) and a salt thereof may be commercially available, or can also be produced according to the method known per se, which is described in WO 2004/067521, and the like.

$L^3$ of compound (2) is a reactive functional group which forms a chemical bond with $L^2$ of compound (1) to form Y. Examples thereof include, but are not limited to, —$(CH_2)_v$—CHO, —$(CH_2)_v$—OH, —$(CH_2)_v$-halogen, —$(CH_2)_v$—COOH, —$(CH_2)_v$—CO-halogen, —$(CH_2)_v$—$NH_2$, —$(CH_2)_v$—$SO_3H$, —$(CH_2)_v$—$SO_2$-halogen, —$(CH_2)_v$—O-acyl derived from —$(CH_2)_v$—OH (e.g., —$(CH_2)_v$—O-acetyl and the like), —$(CH_2)_v$-sulfonic acid ester (e.g., —$(CH_2)_v$—$OSO_2CH_3$ and the like), Wittig reagent derived from —$(CH_2)_v$-halogen and the like, and the like (wherein v is an integer of 0-6 and halogen is chlorine, bromine or iodine). $L^4$ is a functional group that reacts with compound (3) via carbon monoxide equivalent (4) or a compound obtained by previously binding carbon monoxide equivalent (4) to compound (3) to form B, whereby a carbazic acid ester structure, a carbazic acid thioester structure and a semicarbazide structure are constructed at the molecule terminal of compound (I). Examples thereof include, but are not particularly limited to, —$(CH_2)_w$—OH, —$(CH_2)_w$—SH, —$(CH_2)_t$—$NHR^2$, $R^2$—$(CH_2)_w$-halogen and the like (wherein w is an integer of 0-6, t is an integer of 1-6, halogen is chlorine, bromine or iodine, and $R^2$ is as defined above.

Compound (2) and a salt thereof may be commercially available, or can also be produced according to the method known per se, which is described in WO 2004/067521, WO 2006/011631 and the like.

Compound (3) is a hydrazine equivalent for constructing a carbazic acid ester structure, a carbazic acid thioester structure and a semicarbazide structure at the molecule terminal of compound (I), and may be commercially available or can be produced according to a method known per se. The protecting group of $L^5$ is a functional group introduced to avoid unnecessary reactions and removed in an appropriate step. Examples thereof include protecting groups of $(CH_3)_3C$—OCO— shown in the Production Examples and the like. Examples of the lower alkyl, alkoxycarbonyl and acyl for $L^5$ are those similar to the lower alkyl, alkoxycarbonyl and acyl for the aforementioned $R^3$.

(4) is a synthetic equivalent (synthon) of carbon monoxide providing a carbonyl group to B, and may be commercially available, or can be produced according to a method known per se. Specifically, 1,1'-carbonyldiimidazole, chloroformic acid esters, phosgene, bis(trichloromethyl)carbonate [triphosgene] and the like can be used nonlimitatively.

When compound (I) wherein Y is carbon chain is produced, compound (1) or a salt thereof is chemically bonded to compound (2) or a salt thereof (or compound obtained by condensation of compound (2) and (3) in advance via carbon monoxide equivalent (4)) utilizing Wittig reaction, Horner-Emmons reaction, aldol condensation reaction, Claisen condensation, or a similar carbon-carbon binding formation reaction to construct Y containing lower alkenylene or lower alkynylene. Appropriate salts of compound (1) and (2) may be the same as those exemplified with regard to compound (I). While various carbon-carbon bond forming reactions are utilizable, when Wittig reaction or a similar reaction is utilized, a desirable example includes —$(CH_2)_u$—CHO for $L^2$ and a phosphonium salt (Wittig reagent) derived from —$(CH_2)_v$-halogen etc. for $L^3$, or a phosphonium salt (Wittig reagent) derived from —$(CH_2)_u$-halogen etc. for $L^2$ and —$(CH_2)_v$—CHO for $L^3$ (wherein u and v are as defined above, and halogen is chlorine, bromine or iodine). The reaction is generally performed in a general solvent such as N,N-dimethylformamide, dimethyl sulfoxide, tetrahydrofuran and dichloromethane, or other organic solvent that does not adversely influence the reaction, or a mixture thereof, in the presence of a general base such as potassium tert-butoxide, sodium hydride, sodium hydroxide and the like. The reaction temperature is not particularly important, and the reaction is performed under cooling or under heating. The resultant product is isolated or purified by a known separation or purification means, concentration, concentration under reduced pressure, solvent extraction, crystallization, recrystallization, phase transition, chromatography and the like, or can also be converted to a salt similar to those exemplified for compound (I).

Where necessary, lower alkenylene or lower alkynylene is hydrogenated for conversion to lower alkylene. When Y is converted to an alkylene bond, a hydrogenation reaction is performed in the presence of various homogeneous catalysts or heterogeneous catalyst according to a general method. Particularly, catalytic hydrogenation using a heterogeneous catalyst is preferable, which is performed in the presence of a catalyst such as palladium carbon or Raney-nickel.

When compound (I) wherein Y is ester, amide or sulfonamide is produced, compound (1) or a salt thereof is condensed with compound (2) or a salt thereof (or compound obtained by condensation of compound (2) and (3) in advance via carbon monoxide equivalent (4)) to construct ester or amide bond. In this case, $L^2$ is —$(CH_2)_u$—OH, —$(CH_2)_u$—$NH_2$, —$(CH_2)_u$-halogen and the like and $L^3$ is —$(CH_2)_v$—COOH, —$(CH_2)_v$—CO halogen, —$(CH_2)_v$—$SO_3H$, —$(CH_2)_v$—$SO_2$-halogen and the like, or $L^2$ is —$(CH_2)_u$—COOH, —$(CH_2)_u$—CO-halogen, —$(CH_2)_u$—$SO_3H$, —$(CH_2)_u$—$SO_2$-halogen and the like and $L^3$ is —$(CH_2)_v$—OH, —$(CH_2)_v$—$NH_2$, —$(CH_2)_v$-halogen and the like, and Y can be constructed based on a general organic synthesis method (wherein u and v are as defined above, and halogen is chlorine, bromine or iodine). The reaction is generally performed in a general solvent such as dichloromethane, acetone, tetrahydrofuran, diethyl ether and N,N-dimethylformamide, and any other organic solvent that does not adversely influence the reaction, or a mixture thereof. Where necessary, a condensation agent such as 1-ethyl-3-(3-dimethylaminopropyl)carbodiimide hydrochloride, N,N'-dicyclohexylcarbodiimide, 1,1'-carbonyldiimidazole and the like is used. The reaction is also performed in the presence of an additive such as N,N-dimethyl-4-aminopyridine, 1-hydroxybenzotriazole, 1-hydroxysuccinimido and 3,4-dihydro-3-hydroxy-4-oxo-1,2,3-benzotriazine. The reaction temperature is not particularly important, and the reaction is performed under cooling or under heating.

When compound (I) wherein Y is a group containing amine is produced, $L^2$ is —$(CH_2)_u$—$NH_2$, or a salt thereof and the like and $L^3$ is —$(CH_2)_v$—CHO, —$(CH_2)_v$-halogen and the like, or $L^2$ is —$(CH_2)_u$—CHO, —$(CH_2)_u$-halogen and the like and $L^3$ is —$(CH_2)_v$—$NH_2$, or a salt thereof and the like, and Y can be constructed based on a general organic synthesis method (wherein u and v are as defined above, and halogen is chlorine, bromine or iodine). Generally, amine and aldehyde is condensed to give a Schiff base, which is reduced by sodium borohydride, sodium cyanoborohydride and the like in a general solvent such as tetrahydrofuran, diethyl ether, alcohol and the like, or any other organic solvent that does not adversely influence the reaction, or a mixture thereof as a reaction solvent, whereby a secondary amine structure is constructed. The same structure is also constructed condensation reaction of amine and a halogen compound. When a halogen compound is utilized, a base such as N,N-diisopropylamine, triethylamine, potassium carbonate and the like is used as a reaction agent, a general solvent such as tetrahydrofuran, acetonitrile and N,N-dimethylformamide, or other organic solvent that does not adversely influence the reaction, or a mixture thereof is used as a reaction solvent. The reaction temperature is not particularly important, and the reaction is performed under cooling or under heating. The resultant product can also be converted to a salt similar to those exemplified for compound (I).

When compound (I) wherein Y is a group containing an ether bond is produced, $L^2$ is —$(CH_2)_u$—OH and the like and $L^3$ is —$(CH_2)_v$—OH, —$(CH_2)_v$-halogen, —$(CH_2)_v$-sulfonic acid ester and the like, or $L^2$ is —$(CH_2)_u$—OH, —$(CH_2)_u$-halogen, —$(CH_2)_u$-sulfonic acid ester and the like and $L^3$ is —$(CH_2)_v$—OH and the like, and Y can be constructed based on a general organic synthesis method (wherein u and v are as defined above, and halogen is chlorine, bromine or iodine). An ether bond can be formed by Williamson method, ether synthesis method from aromatic halide using a copper catalyst and the like, Mitsunobu reaction, other production method known per se. These reactions are generally performed in a general solvent such as acetonitrile, dichloromethane, acetone, tetrahydrofuran and N,N-dimethylformamide, or any other organic solvent that does not adversely influence the reaction, or a mixture thereof. The reaction temperature is not particularly important, and the reaction is performed under cooling or under heating. The resultant product can also be converted to a salt similar to those exemplified for compound (I).

The molecule terminal of compound (I) is a carbazic acid ester structure, a carbazic acid thioester structure, or a semicarbazide structure.

One example of the method of introducing a carbazic acid ester structure, a carbazic acid thioester structure, or a semicarbazide structure into the molecule terminal of compound (I) is shown in the following Scheme 2.

Scheme 2

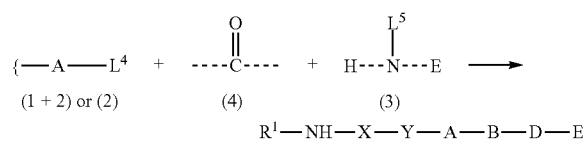

(wherein $R^1$, X, Y, A, B, D, and E are as defined for compound (I) and $L^4$ and $L^5$ are as defined above.)

When carbazic acid ester, i.e., compound (I) wherein B is —$(CH_2)_m$—O—CO— is produced, $L^4$ of compound (2) (or compound obtained by binding compound (1) and (2)) should be a —$(CH_2)_w$—OH structure. It may be incorporated as a hydroxy group into compound (2) in advance as a starting material, or may be constructed as a part of the synthesis step by reduction of the corresponding carboxylic acid, carboxylic acid ester or aldehyde, hydrolysis of halide or ester, hydration of olefin, hydroboration and the like.

$L^4$: —$(CH_2)_w$—OH is reacted with, for example, 1,1'-carbonyldiimidazole as a synthetic equivalent of carbon monoxide (4), and then condensed with hydrazine (or protected hydrazine), whereby a carbazic acid ester structure (in the formula (I), B is —$(CH_2)_w$—O—CO—, D is —$NR^3$—, and E is an optionally substituted amino group) can be constructed at the molecule terminal of compound (I), wherein w is as defined above. Alternatively, a carbazic acid ester structure can be constructed at the molecule terminal of compound (I) by reacting hydrazine (or protected hydrazine) and 1H-imidazole-1-carbohydrazide synthesized, for example, from 1,1'-carbonyldiimidazole with $L^4$: —$(CH_2)_w$—OH, or a metal alcoholate thereof [—$(CH_2)_w$—ONa and the like]. The reaction is generally performed in a general solvent such as tetrahydrofuran, N,N-dimethylformamide, dichloromethane and acetonitrile, or any other organic solvent that does not adversely influence the reaction, or a mixture thereof. Where necessary, deprotection is performed in an appropriate step to give the object compound.

When carbazic acid thioester, i.e., compound (I) wherein B is —$(CH_2)_m$—S—CO— is produced, $L^4$ of compound (2) (or compound obtained by binding compound (1) and (2)) should be a —$(CH_2)_w$—SH structure. It may be incorporated as a sulfanyl group into compound (2) in advance as a starting material, or may be constructed as a part of the synthesis step by a general thiol production method such as functional group conversion of the corresponding alcohol or a halogen compound and the like.

$L^4$: —$(CH_2)_w$—SH is reacted with, for example, 1,1'-carbonyldiimidazole as a synthetic equivalent of carbon monoxide (4), and then condensed with hydrazine (or protected hydrazine), whereby a carbazic acid thioester structure (in the formula (I), B is —$(CH_2)_w$—S—CO—, D is —$NR^3$—, and E is an optionally substituted amino group) can be constructed at the molecule terminal of compound (I), wherein w is as defined above. Alternatively, a carbazic acid thioester structure can be constructed at the molecule terminal of compound (I) by reacting hydrazine (or protected hydrazine) and 1H-imidazole-1-carbohydrazide synthesized, for example, from 1,1'-carbonyldiimidazole with $L^4$: —$(CH_2)_w$—SH, or a metal thiolate thereof [—$(CH_2)_w$—SNa and the like]. The reaction is generally performed in a general solvent such as tetrahydrofuran, N,N-dimethylformamide, dichloromethane and acetonitrile, or any other organic solvent that does not adversely influence the reaction, or a mixture thereof. Where necessary, deprotection is performed in an appropriate step to give the object compound.

When semicarbazide, i.e., compound (I) wherein B is —$(CH_2)_t$—$NR^2$—CO— is produced, $L^4$ should be a —$(CH_2)_t$—$NHR^2$ structure wherein t is an integer of 1-6. It may be incorporated as an amino group or a protected amino group into compound (2) in advance as a starting material, or may be constructed as a part of the synthesis step by reduction of nitro group, cyano group or carboxamide group, functional group conversion of alcohol or halide and the like. The molecule terminal structure wherein B is —$(CH_2)_t$—$NR^2$—CO—, D is —$NR^3$—, and E is an optionally substituted amino group can be constructed by treating the amino group with tert-butyl 2-(1H-imidazol-1-ylcarbonyl)hydrazinecarboxylate prepared, for example, from 1,1'-carbonyldiimidazole and tert-butoxy carbazate and the like. The reaction is generally performed in a general solvent such as dichloromethane, acetonitrile, tetrahydrofuran and N,N-dimethylformamide, or any other organic solvent that does not adversely influence the reaction, or a mixture thereof. The reaction temperature is not particularly important, and the reaction is performed under cooling or under heating. When necessary, deprotection is performed by an appropriate step to give the object compound.

The thus-produced compound (I) can be isolated or purified by a known separation or purification means such as crystallization, recrystallization, phase transition, chromatography and the like. In addition, it can be converted to a pharmaceutically acceptable salt.

The present invention is explained in more detail in the following by referring to Examples (Production Examples and Experimental Examples), which are not to be construed as limitative.

EXAMPLES

The starting material compounds used in the following Production Examples can be produced by a known method (WO 2004/067521, WO 2006/011631, WO 2006/028269, WO 2008/066145 etc.) or purchased as commercially available reagents.

Production Example 1

4-{2-[2-(acetylamino)-1,3-thiazol-4-yl]ethyl}phenyl hydrazinecarboxylate hydrochloride Step 1

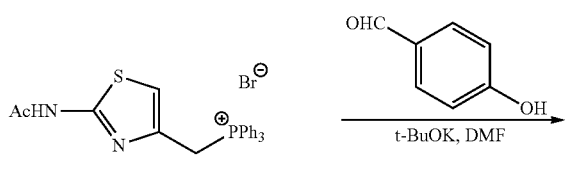

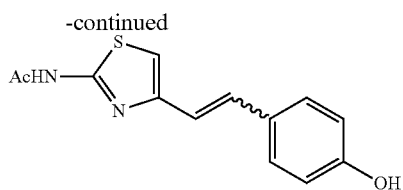

{[2-(Acetylamino)-1,3-thiazol-4-yl]methyl}(triphenyl)phosphoniumbromide (261.1 mg, 0.525 mmol) and 4-hydroxybenzaldehyde (183.2 mg, 1.50 mmol) were dissolved in anhydrous N,N-dimethylformamide (2 ml), and potassium tert-butoxide (56.1 mg, 0.50 mmol) was added at 0° C. After stirring at 90° C. for 12 hr, the mixture was cooled to room temperature. Water and ethyl acetate were added, and the mixture was stirred, stood still and then partitioned. The aqueous layer was extracted with ethyl acetate, and the combined organic layer was washed with saturated brine, dried over anhydrous magnesium sulfate and concentrated under reduced pressure. The concentrated residue was purified by silica gel column chromatography (FUJI SILYSIA CHEMICAL LTD. BW-300SP 25 g, ethyl acetate:hexane=4:6→5:5) to give N-{4-[2-(4-hydroxyphenyl)vinyl]-1,3-thiazol-2-yl}acetamide (87.9 mg, 0.338 mmol, yield 67.5%) as a white solid.

Step 2

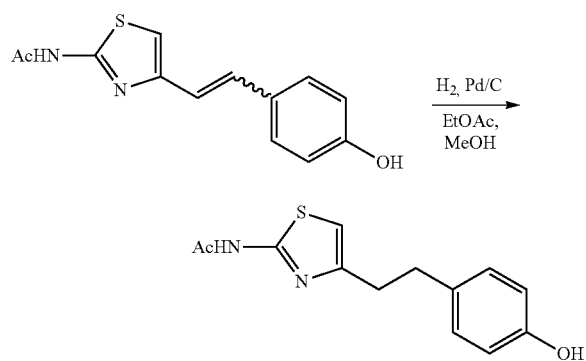

To a solution of N-{4-[2-(4-hydroxyphenyl)vinyl]-1,3-thiazol-2-yl}acetamide (932.3 mg, 3.58 mmol) in ethyl acetate (50 ml) was added 10% palladium carbon, and the mixture was hydrogenated at room temperature and atmospheric pressure. After the completion of the reaction, the reaction mixture was filtered through celite, and the filtrate was concentrated under reduced pressure. The residue was purified by silica gel column chromatography (FUJI SILYSIA CHEMICAL LTD. BW-300SP 30 g, dichloromethane:methanol=40:1→20:1) to give N-{4-[2-(4-hydroxyphenyl)ethyl]-1,3-thiazol-2-yl}acetamide (771.3 mg, 2.94 mmol, yield 82.1%) as a white solid.

Step 3

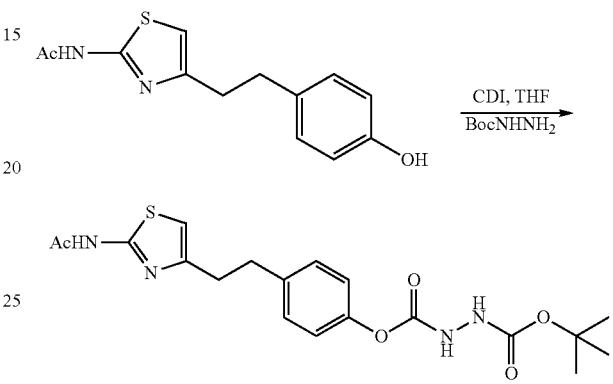

To a solution of N-{4-[2-(4-hydroxyphenyl)ethyl]-1,3-thiazol-2-yl}acetamide (655.8 mg, 2.50 mmol) in anhydrous tetrahydrofuran (12 ml) was added 1,1'-carbonyldiimidazole (608.1 mg, 3.75 mmol). After stirring at 45° C. for 1 hr, the mixture was cooled to room temperature. tert-Butyl carbazate (495.6 mg, 3.75 mmol) was added, and the mixture was stirred at room temperature for 15 hr. The reaction mixture was concentrated under reduced pressure, and the residue was purified by silica gel column chromatography (FUJI SILYSIA CHEMICAL LTD. BW-300SP 80 g, ethyl acetate:hexane=1:1→3:2) and chemically modified silica gel column chromatography (FUJI SILYSIA CHEMICAL LTD. DM-2035 45 g, dichloromethane:methanol=50:1→20:1) to give 4-{2-[2-(acetylamino)-1,3-thiazol-4-yl]ethyl}phenyl tert-butyl hydrazine-1,2-dicarboxylate (526.4 mg, 1.252 mmol, yield 50.0%) as a white solid.

Step 4

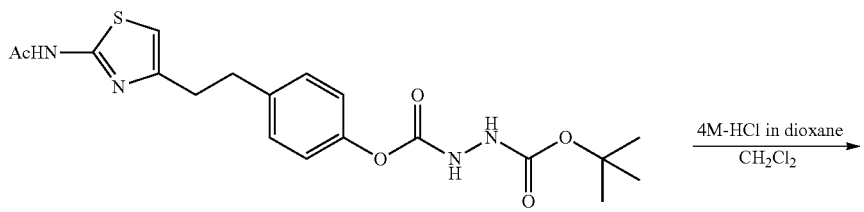

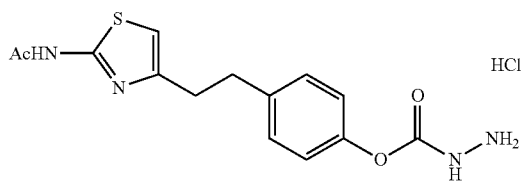

To a suspension of 4-{2-[2-(acetylamino)-1,3-thiazol-4-yl]ethyl}phenyl tert-butyl hydrazine-1,2-dicarboxylate (445.2 mg, 1.06 mmol) in anhydrous dichloromethane (5.3 ml) was added 4M hydrogen chloride dioxane solution (5.3 ml, 21.3 mmol). After stirring at room temperature for 2 hr, the reaction mixture was concentrated under reduced pressure. Ethyl acetate was added to the concentrated residue, and the mixture was concentrated again under reduced pressure. This operation was performed 3 times to remove hydrogen chloride gas azeotropically. The residue was suspended in ethyl acetate, and the solid was collected by filtration, washed twice with ethyl acetate, and dried under reduced pressure to give the title compound (380.5 mg, quantitative) as a white solid.

melting point: 167-169° C.

$^1$H-NMR (200 MHz, DMSO-d6): δ(ppm):12.11(1H, brs), 10.97(1H, brs), 7.25(2H, d, J=8.4 Hz), 7.06 (2H, d, J=8.4 Hz), 6.74(1H, s), 3.05-2.77(4H, m), 2.10(3H, s)

$^{13}$C-NMR (50 MHz, DMSO-d6): δ(ppm):168.5, 157.8, 154.4, 150.1, 148.4, 139.4, 129.6, 121.5, 107.7, 34.0, 32.9, 22.7

MS(ESI+):321.1018[M(free)+H]$^+$ anhydrous tetrahydrofuran (2.4 ml) was added 1,1'-carbonyldiimidazole (142.1 mg, 0.876 mmol), and the mixture was stirred at room temperature for 1.5 hr. tert-Butyl carbazate (115.9 mg, 0.877 mmol) was added, and the mixture was stirred for 16 hr. tert-Butyl carbazate (77.3 mg, 0.584 mmol) was added, and the mixture was stirred for 4 hr. tert-Butyl carbazate (77.3 mg, 0.584 mmol) was added again, and the mixture was stirred for 2 hr. tert-Butyl carbazate (115.9 mg, 0.877 mmol) was added again, and the mixture was stirred for 4 hr. The reaction mixture was concentrated under reduced pressure, and the residue was purified by silica gel column chromatography (FUJI SILYSIA CHEMICAL LTD. BW-300SP 10 g, ethyl acetate:hexane=5:5→6:4→7:3). The residue was further purified by silica gel column chromatography (FUJI SILYSIA CHEMICAL LTD. DM2035 5 g, ethyl acetate:hexane=5:5→1:0) to give 4-{2-[2-(acetylamino)-1,3-thiazol-4-yl]ethyl}benzyl tert-butyl hydrazine-1,2-dicarboxylate (207.0 mg, 0.476 mmol, yield 81.6%) as a white solid.

Step 2

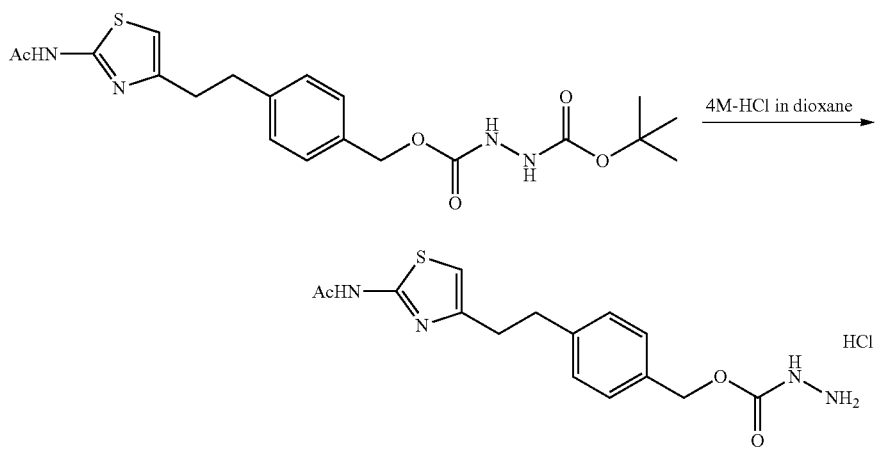

Production Example 2

4-{2-[2-(acetylamino)-1,3-thiazol-4-yl]ethyl}benzyl hydrazinecarboxylate hydrochloride Step 1

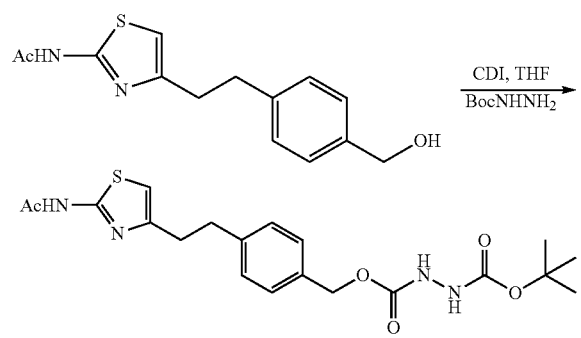

To a suspension of N-(4-{2-[4-(hydroxymethyl)phenyl]ethyl}-1,3-thiazol-2-yl)acetamide (161.5 mg, 0.584 mmol) in To a suspension of 4-{2-[2-(acetylamino)-1,3-thiazol-4-yl]ethyl}benzyl tert-butyl hydrazine-1,2-dicarboxylate (203.0 mg, 0.467 mmol) in anhydrous dichloromethane (2.3 ml) was added 4M hydrogen chloride dioxane solution (2.3 ml, 9.2 mmol). After stirring at room temperature for 2.5 hr, the mixture was concentrated under reduced pressure. Ethyl acetate was added to the concentrated residue, and the mixture was concentrated again under reduced pressure. This operation was performed 3 times to remove hydrogen chloride gas azeotropically. The residue was suspended in ethyl acetate and filtered. The filtered product was washed with ethyl acetate and dried under reduced pressure to give the title compound (179.3 mg, quantitative) as a white solid.

melting point 162-164° C.

$^1$H-NMR (200 MHz, DMSO-d6): δ(ppm):12.06(1H, brs), 10.25(3H, br), 7.29(2H, d, J=8.2 Hz), 7.20(2H, d, J=8.2 Hz), 6.71(1H, s), 5.13(2H, s), 3.00-2.78(4H, m), 2.10(3H, s)

$^{13}$C-NMR (50 MHz, DMSO-d6): δ(ppm):168.5, 157.7, 155.8, 150.2, 141.8, 133.5, 128.6, 128.5, 107.7, 67.2, 34.4, 32.8, 22.7

MS(ESI+):357.0965[M(free)+Na]$^+$

Production Example 3

2-(4-{2-[2-(acetylamino)-1,3-thiazol-4-yl]ethyl}phenyl)ethyl hydrazinecarboxylate hydrochloride Step 1

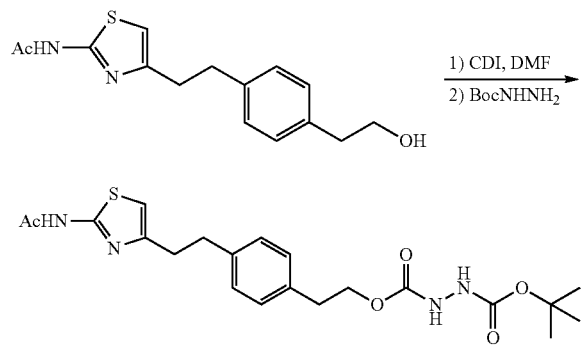

To a suspension of N-(4-{2-[4-(2-hydroxyethyl)phenyl]ethyl}-1,3-thiazol-2-yl)acetamide (552.5 mg, 1.799 mmol) in anhydrous tetrahydrofuran (8 ml) was added 1,1'-carbonyldiimidazole (437.8 mg, 2.700 mmol), and the mixture was stirred at 45° C. for 0.5 hr. tert-Butyl carbazate (356.8 mg, 2.700 mmol) was added. After stirring for 1 hr, tert-butyl carbazate (356.6 mg, 2.698 mmol) was added. After stirring for 3 hr, tert-butyl carbazate (357.0 mg, 2.701 mmol) was further added. After stirring for 24 hr, the mixture was concentrated under reduced pressure, and the residue was purified by silica gel column chromatography (FUJI SILYSIA CHEMICAL LTD. DM1025 60 g, ethyl acetate:hexane=5:5→7:3). The residue was further purified by silica gel column chromatography (Sep pak-5 g, ethyl acetate:hexane=7:3) to give 2-(4-{2-[2-(acetylamino)-1,3-thiazol-4-yl]ethyl} phenyl)ethyl tert-butyl hydrazine-1,2-dicarboxylate (755.9 mg, 1.685 mmol, yield 93.6%) as white crystals.

Step 2

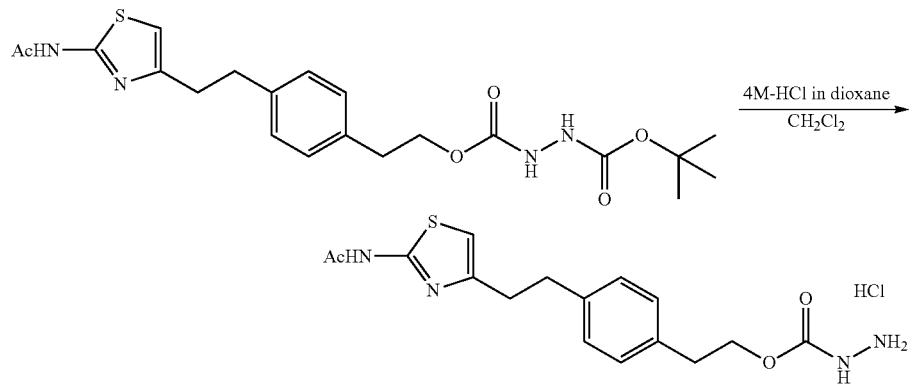

To a suspension of 2-(4-{2-[2-(acetylamino)-1,3-thiazol-4-yl]ethyl}phenyl)ethyl tert-butyl hydrazine-1,2-dicarboxylate (620.0 mg, 1.382 mmol) in anhydrous dichloromethane (6.9 ml) was added 4M hydrogen chloride dioxane solution (6.9 ml, 27.6 mmol). After stirring at room temperature for 13 hr, the reaction mixture was concentrated under reduced pressure. Dichloromethane was added to the residue, and the mixture was concentrated again under reduced pressure. The operation was performed twice. Ethyl acetate was further added to the residue, and the mixture was concentrated under reduced pressure. This operation was performed 3 times to remove hydrogen chloride gas azeotropically. The residue was dried under reduced pressure to give a crude product (570.4 mg). The crude product was dissolved in methanol (18 ml) and ethyl acetate (144 ml) was added to recrystallize the crude product. The crystals were collected by filtration, washed with ethyl acetate, and dried under reduced pressure to give the title compound (474.8 mg, 1.234 mmol, yield 89.3%) as a white solid.

melting point 172-174° C.

$^1$H-NMR (200 MHz, DMSO-d6): δ(ppm):12.09(1H, brs), 11.0-9.6(3H, br), 7.25-6.95(4H, m), 6.74(1H, s), 4.27(2H, t, J=6.7 Hz), 3.01-2.68(6H, m), 2.11(3H, s)

$^{13}$C-NMR (50 MHz, DMSO-d6): δ (ppm): 168.5, 157.8, 155.9, 150.2, 139.7, 135.3, 129.1, 128.5, 107.6, 66.5, 34.3, 32.9, 22.7

MS(ESI+):349.1332[M(free)+H]$^+$, 371.1147[M(free)+Na]$^+$

Production Example 4

4-{2-[2-(acetylamino)-1,3-thiazol-4-yl]ethyl}-2-fluorobenzyl hydrazinecarboxylate hydrochloride Step 1

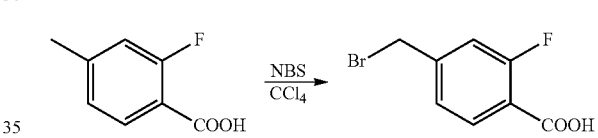

To a solution of 2-fluoro-4-methylbenzoic acid (1.029 g, 6.678 mmol) in carbon tetrachloride (10 ml) were added N-bromosuccinimide (1.189 g, 6.682 mmol) and 2,2'-azobisisobutyronitrile (43.9 mg, 0.267 mmol). After stirring at 90° C. for 30 min and at 100° C. for 2.5 hr, the mixture was cooled to 0° C. The precipitate was collected by filtration and washed with hexane and water to give a crude product. The crude product was dissolved in ethyl acetate (5 ml), and hexane (10 ml) was added. The precipitated solid was collected by filtration, and dried under reduced pressure to give 4-(bromomethyl)-2-fluorobenzoic acid (838.6 mg, 3.599 mmol, yield 53.9%) as a slightly yellow solid.

Step 2

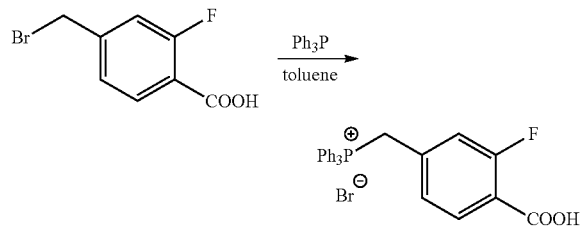

To a suspension of 4-(bromomethyl)-2-fluorobenzoic acid (914.2 mg, 3.923 mmol) in toluene (20 ml) was added triphenylphosphine (1.029 g, 3.923 mmol). After heating the mixture under reflux for 6 hr, the reaction mixture was cooled to room temperature. The precipitate was collected by filtration, and dried under reduced pressure to give (4-carboxy-3-fluorobenzyl)(triphenyl)phosphoniumbromide (2.057 g, quantitative) as a white solid.

Step 3

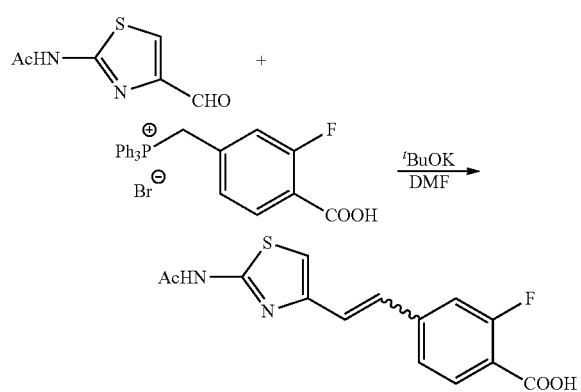

To a solution of (4-carboxy-3-fluorobenzyl)(triphenyl) phosphoniumbromide (2.037 g, 4.112 mmol) and N-(4-formyl-1,3-thiazol-2-yl)acetamide (599.5 mg, 3.523 mmol) in anhydrous N,N-dimethylformamide (15 ml) was added potassium tert-butoxide (1.180 g, 10.52 mmol), and the mixture was stirred at room temperature for 3 hr. Water (150 ml) was added to the reaction mixture, and the mixture was washed 3 times with ethyl acetate. While stirring, 1M hydrochloric acid (10.5 ml) was added to the aqueous layer. The precipitated solid was collected by filtration and washed with water. The solid was dried under reduced pressure to give 4-{2-[2-(acetylamino)-1,3-thiazol-4-yl]vinyl}-2-fluorobenzoic acid (753.9 mg, 2.461 mmol, yield 69.9%) as a yellow solid.

Step 4

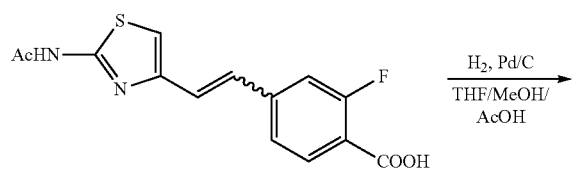

-continued

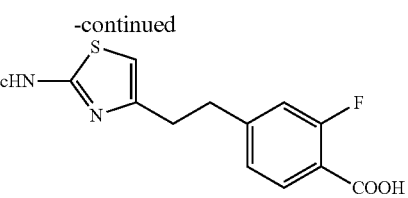

To a mixed solution of 4-{2-[2-(acetylamino)-1,3-thiazol-4-yl]vinyl}-2-fluorobenzoic acid (738.9 mg, 2.412 mmol) in tetrahydrofuran (105 ml), methanol (105 ml) and acetic acid (21 ml) was added 10% palladium carbon (593.0 mg, containing 50% water), and the mixture was hydrogenated at room temperature and atmospheric pressure. The reaction mixture was filtered through celite and the filtrate was concentrated under reduced pressure. The resulting solid was collected by filtration, washed with diisopropyl ether, and dried under reduced pressure to give 4-{2-[2-(acetylamino)-1,3-thiazol-4-yl]ethyl}-2-fluorobenzoic acid (576.2 mg, 1.869 mmol, yield 77.5%) as a white solid.

Step 5

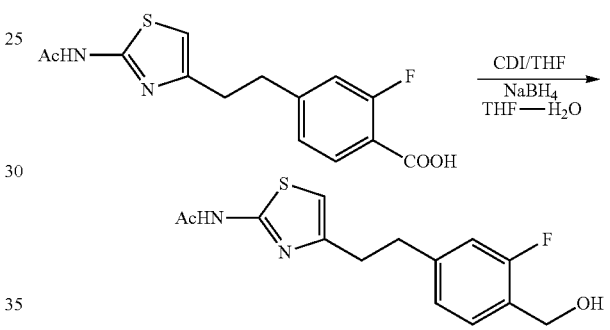

To a suspension of 4-{2-[2-(acetylamino)-1,3-thiazol-4-yl]ethyl}-2-fluorobenzoic acid (555.0 mg, 1.800 mmol) in anhydrous tetrahydrofuran (4 ml) was added 1,1'-carbonyldiimidazole (364.8 mg, 2.250 mmol), and the mixture was stirred at room temperature for 1.5 hr. The reaction mixture was added dropwise to a mixture of sodium borohydride (1.362 g, 36.0 mmol), tetrahydrofuran (36 ml) and water (9 ml), which had been cooled to −25° C. After stirring at not more than 0° C. for 1 hr, water was added to the reaction mixture, and the mixture was extracted twice with ethyl acetate. The combined organic layer was washed with 1M hydrochloric acid, saturated aqueous sodium hydrogen carbonate and saturated brine, and dried over anhydrous magnesium sulfate. The organic layer was concentrated under reduced pressure, and a mixture of methanol (0.5 ml) and diisopropyl ether (15 ml) was added to the residue. The precipitate was collected by filtration and dried under reduced pressure to give N-(4-{2-[3-fluoro-4-(hydroxymethyl)phenyl]ethyl}-1,3-thiazol-2-yl)acetamide (342.8 mg, 1.165 mmol, yield 64.7%) as a white solid.

Step 6

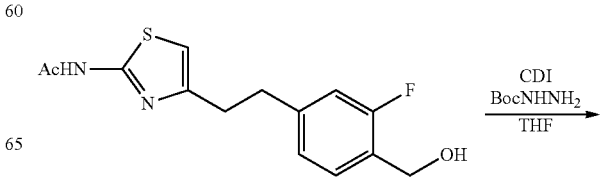

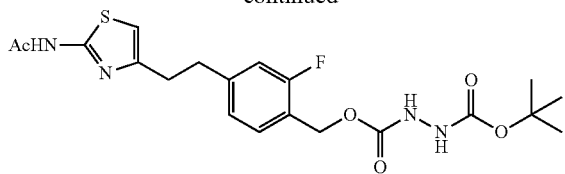

To a suspension of N-(4-{2-[3-fluoro-4-(hydroxymethyl)phenyl]ethyl}-1,3-thiazol-2-yl)acetamide (118.8 mg, 0.4036 mmol) in anhydrous tetrahydrofuran (1.5 ml) was added 1,1'-carbonyldiimidazole (98.1 mg, 0.605 mmol), and the mixture was stirred at room temperature for 2.5 hr. tert-Butyl carbazate (160.3 mg, 1.213 mmol) was added, and the mixture was stirred at room temperature for 20 hr. Water, 1M hydrochloric acid and ethyl acetate were added, and the mixture was stirred, stood still and then partitioned. The organic layer was washed twice with water, and washed with saturated brine. After drying over anhydrous magnesium sulfate, the residue was concentrated under reduced pressure. The residue was suspended in dichloromethane (15 ml) and filtered. After washing with dichloromethane, the residue was dried under reduced pressure and purified by silica gel column chromatography (FUJI SILYSIA CHEMICAL LTD. BW-300SP 12 g, ethyl acetate:hexane=1:1). The fractions containing the object product were concentrated to give a solid, which was suspended in a mixture of tert-butyl methyl ether (5 ml) and hexane (5 ml) and filtered. The filtered product was dried under reduced pressure to give 4-{2-[2-(acetylamino)-1,3-thiazol-4-yl]ethyl}-2-fluorobenzyl tert-butyl hydrazine-1,2-dicarboxylate (153.7 mg, 0.340 mmol, yield 84.2%) as a white solid.

Step 7

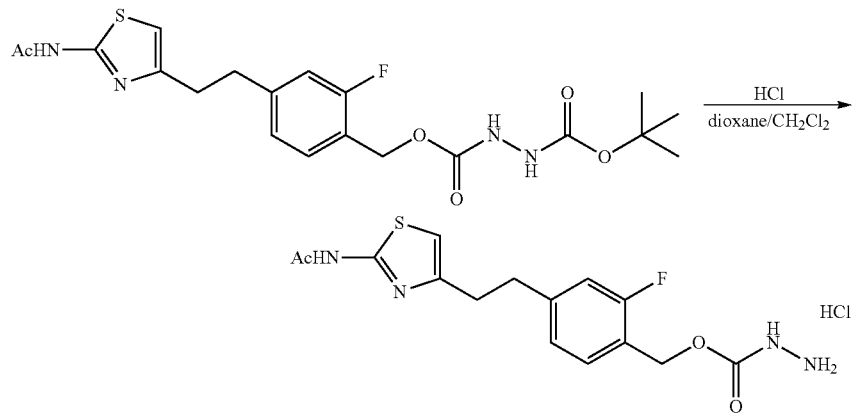

To a suspension of 4-{2-[2-(acetylamino)-1,3-thiazol-4-yl]ethyl}-2-fluorobenzyl tert-butyl hydrazine-1,2-dicarboxylate (147.0 mg, 0.325 mmol) in anhydrous dichloromethane (2 ml) was added 4M hydrogen chloride dioxane solution (2 ml). After stirring at room temperature for 2 hr, and the mixture was concentrated under reduced pressure. Ethyl acetate was added to the concentrated residue, and the mixture was concentrated again under reduced pressure. This operation was performed 3 times to remove hydrogen chloride gas azeotropically. The residue was suspended in a mixture of ethanol (2 ml) and ethyl acetate (8 ml) and filtered. The filtered product was washed twice with ethyl acetate, and dried under reduced pressure to give 4-{2-[2-(acetylamino)-1,3-thiazol-4-yl]ethyl}-2-fluorobenzyl hydrazinecarboxylate hydrochloride (129.1 mg, quantitative) as a white solid.

melting point 162-165° C.

$^1$H-NMR (400 MHz, DMSO-d6): δ (ppm):12.07(1H, brs), 10.5-9.8(2H, br), 10.28(1H, brs), 7.38(1H, t, J=7.9 Hz), 7.11 (1H, J=11.1 Hz), 7.06(1H, dd, J=7.9, 1.4 Hz), 6.74(1H, s), 5.19(2H, s), 2.99-2.87(4H, m), 2.12(3H, s)

$^{13}$C-NMR (100 MHz, DMSO-d6): δ (ppm):168.2, 160.3(d, J=246.9 Hz), 157.4, 155.4, 149.7, 145.1(d, J=8.2 Hz), 131.0 (d, J=4.5 Hz), 124.3(d, J=3.0 Hz), 119.8(d, J=15.0 Hz), 115.1 (d, J=21.0 Hz), 107.5, 61.2, 33.8, 32.1, 22.4

$^{19}$F-NMR (376 Hz, DMSO-d6): δ (ppm): −120.9

MS(ESI+):353.1037[M(free)+H]$^+$, 375.0859[M(free)+Na]$^+$

Production Example 5

4-{2-[2-(acetylamino)-1,3-thiazol-4-yl]ethyl}-3-fluorobenzyl hydrazinecarboxylate hydrochloride Step 1

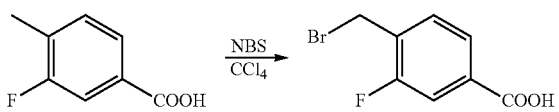

3-Fluoro-4-methylbenzoic acid (2.541 g, 16.49 mmol) was brominated by a method similar to that of Production Example 4, step 1 to give 4-(bromomethyl)-3-fluorobenzoic acid (2.539 g, 10.90 mmol, yield 66.1%) as a white solid.

Step 2

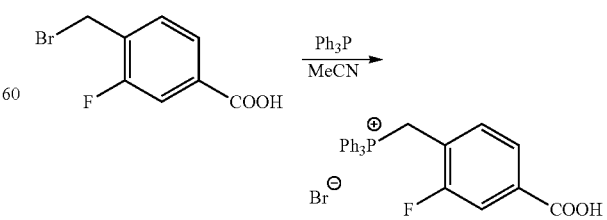

In a similar manner as in Production Example 4, step 2, (4-carboxy-3-fluorobenzyl)(triphenyl)phosphoniumbromide (4.130 g, 8.338 mmol, yield 76.9%) was obtained as a white solid from 4-(bromomethyl)-3-fluorobenzoic acid (2.526 g, 10.84 mmol).

Step 3

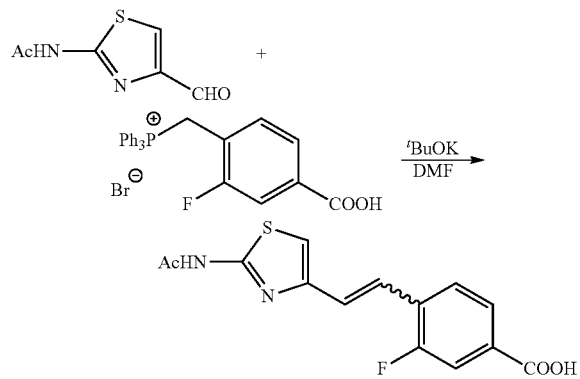

N-(4-Formyl-1,3-thiazol-2-yl)acetamide (941.7 mg, 5.533 mmol) and (4-carboxy-3-fluorobenzyl)(triphenyl)phosphoniumbromide (4.111 g, 8.300 mmol) were condensed by a method similar to that of Production Example 4, step 3, to give 4-{2-[2-(acetylamino)-1,3-thiazol-4-yl]vinyl}-3-fluorobenzoic acid (1.086 g, 3.547 mmol, yield 64.1%) as a pale-yellow solid.

Step 4

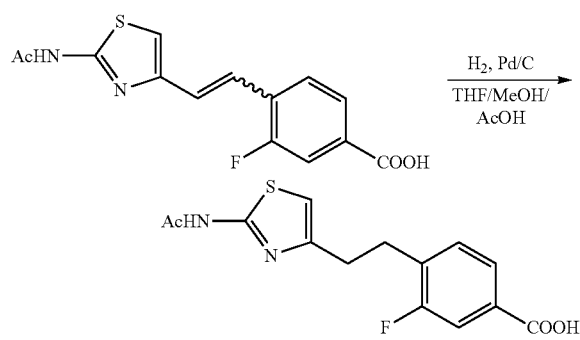

4-{2-[2-(Acetylamino)-1,3-thiazol-4-yl]vinyl}-3-fluorobenzoic acid (1.000 g, 3.265 mmol) was hydrogenated by a method similar to that of Production Example 4, step 4, to give 4-{2-[2-(acetylamino)-1,3-thiazol-4-yl]ethyl}-3-fluorobenzoic acid (620.0 mg, 2.011 mmol, yield 61.7%) as a pale-yellow solid.

Step 5

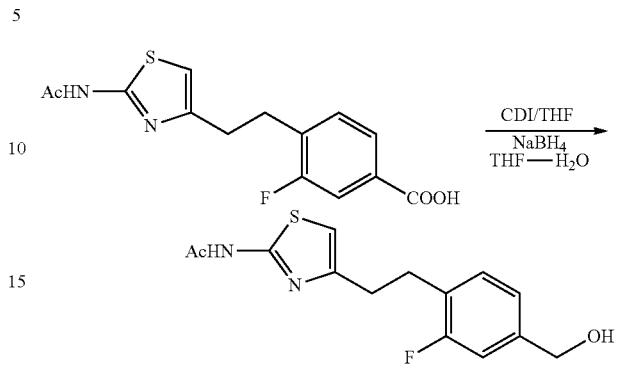

4-{2-[2-(Acetylamino)-1,3-thiazol-4-yl]ethyl}-3-fluorobenzoic acid (593.4 mg, 1.924 mmol) was reduced by a method similar to that of Production Example 4, step 5, to give N-(4-{2-[2-fluoro-4-(hydroxymethyl)phenyl]ethyl}-1,3-thiazol-2-yl)acetamide (406.9 mg, 1.382 mmol, yield 71.8%) as a white solid.

Step 6

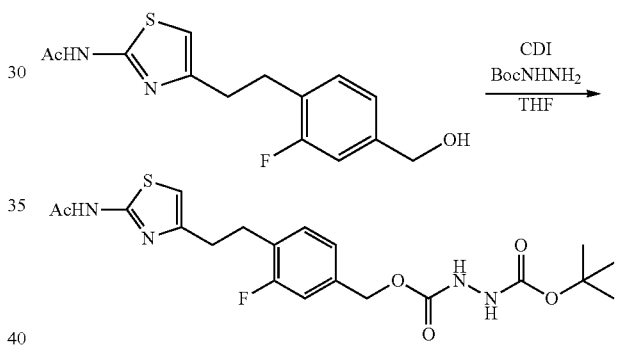

In a similar manner as in Production Example 4, step 6, 4-{2-[2-(acetylamino)-1,3-thiazol-4-yl]ethyl}-3-fluorobenzyl tert-butyl hydrazine-1,2-dicarboxylate (196.0 mg, 0.433 mmol, yield 66.7%) was obtained as a pale-yellow solid from N-(4-{2-[2-fluoro-4-(hydroxymethyl)phenyl]ethyl}-1,3-thiazol-2-yl)acetamide (191.0 mg, 0.649 mmol).

Step 7

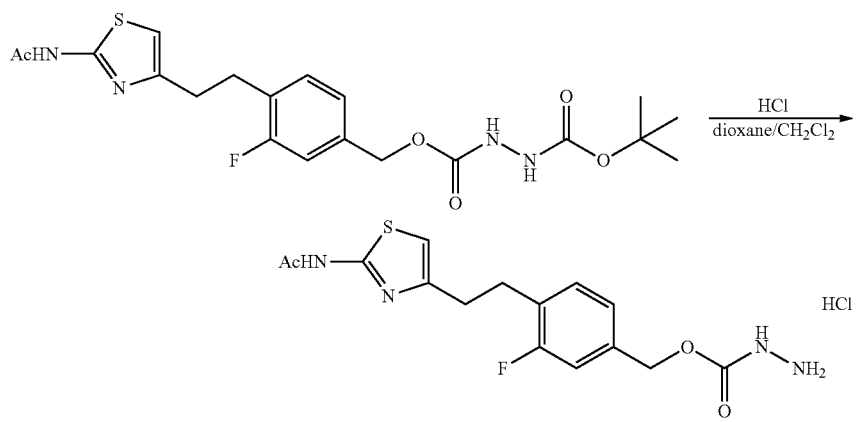

4-{2-[2-(Acetylamino)-1,3-thiazol-4-yl]ethyl}-3-fluorobenzyl tert-butyl hydrazine-1,2-dicarboxylate (154.0 mg, 0.341 mmol) was deprotected by a method similar to that of Production Example 4, step 7 to give the title compound (123.0 mg, 0.316 mmol, yield 92.9%) as a white solid.

melting point 204-208° C.

$^1$H-NMR (400 MHz, DMSO-d6): δ (ppm):12.09(1H, brs), 10.43(3H, bs), 7.27(1H, t, J=8.0 Hz), 7.17(1H, d, J=10.4 Hz), 7.14(1H, t, J=8.0 Hz), 6.74(1H, s), 5.14(2H, s), 2.97-2.82(4H, m), 2.10(3H, s)

$^{13}$C-NMR (100 MHz, DMSO-d6): δ (ppm):168.4, 160.5(d, J=24.2 Hz), 157.7, 149.9, 136.3(d, J=7.4 Hz), 131.0, 128.0(d, J=14.9 Hz), 124.0, 114.8(d, J=14.9 Hz), 107.7, 66.3, 31.5, 27.8, 22.6

MS(ESI+):353.1075[M(free)+H]$^+$, 375.0895[M(free)+Na]$^+$

Production Example 6

4-{2-[2-(acetylamino)-1,3-thiazol-4-yl]ethyl}-2,3-difluorobenzyl hydrazinecarboxylate hydrochloride Step 1

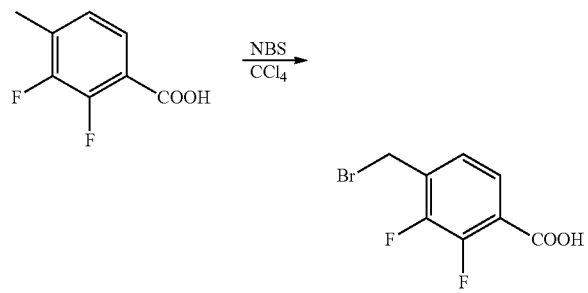

2,3-Difluoro-4-methylbenzoic acid (4.689 g, 27.24 mmol) was brominated by a method similar to that of Production Example 4, step 1 to give 4-(bromomethyl)-2,3-difluorobenzoic acid (1.724 g, 6.869 mmol, yield 25.2%) as a slightly yellow solid.

Step 2

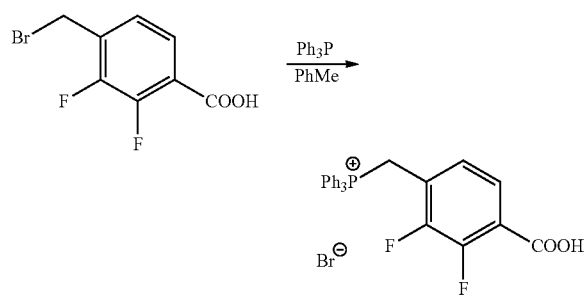

In a similar manner as in Production Example 4, step 2, (4-carboxy-2,3-difluorobenzyl)(triphenyl)phosphoniumbromide (3.246 g, 6.323 mmol, yield 95.2%) was obtained as a white solid from 4-(bromomethyl)-2,3-difluorobenzoic acid (1.667 g, 6.640 mmol).

Step 3

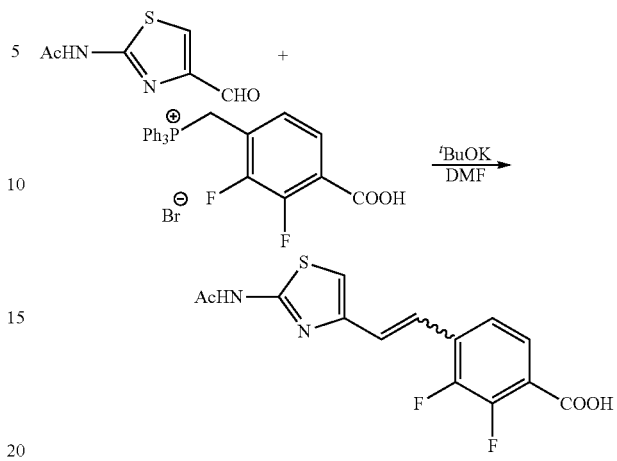

N-(4-Formyl-1,3-thiazol-2-yl)acetamide (1.071 g, 6.292 mmol) and (4-carboxy-2,3-difluorobenzyl)(triphenyl)phosphoniumbromide (3.227 g, 6.287 mmol) were condensed by a method similar to that of Production Example 4, step 3, to give 4-{2-[2-(acetylamino)-1,3-thiazol-4-yl]vinyl}-2,3-difluorobenzoic acid (1.550 g, 4.778 mmol, yield 76.0%) as a yellow solid.

Step 4

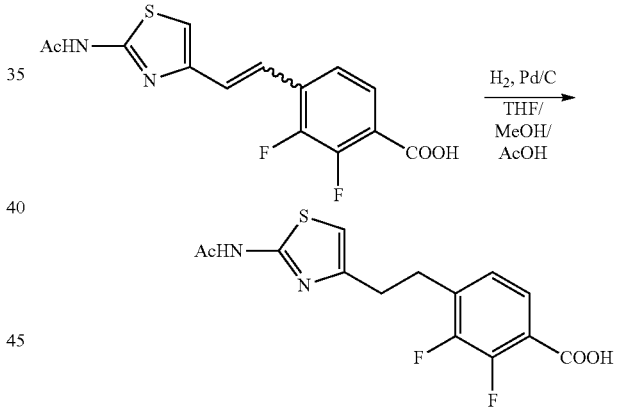

4-{2-[2-(Acetylamino)-1,3-thiazol-4-yl]vinyl}-2,3-difluorobenzoic acid (1.533 g, 4.728 mmol) was hydrogenated by a method similar to that of Production Example 4, step 4 to give 4-{2-[2-(acetylamino)-1,3-thiazol-4-yl]ethyl}-2,3-difluorobenzoic acid (1.325 g, 4.059 mmol, yield 85.8%) as a pale-yellow solid.

Step 5

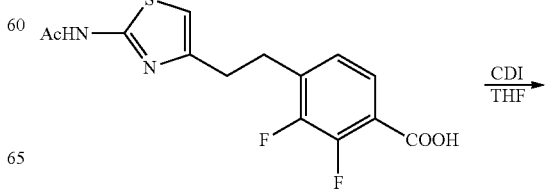

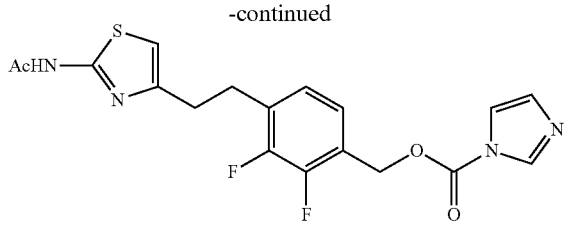

To a suspension of 4-{2-[2-(acetylamino)-1,3-thiazol-4-yl]ethyl}-2,3-difluorobenzoic acid (654.0 mg, 2.004 mmol) in anhydrous tetrahydrofuran (5 ml) was added 1,1'-carbonyldiimidazole (408.2 mg, 2.517 mmol), and the mixture was stirred at room temperature for 2.5 hr. 1,1'-Carbonyldiimidazole (61.0 mg, 0.376 mmol) was added, and the mixture was stirred at room temperature for 0.5 hr. The reaction mixture was concentrated under reduced pressure, and the precipitate was suspended in ethyl acetate (10 ml) and filtered. The filtered product was dried under reduced pressure to give N-(4-{2-[2,3-difluoro-4-(1H-imidazol-1-ylcarbonyl)phenyl]ethyl}-1,3-thiazol-2-yl)acetamide (516.0 mg, 1.371 mmol, yield 68.4%) as a white solid.

Step 6

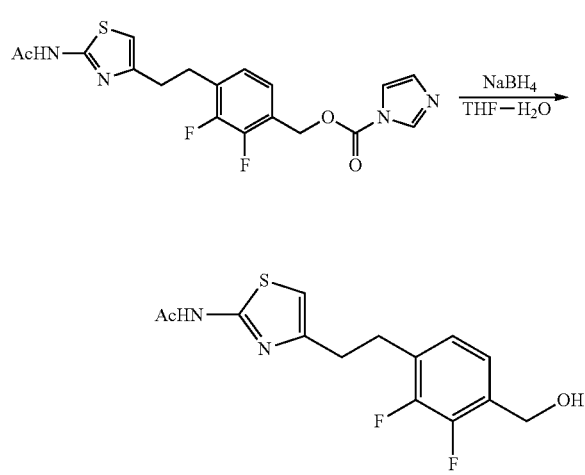

Sodium borohydride (1.009 g, 26.66 mmol) was suspended in a mixture of tetrahydrofuran (36 ml) and water (9 ml), and the suspension was cooled to −20° C. A suspension of N-(4-{2-[2,3-difluoro-4-(1H-imidazol-1-ylcarbonyl)phenyl]ethyl}-1,3-thiazol-2-yl)acetamide (503.5 mg, 1.338 mmol) in anhydrous tetrahydrofuran (4 ml) was added dropwise. After stirring at not more than 0° C. for 2.5 hr, saturated aqueous ammonium chloride (50 ml) was added. The mixture was extracted 3 times with ethyl acetate, and the combined organic layer was washed with saturated aqueous ammonium chloride and saturated brine. The organic layer was dried over anhydrous magnesium sulfate and concentrated under reduced pressure. To the residue were added methanol (0.5 ml) and diisopropyl ether (25 ml), and the mixture was stirred and filtered. The filtered product was dried under reduced pressure to give N-(4-{2-[2,3-difluoro-4-(hydroxymethyl)phenyl]ethyl}-1,3-thiazol-2-yl)acetamide (316.8 mg, 1.014 mmol, 75.8%) as a white solid.

Step 7

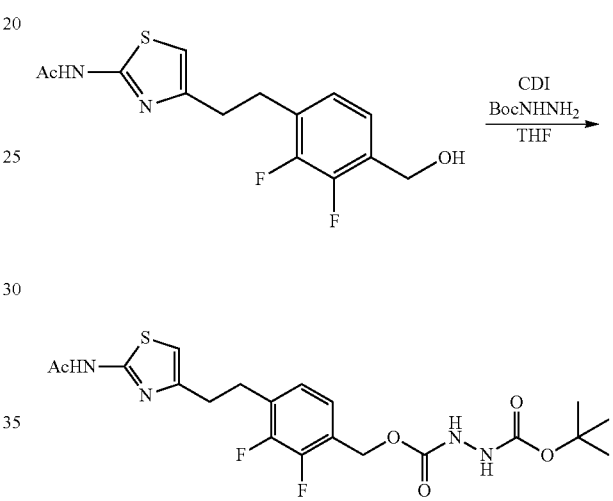

In a similar manner as in Production Example 4, step 6, 4-{2-[2-(acetylamino)-1,3-thiazol-4-yl]ethyl}-2,3-difluorobenzyl tert-butyl hydrazine-1,2-dicarboxylate (173.4 mg, 0.369 mmol, yield 92.3%) was obtained as a white solid from N-(4-{2-[2,3-difluoro-4-(hydroxymethyl)phenyl]ethyl}-1,3-thiazol-2-yl)acetamide (125.0 mg, 0.400 mmol).

Step 8

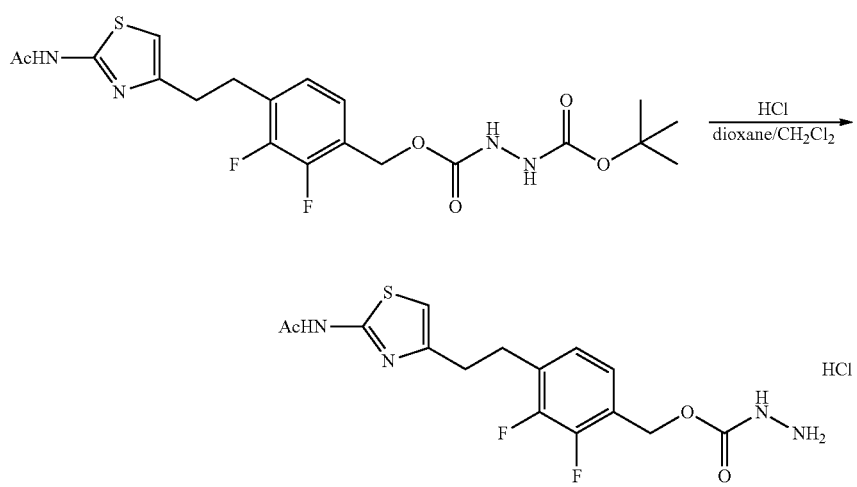

4-{2-[2-(Acetylamino)-1,3-thiazol-4-yl]ethyl}-2,3-difluorobenzyl tert-butyl hydrazine-1,2-dicarboxylate (164.8 mg, 0.350 mmol) was deprotected by a method similar to that of Production Example 4, step 7, to give the title compound (145.2 mg, quantitative) as a white solid.

melting point 154-160° C.

$^1$H-NMR (400 MHz, DMSO-d6): δ (ppm):12.10(1H, brs), 10.41(4H, brs), 7.22(1H, t, J=7.3 Hz), 7.12(1H, t, J=7.3 Hz), 6.76(1H, s), 5.23(2H, s), 3.03-2.87(4H, m), 2.12(3H, s)

$^{13}$C-NMR (100 MHz, DMSO-d6): δ (ppm):168.2, 157.5, 155.2, 149.3, 148.1(dd, J=248.7, 12.6 Hz), 147.9(dd, J=244.6, 11.9 Hz), 131.0(d, J=12.8 Hz), 125.2, 125.1, 122.6 (d, J=12.0 Hz), 107.7, 60.7, 30.9, 27.5, 22.4

$^{19}$F-NMR (376 Hz, DMSO-d6): δ (ppm):−144.8(1F, d, $J_{FF}$=19.1 Hz), −145.9(1F, d, $J_{FF}$=19.1 Hz)

MS(ESI+):371.0950[M(free)+H]$^+$, 393.0768[M(free)+Na]$^+$

Production Example 7

2-(4-{[2-(acetylamino)-1,3-thiazol-4-yl]methoxy}phenyl)ethyl hydrazinecarboxylate Step 1

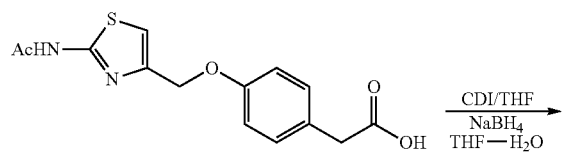

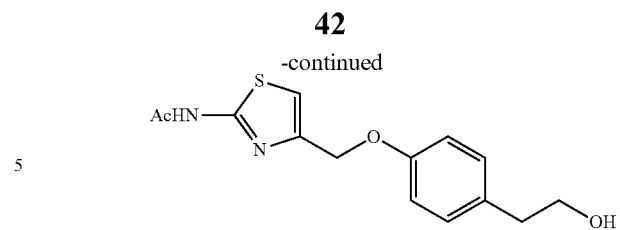

(4-{[2-(Acetylamino)-1,3-thiazol-4-yl]methoxy}phenyl)acetic acid (644.0 mg, 2.102 mmol) was reduced by a method similar to that of Production Example 4, step 5, to give N-(4-{[4-(2-hydroxyethyl)phenoxy]methyl}-1,3-thiazol-2-yl)acetamide (577.6 mg, 1.976 mmol, yield 94.0%) as a white solid.

Step 2

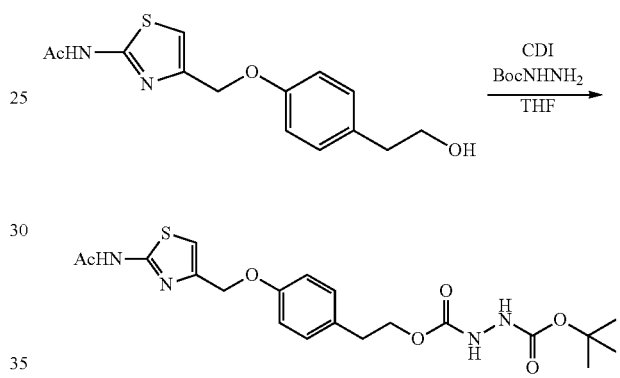

In a similar manner as in Production Example 4, step 6, 2-(4{[2-(acetylamino)-1,3-thiazol-4-yl]methoxy}phenyl)ethyl tert-butyl hydrazine-1,2-dicarboxylate (479.4 mg, quantitative) was obtained as a white solid from N-(4-{[4-(2-hydroxyethyl)phenoxy]methyl}-1,3-thiazol-2-yl)acetamide (250.0 mg, 0.855 mmol).

Step 3

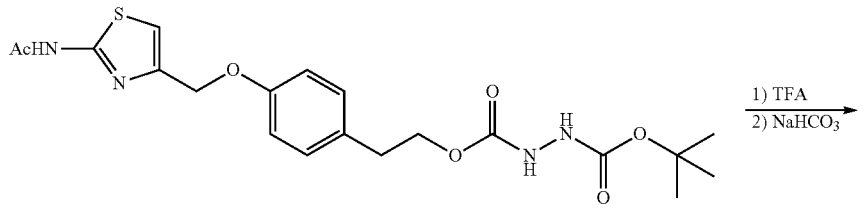

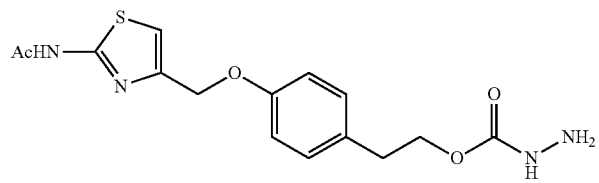

To a solution of 2-(4{[2-(acetylamino)-1,3-thiazol-4-yl]methoxy}phenyl)ethyl tert-butyl hydrazine-1,2-dicarboxylate (0.855 mmol) in dichloromethane (30 ml) was added trifluoroacetic acid (3.18 ml, 42.8 mmol) at 0° C. After stirring at 0° C. for 30 min, the mixture was stirred at room temperature for 1 hr. The reaction mixture was concentrated, aqueous sodium hydrogen carbonate solution was added to the residue, and the mixture was extracted 4 times with ethyl acetate. The combined organic layer was washed with saturated aqueous sodium hydrogen carbonate solution and saturated brine, dried over anhydrous magnesium sulfate and concentrated under reduced pressure. Ethyl acetate (20 ml) was added to suspend the residue. The suspension was filtered and washed once with ethyl acetate and 5 times with diethyl ether, and dried under reduced pressure to give the title compound (105.9 mg, 0.302 mmol, yield 35.3%) as a white solid.

melting point 177-180° C.

$^1$H-NMR (400 MHz, DMSO-d6): δ (ppm):12.13(1H, brs), 8.09(1H, brs), 7.16(1H, s),7.14(2H, d, J=8.6 Hz), 6.92(2H, d, J=8.6 Hz), 5.00(2H, s), 4.10(2H, t, J=6.9 Hz), 3.99(2H, brs), 2.77(2H, t, J=6.9 Hz), 2.12(3H, s)

$^{13}$C-NMR (100 MHz, DMSO-d6): δ (ppm):168.6, 158.2, 156.9, 146.6, 130.4, 130.0, 114.8, 111.4, 65.6, 64.9, 34.2, 22.6

MS(ESI+):351.1090[M+H]$^+$, 373.0911[M+Na]$^+$

Production Example 8

4-{2-[(hydrazinocarbonyl)oxy]ethyl}phenyl 2-(acetylamino)-1,3-thiazole-4-carboxylate hydrochloride Step 1

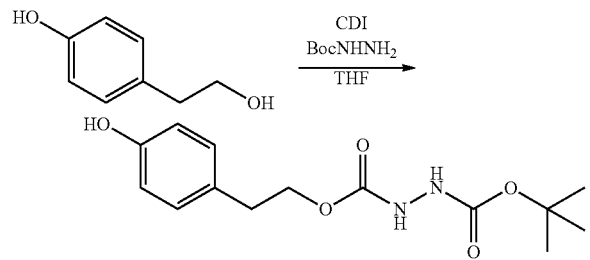

To a suspension of 1,1'-carbonyldiimidazole (1.620 g, 9.989 mmol) in anhydrous tetrahydrofuran (20 ml) was added 2-(4-hydroxyphenyl)ethanol (1.383 g, 10.01 mmol), and the mixture was stirred at room temperature for 3 hr. tert-Butyl carbazate (1.323 g, 10.01 mmol) was added, and the mixture was stirred at room temperature for 1.5 hr. Water (100 ml) and ethyl acetate (100 ml) were added to the reaction mixture, and the mixture was stirred, stood still and then partitioned. The aqueous layer was extracted with ethyl acetate, and the combined organic layer was washed with saturated brine, dried over anhydrous magnesium sulfate and concentrated under reduced pressure, and the residue was purified by silica gel column chromatography (FUJI SILYSIA CHEMICAL LTD. BW-300SP 40 g, ethyl acetate:hexane=4:6→5:5). The fractions containing the object product were concentrated under reduced pressure, and the obtained solid was suspended in diisopropyl ether (50 ml) and filtered. The filtered product was washed 3 times with diisopropyl ether and dried under reduced pressure to give tert-butyl 2-(4-hydroxyphenyl)ethyl hydrazine-1,2-dicarboxylate (616.7 mg, 2.08 mmol, yield 20.8%) as a white solid.

Step 2

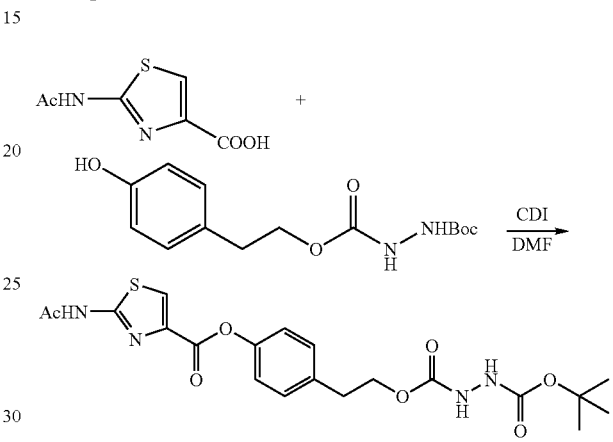

To a suspension of 2-(acetylamino)-1,3-thiazole-4-carboxylic acid (466.2 mg, 2.504 mmol) in anhydrous N,N-dimethylformamide (5 ml) was added 1,1'-carbonyldiimidazole (405.7 mg, 2.502 mmol), and the mixture was stirred at 50° C. for 2.5 hr. tert-Butyl 2-(4-hydroxyphenyl)ethyl hydrazine-1,2-dicarboxylate (594.8 mg, 2.001 mmol) was added, and the mixture was stirred at 50° C. for 18 hr. Water (40 ml) and ethyl acetate (40 ml) were added to the reaction mixture and the mixture was stirred, stood still and then partitioned. The organic layer was washed with water and saturated brine, dried over anhydrous magnesium sulfate and concentrated under reduced pressure. The residue was purified by silica gel column chromatography (FUJI SILYSIA CHEMICAL LTD. BW-300SP 40 g, hexane:ethyl acetate=6:4→5:5). The fractions containing the object product were concentrated under reduced pressure and the obtained solid was suspended in a mixture of hexane (40 ml) and tert-butyl methyl ether (20 ml). The suspension was filtered and dried under reduced pressure to give 2-[4-({[2-(acetylamino)-1,3-thiazol-4-yl]carbonyl}oxy)phenyl]ethyl tert-butyl hydrazine-1,2-dicarboxylate (539.2 mg, 1.161 mmol, yield 58.0%) as a white solid.

Step 3

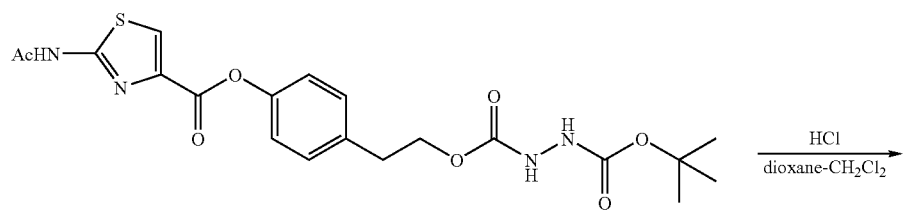

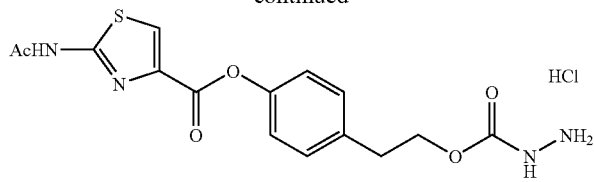

To a suspension of 2-[4-({[2-(acetylamino)-1,3-thiazol-4-yl]carbonyl}oxy)phenyl]ethyl tert-butyl hydrazine-1,2-dicarboxylate (371.6 mg, 0.800 mmol) in anhydrous dichloromethane (4 ml) was added 4M hydrogen chloride dioxane solution (4 ml). After stirring at room temperature for 2.5 hr, the reaction mixture was concentrated under reduced pressure. Ethyl acetate was added to the concentrated residue, and the mixture was concentrated again under reduced pressure. The operation was performed twice to remove hydrogen chloride gas azeotropically. The residue was suspended in a mixture of ethanol (5 ml) and ethyl acetate (30 ml), and the suspension was filtered. The filtered product was washed twice with ethyl acetate and dried under reduced pressure to give the title compound (317.7 mg, 0.793 mmol, yield 99.1%) as a white solid.

melting point 179-184° C.

$^1$H-NMR (400 MHz, DMSO-d6): δ (ppm):12.55(1H, brs), 10.09(4H, br), 8.28(1H, s), 7.35(2H, d, J=8.6 Hz), 7.19 (2H, d, J=8.6 Hz), 4.35 (2H, t, J=6.6 Hz), 2.95 (2H, t, J=6.6 Hz), 2.16(3H, s)

$^{13}$C-NMR (100 MHz, DMSO-d6): δ (ppm):169.1, 159.4, 158.2, 155.7, 148.9, 139.7, 135.4, 129.9, 124.4, 121.6, 66.0, 33.7, 22.3

MS(ESI+):387.0729[M(free)+Na]$^+$, 403.0478[M(free)+K]$^+$

Production Example 9

2-[4-({[2-(acetylamino)-1,3-thiazol-4-yl]carbonyl}amino)phenyl]ethyl hydrazinecarboxylate hydrochloride Step 1

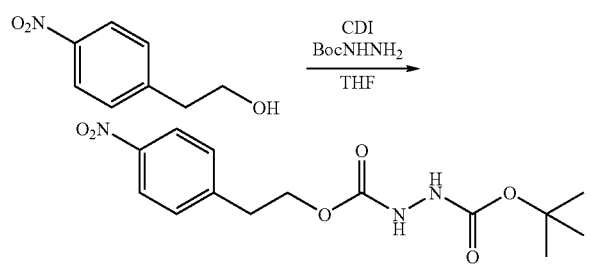

To a solution of 2-(4-nitrophenyl)ethanol (5.015 g, 30.00 mmol) in anhydrous tetrahydrofuran (50 ml) was added 1,1'-carbonyldiimidazole (5.839 g, 36.01 mmol), and the mixture was stirred at room temperature for 30 min. tert-Butyl carbazate (5.956 g, 45.06 mmol) was added, and the mixture was stirred at room temperature for 16 hr and further at 50° C. for 8 hr. 0.5M Hydrochloric acid (100 ml) and ethyl acetate (100 ml) were added to the reaction mixture, and the mixture was stirred, stood still and then partitioned. The organic layer was washed with 0.5M hydrochloric acid, water and saturated brine, dried over anhydrous magnesium sulfate, and concentrated under reduced pressure. The residue was purified by silica gel column chromatography (FUJI SILYSIA CHEMICAL LTD. BW-300SP 200 g, ethyl acetate:hexane=4:6→5:5) to give tert-butyl 2-(4-nitrophenyl)ethyl hydrazine-1,2-dicarboxylate (9.780 g, quantitative) as a slightly yellow solid.

Step 2

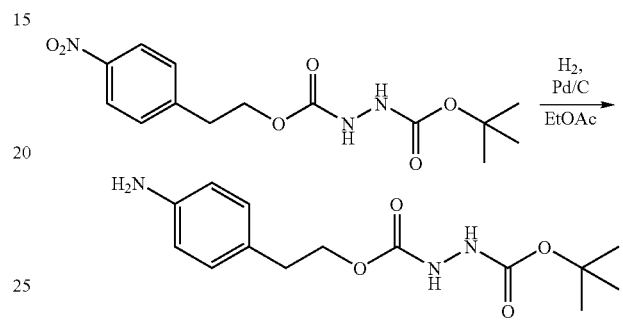

To a solution of tert-butyl 2-(4-nitrophenyl)ethyl hydrazine-1,2-dicarboxylate (9.780 g, 30.00 mmol) in ethyl acetate (100 ml) was added 10% palladium carbon (980.0 mg, containing 50% water), and the mixture was hydrogenated at room temperature and atmospheric pressure. The reaction mixture was filtered through celite, and the filtrate was concentrated under reduced pressure. The residue was suspended in a mixture of hexane (70 ml) and ethyl acetate (30 ml), filtered and dried under reduced pressure to give 2-(4-aminophenyl)ethyl tert-butyl hydrazine-1,2-dicarboxylate (5.207 g, 17.63 mmol, yield 58.8%) as a white solid.

Step 3

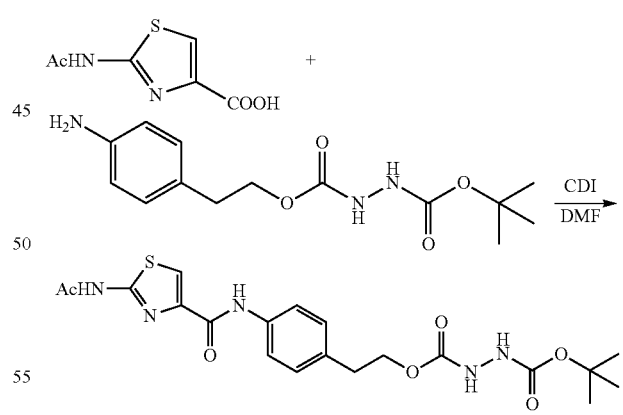

To a suspension of 2-(acetylamino)-1,3-thiazole-4-carboxylic acid (557.3 mg, 2.993 mmol) in anhydrous N,N-dimethylformamide (10 ml) was added 1,1'-carbonyldiimidazole (531.7 mg, 3.279 mmol), and the mixture was stirred at 50° C. for 2 hr. 2-(4-Aminophenyl)ethyl tert-butyl hydrazine-1,2-dicarboxylate (1.065 g, 3.607 mmol) was added, and the mixture was stirred at room temperature for 16 hr. Water (100 ml) and ethyl acetate (100 ml) were added to the reaction mixture, and the mixture was stirred, stood still and partitioned. The organic layer was washed with 0.5M hydrochloric acid, saturated aqueous sodium hydrogen carbonate and saturated brine, dried over anhydrous magnesium sulfate and concentrated under reduced pressure. The residue was suspended in tert-butyl methyl ether (30 ml), filtered, washed 3 times with tert-butyl methyl ether, and dried under reduced pressure to give 2-[(4-({[2-(acetylamino)-1,3-thiazol-4-yl]carbonyl}amino)phenyl]ethyl tert-butyl hydrazine-1,2-dicarboxylate (1.098 g, 2.368 mmol, yield 79.1%) as a white solid.

Step 4

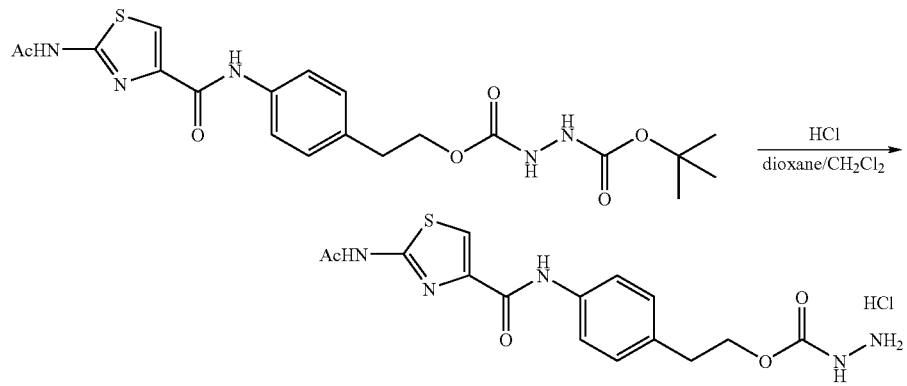

To a suspension of 2-[4-({[2-(acetylamino)-1,3-thiazol-4-yl]carbonyl}amino)phenyl]ethyl tert-butyl hydrazine-1,2-dicarboxylate (370.8 mg, 0.800 mmol) in anhydrous dichloromethane (4 ml) was added 4M hydrogen chloride dioxane solution (4 ml), and the mixture was stirred at room temperature for 18 hr. The reaction mixture was concentrated under reduced pressure. Ethyl acetate was added to the concentrated residue, and the mixture was concentrated again under reduced pressure. The operation was performed twice to remove hydrogen chloride gas azeotropically. The residue was suspended in ethyl acetate, filtered, washed 3 times with ethyl acetate and 3 times with methanol, and dried under reduced pressure to give 2-[4-({[2-(acetylamino)-1,3-thiazol-4-yl]carbonyl}amino)phenyl]ethyl hydrazinecarboxylate hydrochloride (280.8 mg, 0.702 mmol, yield 87.8%) as a white solid.

melting point 225-233° C.

$^1$H-NMR (400 MHz, DMSO-d6): δ (ppm):12.33(1H, brs), 10.18(3H, brs), 9.71(1H, brs), 7.94(1H, s), 7.67(2H, d, J=8.5 Hz), 7.24(2H, d, J=8.4 Hz), 4.30(2H, t, J=6.7 Hz), 2.89(2H, t, J=6.6 Hz), 2.18(3H, s)

$^{13}$C-NMR (100 MHz, DMSO-d6): δ (ppm):169.2, 159.3, 158.0, 155.9, 144.5, 136.9, 133.2, 129.3, 120.1, 118.3, 66.3, 34.1, 22.6

MS(ESI+):364.1066[M(free)+H]$^+$, 386.0889[M(free)+Na]$^+$

Production Example 10

3-{2-[2-(acetylamino)-1,3-thiazol-4-yl]ethyl}phenyl hydrazinecarboxylate hydrochloride Step 1

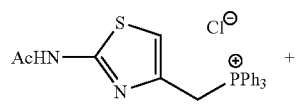 +

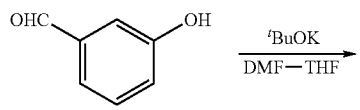

To a solution of {[2-(acetylamino)-1,3-thiazol-4-yl]methyl}(triphenyl)phosphonium chloride (3.894 g, 8.598 mmol) and 3-hydroxybenzaldehyde (1.000 g, 8.189 mmol) in anhydrous N,N-dimethylformamide (42 ml) was added dropwise potassium tert-butoxide tetrahydrofuran solution (1M, 25.4 ml, 25.4 mmol) at 0° C. After stirring at 0° C. for 30 min, the mixture was stirred at room temperature for 2 hr. The reaction mixture was cooled to 0° C., and iced water (100 ml) was added. The mixture was washed twice with ethyl acetate, and the aqueous layer was acidified with 1M hydrochloric acid (pH 2.5). The mixture was extracted 3 times with ethyl acetate, and the combined organic layer was washed twice with saturated brine, dried over anhydrous magnesium sulfate, and concentrated under reduced pressure. The residue was purified by silica gel column chromatography (FUJI SILYSIA CHEMICAL LTD. BW-300SP 120 g, ethyl acetate: hexane=1:1) to give N-{3-[2-(4-hydroxyphenyl)vinyl]-1,3-thiazol-2-yl}acetamide (1.953 g, 7.503 mmol, yield 91.6%) as a slightly yellow solid.

Step 2

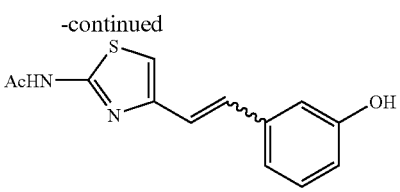

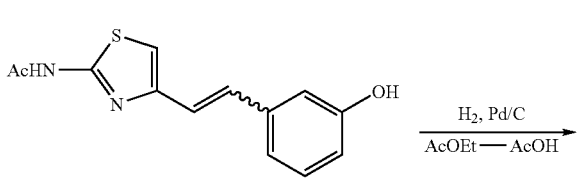

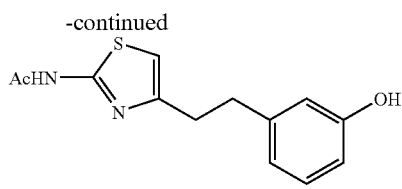

N-{3-[2-(4-Hydroxyphenyl)vinyl]-1,3-thiazol-2-yl}acetamide (1.900 g, 7.299 mmol) was dissolved in a mixture of ethyl acetate (300 ml) and acetic acid (50 ml), and 10% palladium carbon (760 mg, containing 50% water) was added. The mixture was hydrogenated at room temperature under 4-5 atm. After the completion of the reaction, the reaction mixture was filtered through celite, and the filtrate was concentrated under reduced pressure. The residue was dissolved in ethyl acetate by heating, and recrystallized by cooling to give N-{3-[2-(4-hydroxyphenyl)ethyl]-1,3-thiazol-2-yl}acetamide (1.834 g, 6.993 mmol, yield 95.8%) as a white solid.

Step 3

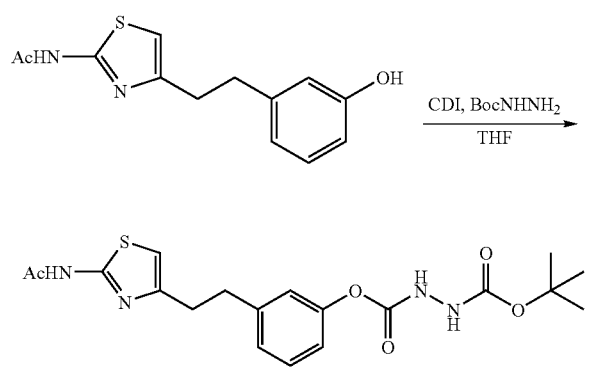

In a similar manner as in Production Example 1, step 3, 4-{2-[2-(acetylamino)-1,3-thiazol-4-yl]ethyl}phenyl tert-butyl hydrazine-1,2-dicarboxylate (636.1 mg, 1.513 mmol, yield 52.9%) was obtained as a white solid from N-{3-[2-(4-hydroxyphenyl)ethyl]-1,3-thiazol-2-yl}acetamide (750.0 mg, 2.859 mmol).

Step 4

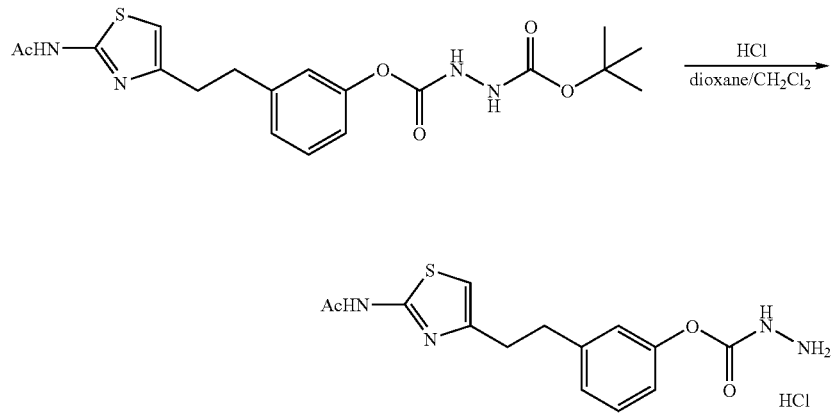

In a similar manner as in Production Example 1, step 4, 4-{2-[2-(acetylamino)-1,3-thiazol-4-yl]ethyl}phenyl tert-butyl hydrazine-1,2-dicarboxylate (260.0 mg, 0.618 mmol) was deprotected to give the title compound (219.0 mg, 0.614 mmol, yield 99.3%) as a white solid.

melting point 158-162° C.

$^1$H-NMR (400 MHz, DMSO-d6): δ (ppm):12.11(1H, brs), 10.99(1H, brs), 11.2-9.8(2H, br), 8.8-7.6(1H, br), 7.32(1H, t, J=7.7 Hz), 7.11(1H, d, J=7.4 Hz), 7.02-6.97(2H, m), 6.74(1H, s), 2.97-2.86(4H, m), 2.11(3H, s)

$^{13}$C-NMR (100 MHz, DMSO-d6): δ (ppm):168.6, 157.9, 154.3, 150.4, 150.3, 143.8, 129.8, 126.4, 121.6, 119.4, 107.9, 34.5, 32.8, 22.9

MS(ESI+):321.0972[M(free)+H]$^+$, 343.0793[M(free)+Na]$^+$

Production Example 11

3-{2-[2-(acetylamino)-1,3-thiazol-4-yl]ethyl}benzyl hydrazinecarboxylate hydrochloride Step 1

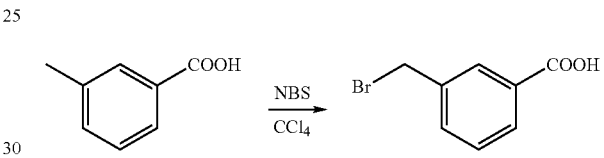

m-Toluic acid (13.62 g, 100.0 mmol) was brominated by a method similar to that of Production Example 4, step 1, to give 3-(bromomethyl)benzoic acid (16.85 g, 78.36 mmol, yield 78.4%) as a pale-yellow solid.

Step 2

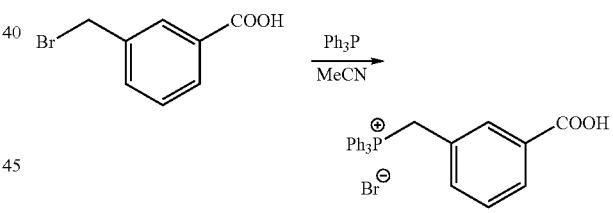

To a solution of 3-(bromomethyl)benzoic acid (16.50 g, 76.73 mmol) in acetonitrile (76.7 ml) was added triphenylphosphine (22.14 g, 84.40 mmol). After heating the mixture under reflux for 2 hr, the reaction mixture was cooled to room temperature. The precipitate was collected by filtration and dried under reduced pressure to give (3-carboxybenzyl)(triphenyl)phosphoniumbromide (30.13 g, 63.12 mmol, yield 82.3%) as a white solid.

Step 3

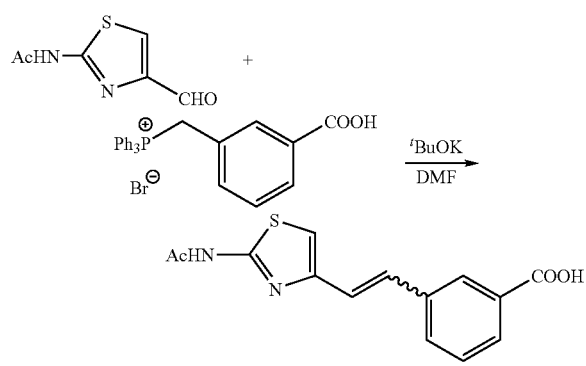

N-(4-Formyl-1,3-thiazol-2-yl)acetamide (1.702 g, 10.00 mmol) and (3-carboxybenzyl)(triphenyl)phosphonium bromide (5.251 g, 11.00 mmol) were condensed by a method similar to that of Production Example 4, step 3, to give 3-{2-[2-(acetylamino)-1,3-thiazol-4-yl]vinyl}benzoic acid (2.862 g, 9.926 mmol, yield 99.3%) as a pale-yellow solid.

Step 4

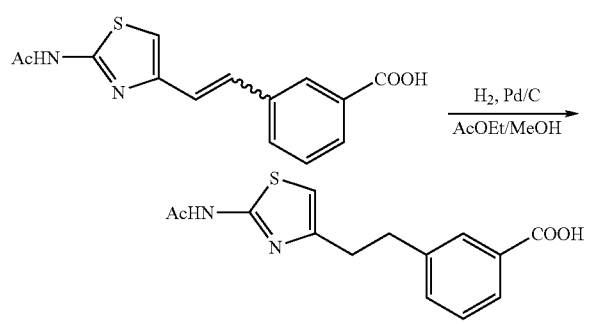

3-{2-[2-(Acetylamino)-1,3-thiazol-4-yl]vinyl}benzoic acid (1.780 g, 6.174 mmol) was hydrogenated by a method similar to that of Production Example 4, step 4, to give 3-{2-[2-(acetylamino)-1,3-thiazol-4-yl]ethyl}benzoic acid (1.323 g, 4.557 mmol, yield 73.8%) as a white solid.

Step 5

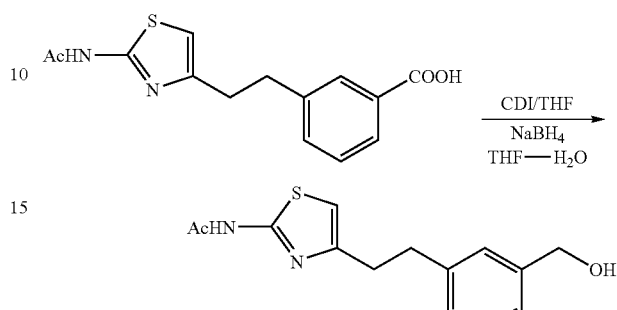

3-{2-[2-(Acetylamino)-1,3-thiazol-4-yl]ethyl}benzoic acid (844.6 mg, 2.909 mmol) was reduced by a method similar to that of Production Example 4, step 5, to give N-(4-{2-[3-(hydroxymethyl)phenyl]ethyl}-1,3-thiazol-2-yl)acetamide (850.0 mg, quantitative) as an off-white solid.

Step 6

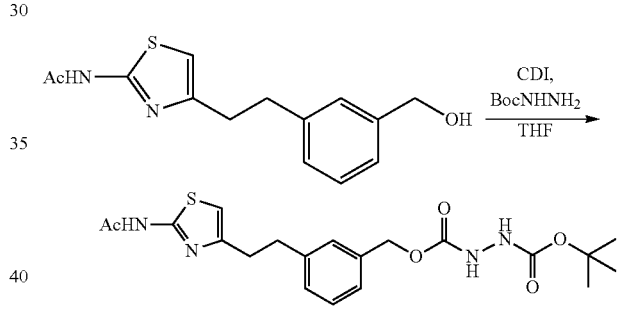

In a similar manner as in Production Example 4, step 6, 3-{2-[2-(acetylamino)-1,3-thiazol-4-yl]ethyl}benzyl tert-butyl hydrazine-1,2-dicarboxylate (710.0 mg, 1.634 mmol, yield 86.2%) was obtained as a white solid from N-(4-{2-[3-(hydroxymethyl)phenyl]ethyl}-1,3-thiazol-2-yl)acetamide (524.0 mg, 1.896 mmol).

Step 7

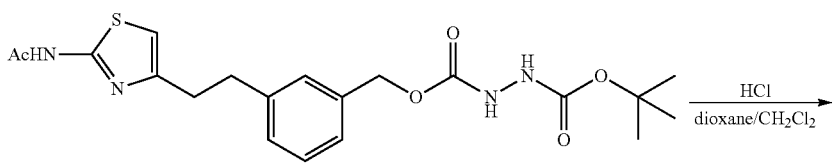

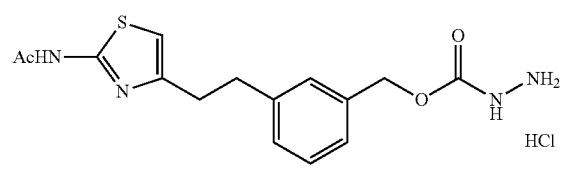

In a similar manner as in Production Example 1, step 4, 3-{2-[2-(acetylamino)-1,3-thiazol-4-yl]ethyl}benzyl tert-butyl hydrazine-1,2-dicarboxylate (406.0 mg, 0.934 mmol) was deprotected to give the title compound (329.1 mmol, 0.887 mmol, yield 95.0%) as a white solid.

melting point 113-119° C.

$^1$H-NMR (400 MHz, DMSO-d6): δ (ppm):12.07(1H, brs), 10.37(3H, brs), 7.30-7.16(4H, m), 6.74(1H, s), 5.14(2H, s), 3.55-2.86(4H, m), 2.11(3H, s)

$^{13}$C-NMR (100 MHz, DMSO-d6): δ (ppm):168.7, 157.9, 156.2, 150.6, 142.2, 136.2, 128.9, 128.7, 128.5, 126.2, 107.9, 67.6, 34.9, 33.2, 22.9

MS(ESI+):335.1145[M(free)+H]$^+$, 357.0957[M(free)+Na]$^+$

Production Example 12

2-(3-{2-[2-(acetylamino)-1,3-thiazol-4-yl]ethyl}phenyl)ethyl hydrazinecarboxylate hydrochloride Step 1

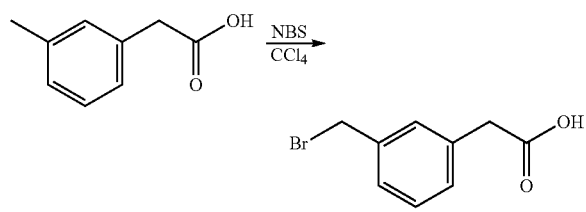

To a solution of m-tolylacetic acid (25.00 g, 166.5 mmol) in anhydrous carbon tetrachloride (200 ml) was added N-bromosuccinimide (30.00 g, 168.6 mmol), and the mixture was gradually heated to the boiling point. After heating the mixture under reflux for 5.5 hr, the reaction mixture was cooled to room temperature, the insoluble material was removed by filtration and washed twice with carbon tetrachloride (100 ml). The filtrate was concentrated, carbon tetrachloride (60 ml) was added and the residue was dissolved by heating at about 70° C. The solution was cooled to about 40° C., and hexane (300 ml) was added dropwise. After stirring at room temperature for 30 min, the precipitated crystals were filtered, washed with hexane and dried under reduced pressure to give (3-bromomethylphenyl)acetic acid (22.80 g, 99.53 mmol, yield 59.8%) as a white solid.

Step 2

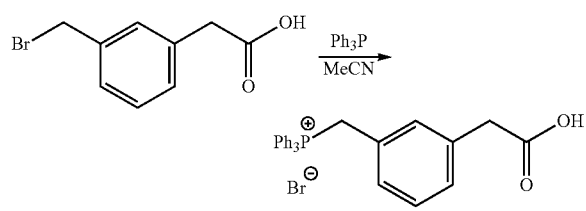

A solution of (3-bromomethylphenyl)acetic acid (22.00 g, 96.04 mmol) and triphenylphosphine (30.23 g, 115.2 mmol) in anhydrous acetonitrile (300 ml) was heated under reflux for 16 hr. After cooling to room temperature, the solution was concentrated under reduced pressure to about 100 g. Diethyl ether (200 ml) was added, and the mixture was stirred at room temperature for 1 hr. The precipitated crystals were collected by filtration, washed 3 times with diethyl ether and dried under reduced pressure to give [(3-carbonylmethyl)benzyl](triphenyl)phosphonium bromide (43.60 g, 88.73 mmol, yield 92.4%) as a white solid.

Step 3

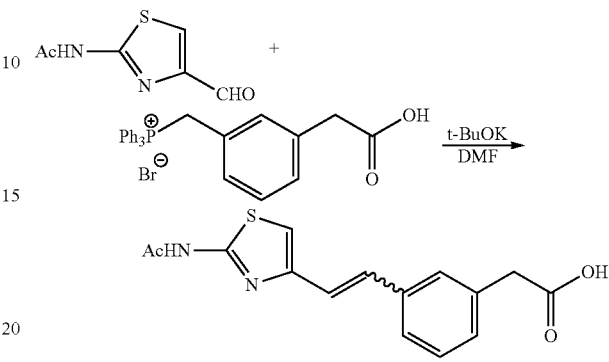

To a suspension of [(3-carbonylmethyl)benzyl](triphenyl)phosphoniumbromide (9.529 g, 19.39 mmol) in anhydrous N,N-dimethylformamide (85 ml) was added potassium tert-butoxide (5.935 g, 52.89 mmol) at 0° C. by small portions. After stirring at room temperature for 30 min, (4-formyl-1,3-thiazol-2-yl)acetamide (3.000 g, 17.63 mmol) was added, and the mixture was stirred for 3 hr. After cooling to 0° C., water (200 ml) was added, and the mixture was washed twice with ethyl acetate (100 ml). 6M Hydrochloric acid was added dropwise to the aqueous layer at 0° C. to adjust to pH 3, and the mixture was stirred for 30 min. The precipitate was collected by filtration, washed 3 times with water and twice with diisopropyl ether, and dried under reduced pressure to give 3-{2-[2-(acetylamino)-1,3-thiazol-4-yl]vinyl}phenylacetic acid (4.625 g, 15.30 mmol, yield 86.8%) as a white solid.

Step 4

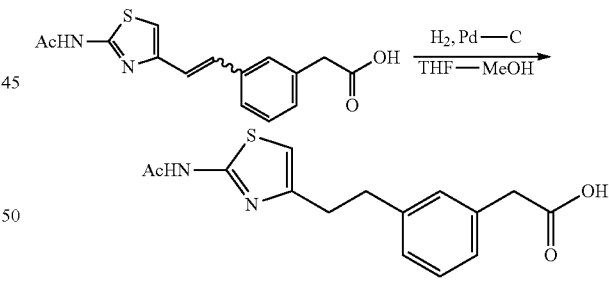

3-{2-[2-(Acetylamino)-1,3-thiazol-4-yl]vinyl}phenylacetic acid (4.500 g, 14.88 mmol) was dissolved in a mixed solvent of tetrahydrofuran (225 ml) and methanol (90 ml), and 20% palladium carbon (containing 50% water, 1.800 g) was added. Hydrogenation was performed at room temperature −30° C., 4 atm. After the completion of the reaction, the reaction mixture was filtered through celite, and the filtrate was concentrated. Diethyl ether (100 ml) was added to the residue, and the precipitate was collected by filtration. The filtered product was washed 3 times with diethyl ether, and dried under reduced pressure to give 3-{2-[2-(acetylamino)-1,3-thiazol-4-yl]ethyl}phenylacetic acid (4.152 g, 13.64 mmol, yield 91.7%) as a white solid.

Step 5

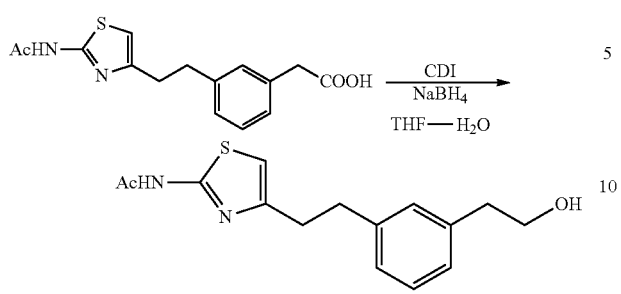

(3-{2-[2-(Acetylamino)-1,3-thiazol-4-yl]ethyl}phenyl)acetic acid (935.0 mg, 3.072 mmol) was reduced by a method similar to that of Production Example 4, step 5, to give N-(4-{2-[3-(2-hydroxyethyl)phenyl]ethyl}-1,3-thiazol-2-yl)acetamide (670.0 mg, 2.307 mmol, yield 75.1%) as a white solid.

Step 6

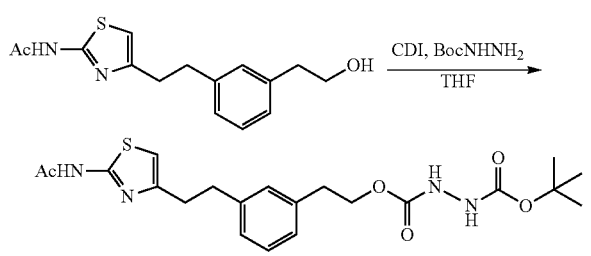

In a similar manner as in Production Example 4, step 6, 2-(3-{2-[2-(acetylamino)-1,3-thiazol-4-yl]ethyl}phenyl)ethyl tert-butyl hydrazine-1,2-dicarboxylate (534.9 mg, quantitative) was obtained as a white solid from N-(4-{2-[3-(2-hydroxyethyl)phenyl]ethyl}-1,3-thiazol-2-yl)acetamide (300.0 mg, 1.033 mmol).

Step 7

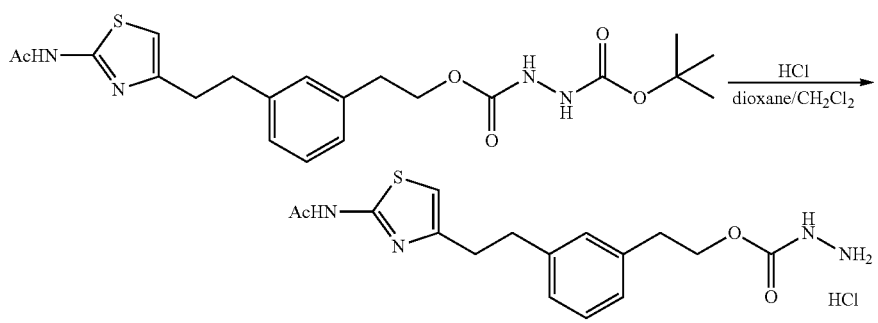

2-(3-{2-[2-(Acetylamino)-1,3-thiazol-4-yl]ethyl}phenyl)ethyl tert-butyl hydrazine-1,2-dicarboxylate (1.033 mmol) was deprotected by a method similar to that of Production Example 4, step 7, to give the title compound (399.5 mg, quantitative) as a white solid.

melting point 138-140° C.

$^1$H-NMR (400 MHz, DMSO-d6): δ (ppm):12.06(1H, brs), 10.8-9.8(4H, br), 7.20(1H, t, J=7.6 Hz), 7.11-7.04(3H, m), 6.73(1H, s), 4.30(2H, t, J=6.9 Hz), 2.92-2.85(6H, m), 2.11 (3H, s)

$^{13}$C-NMR (100 MHz, DMSO-d6): δ (ppm):168.7, 157.9, 156.2, 150.8, 142.0, 138.0, 129.3, 128.8, 126.9, 107.8, 66.7, 35.0, 34.9, 33.3, 22.9

MS(ESI+):349.1292[M(free)+H]$^+$, 371.1106[M(free)+Na]$^+$

Production Example 13

{5-[2-(2-acetylamino-1,3-thiazol-4-yl)ethyl]thiophen-2-yl}methyl hydrazinecarboxylate hydrochloride Step 1

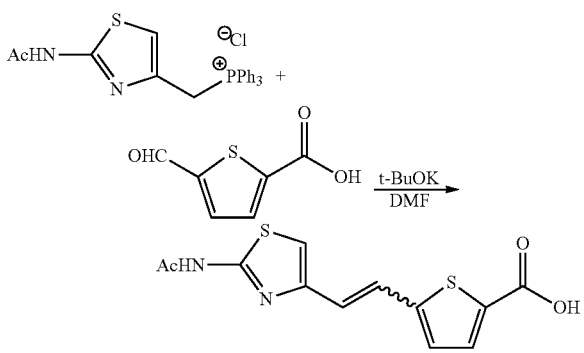

To a solution of {[2-(acetylamino)-1,3-thiazol-4-yl]methyl}(triphenyl)phosphonium chloride (3.771 g, 8.325 mmol) in anhydrous N,N-dimethylformamide (35 ml) was added potassium tert-butoxide (2.515 g, 22.41 mmol) at 0° C., and the mixture was stirred for 15 min. 5-Formylthiophene-2-carboxylic acid (1.000 g, 6.404 mmol) was added by small portions, and the mixture was stirred at 0° C. for 30 min. The mixture was warmed to room temperature, stirred for 2 hr, and poured into iced water (300 ml). After stirring for 30 min, the mixture was washed twice with ethyl acetate. The aqueous layer was cooled to 0° C., and adjusted to pH 3 by dropwise addition of 6M hydrochloric acid. After stirring at 0-5° C. for 2 hr, the precipitated crystals were collected by filtration, washed 3 times with water, and twice with diisopropyl ether and dried under reduced pressure to give 5-{2-[2-(acetylamino)-1,3-thiazol-4-yl]vinyl}thiophene-2-carboxylic acid (1.104 g, 3.751 mmol, yield 58.6%) as a yellow ocher solid.

Step 2

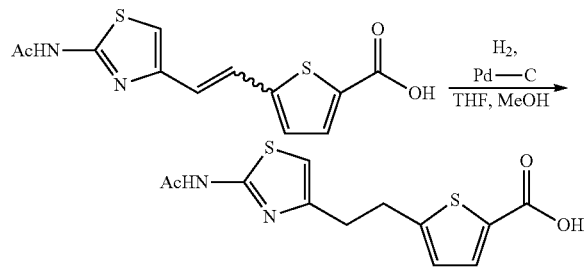

5-{2-[2-(Acetylamino)-1,3-thiazol-4-yl]vinyl}thiophene-2-carboxylic acid (900.0 mg, 3.058 mmol) was dissolved in a mixed solvent of tetrahydrofuran (250 ml) and methanol (100 ml). 20% Palladium carbon was added, and the mixture was hydrogenated at room temperature under 4 atm. After the completion of the reaction, the reaction mixture was filtered through celite, and the filtrate was concentrated under reduced pressure. Diethyl ether (100 ml) was added to the concentrated residue, and the precipitate was collected by filtration, washed with diethyl ether, and dried under reduced pressure to give 5-{2-[2-(acetylamino)-1,3-thiazol-4-yl]ethyl}thiophene-2-carboxylic acid (738.1 mg, 2.490 mmol, yield 81.4%) as an off-white solid.

Step 3

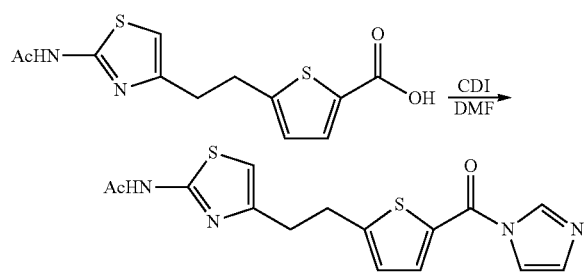

To a solution of 5-{2-[2-(acetylamino)-1,3-thiazol-4-yl]ethyl}thiophene-2-carboxylic acid (350.0 mg, 1.181 mmol) in anhydrous N,N-dimethylformamide (3 ml) was added 1,1'-carbonyldiimidazole (287.2 mg, 1.771 mmol), and the mixture was stirred at 50° C. for 1 hr. After cooling to room temperature, diisopropyl ether (15 ml) was added dropwise. After stirring for 5 min, the precipitate was collected by filtration, washed twice with diisopropyl ether and 3 times with ethyl acetate, and dried under reduced pressure to give N-(4-{2-[5-(imidazole-1-carbonyl)-thiophen-2-yl]ethyl}-1,3-thiazol-2-yl)acetamide (346.2 mg, 0.999 mmol, yield 84.6%) as a yellow solid.

Step 4

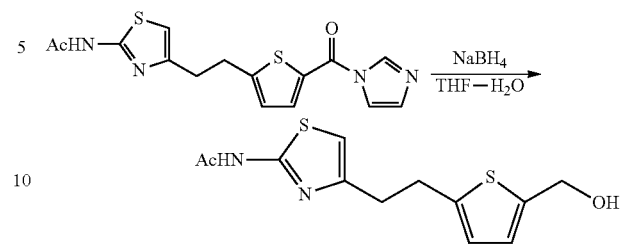

A solution of N-(4-{2-[5-(1H-imidazol-1-ylcarbonyl)thiophen-2-yl]ethyl}-1,3-thiazol-2-yl)acetamide (220.0 mg, 0.635 mmol) in anhydrous tetrahydrofuran (17.6 ml) was cooled to 0° C., and water (4.4 ml) and sodium borohydride (240.2 mg, 6.350 mmol) were added. After stirring at 0° C. for 1.5 hr, the reaction mixture was concentrated to about 2 ml, and saturated aqueous ammonium chloride (20 ml) was added dropwise. This was extracted 3 times with ethyl acetate, and the combined organic layer was washed with aqueous ammonium chloride and saturated brine. The mixture was dried over anhydrous magnesium sulfate and concentrated under reduced pressure. The concentrated residue was purified by silica gel column chromatography (FUJI SILYSIA CHEMICAL LTD. BW-300SP 100 g, ethyl acetate:hexane=2:1) to give N-(4-{2-[5-(hydroxymethyl)thiophen-2-yl]ethyl}-1,3-thiazol-2-yl)acetamide (157.1 mg, 0.556 mmol, yield 87.6%) as a white solid.

Step 5

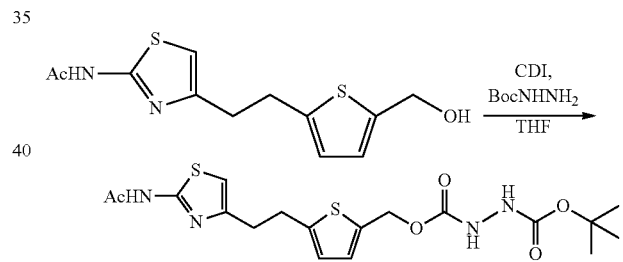

In a similar manner as in Production Example 4, step 6, (5-{2-[2-(acetylamino)-1,3-thiazol-4-yl]ethyl}thiophen-2-yl)methyl tert-butyl hydrazine-1,2-dicarboxylate (158.2 mg, quantitative) was obtained as a white solid from N-(4-{2-[5-(hydroxymethyl)thiophen-2-yl]ethyl}-1,3-thiazol-2-yl)acetamide (100.0 mg, 0.353 mmol).

Step 6

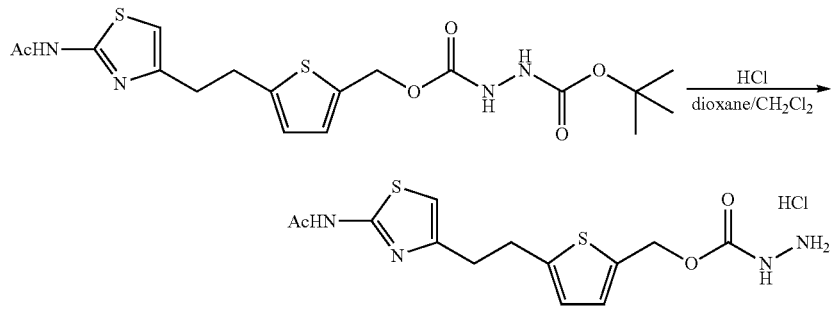

(5-{2-[2-(Acetylamino)-1,3-thiazol-4-yl]ethyl}thiophen-2-yl)methyl tert-butyl hydrazine-1,2-dicarboxylate (0.353 mmol) was deprotected by a method similar to that in Production Example 4, step 7, to give the title compound (73.0 mg, 0.194 mmol, yield 54.9%) as a white solid.

melting point 137-141° C.

$^1$H-NMR (400 MHz, DMSO-d6): δ (ppm):12.06(1H, brs), 7.5-6.7(4H, br), 6.96(1H, d, J=3.6 Hz), 6.77(1H, s), 6.69(1H, d, J=3.6 Hz), 4.93(2H, s), 3.12(2H, t, J=7.5 Hz), 2.90(2H, t, J=7.5 Hz), 2.10(3H, s)

$^{13}$C-NMR (100 MHz, DMSO-d6): δ (ppm):168.4, 157.7, 149.6, 146.2, 137.9, 128.4, 124.6, 108.1, 41.3, 32.9, 29.1, 22.6

Production Example 14

2-(5-{2-[2-(acetylamino)-1,3-thiazol-4-yl]ethyl}thiophen-2-yl)ethyl hydrazinecarboxylate hydrochloride Step 1

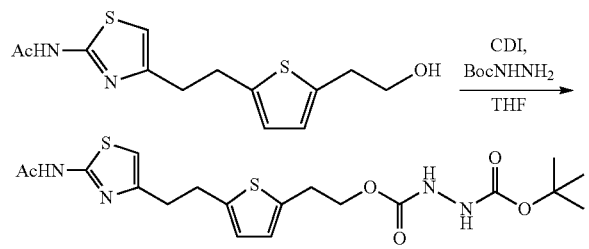

In a similar manner as in Production Example 2, step 1, 2-(5-{2-[2-(acetylamino)-1,3-thiazol-4-yl]ethyl}thiazol-2-yl)ethyl tert-butyl hydrazine-1,2-dicarboxylate (571.6 mg, quantitative) was obtained as a white solid from N-(4-{2-[5-(2-hydroxyethyl)thiazol-2-yl]ethyl}-1,3-thiazol-2-yl)acetamide (300.0 mg, 1.012 mmol).

Step 2

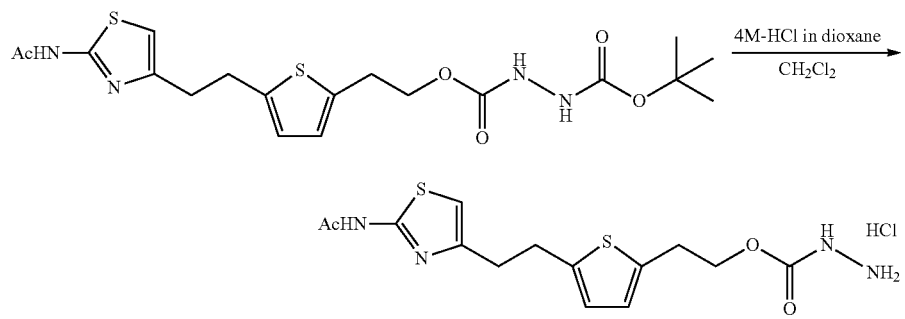

In a similar manner as in Production Example 2, step 2, the title compound (263.4 mg, 0.674 mmol, yield 66.6%) was obtained as a white solid from 2-(5-{2-[2-(acetylamino)-1,3-thiazol-4-yl]ethyl}thiazol-2-yl)ethyl tert-butyl hydrazine-1,2-dicarboxylate (571.6 mg, corresponding to 1.012 mmol).

melting point: (no clear melting point, decomposed around 240° C.)

$^1$H-NMR (200 MHz, DMSO-d6): δ(ppm):12.06(1H, brs), 9.06(1H, brs), 7.23(2H, brs), 6.77(1H, s), 6.69(2H, d, J=3.3 Hz), 6.65(2H, d, J=3.3 Hz), 4.17(2H, t, J=6.5 Hz), 3.15-2.95 (4H, m), 2.95-2.84(2H, m), 2.10(3H, s)

$^{13}$C-NMR (50 MHz, DMSO-d6): δ(ppm):168.4, 157.7, 157.2, 149.9, 142.4, 137.7, 125.5, 124.5, 107.9, 65.2, 33.2, 29.4, 29.0, 22.7

MS(ESI+):355.0896[M(free)+H]$^+$, 377.0724[M(free)+Na]$^+$

Production Example 15

3-(4-{2-[2-(acetylamino)-1,3-thiazol-4-yl]ethyl}thiophen-2-yl)propyl hydrazinecarboxylate hydrochloride Step 1

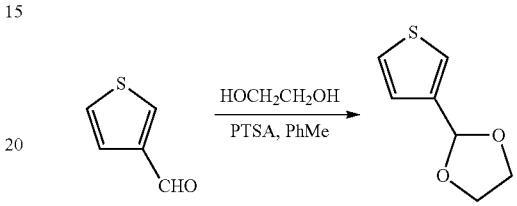

To a solution of thiophene-3-carbaldehyde (25.00 g, 222.9 mmol) in toluene (250 ml) were added ethylene glycol (69.18 g, 1115 mmol) and p-toluenesulfonic acid (424.0 mg, 2.229 mmol). The mixture was heated under reflux for 4 hr while separating generated water using Dean-Stark trap. After cooling to 0° C., saturated aqueous sodium hydrogen carbonate solution (50 ml) was added, and the mixture was stirred, stood still and then partitioned. The aqueous layer was extracted twice with ethyl acetate. The combined organic layer was washed with water and saturated brine, and dried over anhydrous magnesium sulfate. The residue was concentrated under reduced pressure, filtered through silica gel pad (FUJI SILYSIA CHEMICAL LTD. BW-300SP 100 g), and washed with ethyl acetate/hexane mixed solvent (1:2, 1000 ml). The filtrate was concentrated under reduced pressure to give 2-(thiophen-3-yl)-1,3-dioxolane (33.40 g, 213.8 mmol, yield 95.9%) as a yellow oil.

Step 2

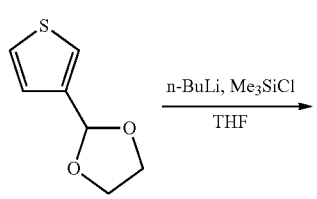

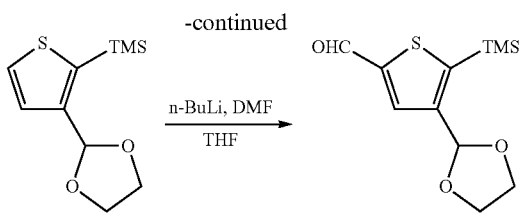

A solution of 2-(thiophen-3-yl)-1,3-dioxolane (10.00 g, 64.02 mmol) in anhydrous tetrahydrofuran (50 ml) was cooled in a dry ice-methanol bath, and n-butyllithium hexane solution (1.59M, 44.3 ml, 70.4 mmol) was added dropwise while preventing the reaction mixture from exceeding −55° C. After stirring for 1 hr, chlorotrimethylsilane (8.94 ml, 70.4 mmol) was added dropwise while preventing the reaction mixture from exceeding −60° C. After stirring at −78 to −60° C. for 30 min, the mixture was warmed to 0° C. over 30 min and stirred at 0° C. for 1 hr. The reaction mixture was cooled again in a dry ice-methanol bath, and n-butyllithium hexane solution (1.59M, 46.3 ml, 73.6 mmol) was added dropwise while preventing the reaction mixture from exceeding −60° C. After stirring at −78 to −60° C. for 1 hr, N,N-dimethylformamide (12.4 ml, 160 mmol) was added dropwise, and the mixture was further stirred for 1 hr. The mixture was warmed to 0° C. over 1 hr, and saturated aqueous ammonium chloride solution (100 ml) was added. The mixture was washed 3 times with ethyl acetate, and the combined organic layer was washed twice with 0.2M hydrochloric acid and once with saturated brine. To the organic layer were added anhydrous magnesium sulfate and activated carbon, and the mixture was stirred for 5 min and filtered. The filtrate was concentrated under reduced pressure to give 4-(1,3-dioxolan-2-yl)-5-(trimethylsilyl)thiophene-2-carbaldehyde (16.09 g, 62.76 mmol, yield 98.0%) as an orange oil.

Step 3

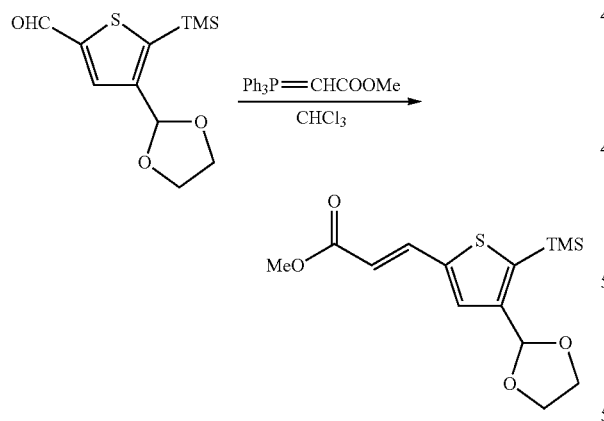

To a solution of 4-(1,3-dioxolan-2-yl)-5-(trimethylsilyl)thiophene-2-carbaldehyde (12.82 g, 50.00 mmol) in chloroform (128 ml) was added methyl (triphenyl phosphanylidene)acetate (17.55 g, 52.50 mmol) at 0° C. by small portions. After stirring at 0° C. for 1 hr, the mixture was stirred at room temperature for 12 hr. The reaction mixture was concentrated under reduced pressure, diethyl ether (200 ml) was added to the residue, and the mixture was stirred. The insoluble material (mainly triphenylphosphineoxide) was filtered, and washed 4 times with diethyl ether (50 ml). The filtrate was concentrated under reduced pressure, and the concentrated residue was purified by silica gel column chromatography (FUJI SILYSIA CHEMICAL LTD. BW-300SP 450 g, ethyl acetate:hexane=1:6) to give methyl (2E)-3-[4-(1,3-dioxolan-2-yl)-5-(trimethylsilyl)thiophen-2-yl]acrylate (13.76 g, 44.04 mmol, yield 88.1%) as a pale-yellow oil.

Step 4

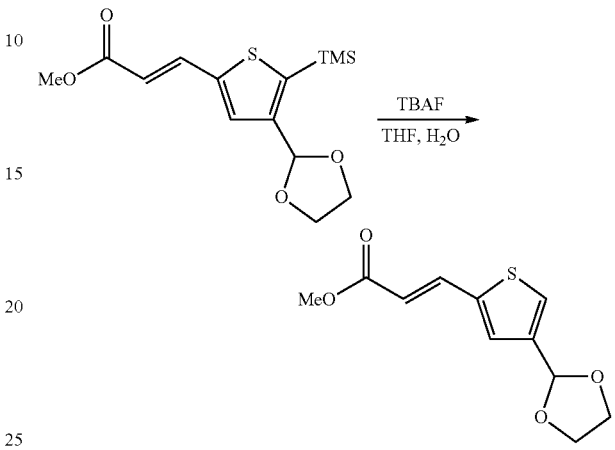

To a solution of methyl (2E)-3-[4-(1,3-dioxolan-2-yl)-5-(trimethylsilyl)thiophen-2-yl]acrylate (4.000 g, 12.80 mmol) in tetrahydrofuran (20 ml) was added water (0.2 ml), and the mixture was cooled to 0° C. Tetrabutylammoniumfluoride tetrahydrofuran solution (1M, 13.4 ml, 13.4 mmol) was added, and the mixture was stirred at 0° C. for 5 min and at room temperature for 10 min. The mixture was cooled to 0° C., saturated aqueous ammonium chloride solution (40 ml) was added, and the mixture was extracted 3 times with ethyl acetate. The combined organic layer was washed with saturated brine, dried over anhydrous magnesium sulfate, and concentrated under reduced pressure. The residue was purified by silica gel column chromatography (FUJI SILYSIA CHEMICAL LTD. BW-300SP 200 g, ethyl acetate:hexane=1:3) to give methyl (2E)-3-[4-(1,3-dioxolan-2-yl)thiophen-2-yl]acrylate (3.065 g, 12.76 mmol, 99.7%) as a colorless oil.

Step 5

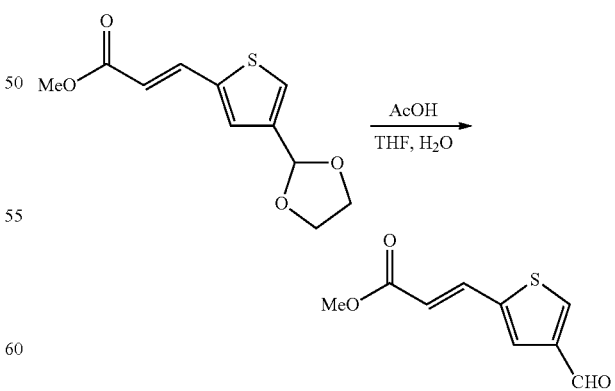

To a solution of methyl (2E)-3-[4-(1,3-dioxolan-2-yl)thiophen-2-yl]acrylate (3.050 g, 12.69 mmol) in tetrahydrofuran (10 ml) were added acetic acid (30 ml) and water (10 ml), and the mixture was stirred at 50° C. for 2 hr. After cooling to room temperature, the mixture was concentrated under reduced pressure, and water (30 ml) was added to the residue. The mixture was extracted 3 times with ethyl acetate, and the combined organic layer was washed with saturated brine, dried over anhydrous magnesium sulfate, concentrated to about 50 ml under reduced pressure, and hexane (200 ml) was added. The mixture was concentrated again to about 50 ml under reduced pressure, and the precipitate was collected by filtration, washed 3 times with hexane, and dried under reduced pressure to give methyl (2E)-3-(4-formylthiophen-2-yl)acrylate (2.213 g, 11.28 mmol, 88.9%) as a white solid.

Step 6

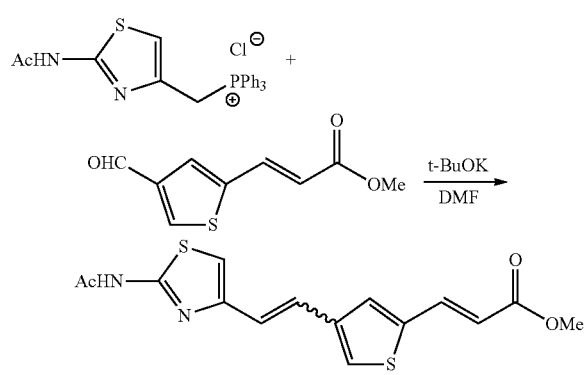

To {[2-(acetylamino)-1,3-thiazol-4-yl]methyl}(triphenyl)phosphoniumchloride (6.602 g, 14.58 mmol) was added anhydrous N,N-dimethylformamide (30 ml), and the mixture was cooled to 0° C. Potassium tert-butoxide (3.146 g, 28.03 mmol) was added, and the mixture was stirred at 0° C. for 15 min. A solution of methyl (2E)-3-(4-formylthiophen-2-yl)acrylate (2.200 g, 11.21 mmol) in anhydrous N,N-dimethylformamide (30 ml) was added dropwise, and the mixture was stirred at 0° C. for 1 hr. The reaction mixture was poured into ice-cooled dil. hydrochloric acid (600 ml, containing 15 mmol as HCl). Sodium chloride (10 g) was added, and the mixture was extracted 3 times with ethyl acetate. The combined organic layer was washed with saturated brine, dried over anhydrous magnesium sulfate and concentrated under reduced pressure. The residue was purified by silica gel column chromatography (FUJI SILYSIA CHEMICAL LTD. BW-300SP 500 g, ethyl acetate:hexane=1:1) to give methyl (2E)-3-(4-{2-[2-(acetylamino)-1,3-thiazol-4-yl]vinyl}thiophen-2-yl)acrylate (3.090 g, 9.241 mmol, 82.4%) as a yellowish-white solid.

Step 7

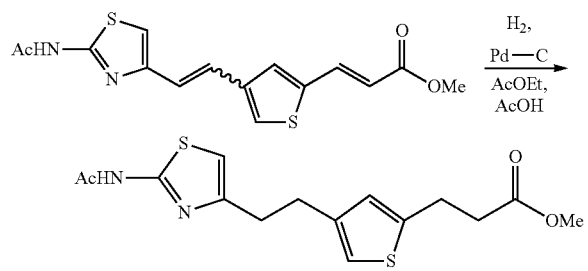

Methyl (2E)-3-(4-{2-[2-(acetylamino)-1,3-thiazol-4-yl]vinyl}thiophen-2-yl)acrylate (3.000 g, 8.971 mmol) was dissolved in ethyl acetate (400 ml) and acetic acid (100 ml). 20% Palladium carbon was added, and the mixture was hydrogenated at room temperature under an atmospheric pressure. After the completion of the reaction, the catalyst was filtered off, and the filtrate was concentrated under reduced pressure. The residue was purified by silica gel column chromatography (FUJI SILYSIA CHEMICAL LTD. BW-300SP, 100 g, ethyl acetate:hexane=2:3) to give methyl 3-(4-{2-[2-(acetylamino)-1,3-thiazol-4-yl]ethyl}thiophen-2-yl)propionate (2.521 g, 7.449 mmol, yield 83.0%) as a pale-yellow solid.

Step 8

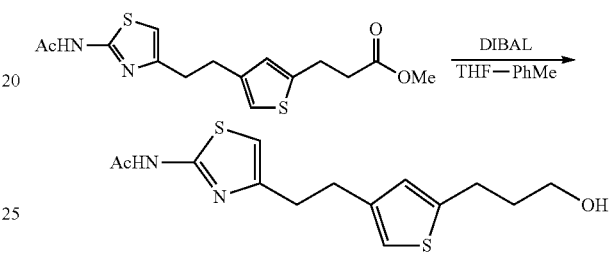

To a solution of methyl 3-(4-{2-[2-(acetylamino)-1,3-thiazol-4-yl]ethyl}thiophen-2-yl)propionate (1.450 g, 4.284 mmol) in anhydrous tetrahydrofuran (28 ml) was added dropwise 1.5M diisobutylaluminum hydride (10.7 ml, 16.1 mmol) at −50° C. over 30 min. After stirring at −50 to −40° C. for 2 hr, saturated aqueous potassium sodium tartrate solution (60 ml) was added. The mixture was warmed to room temperature, and stirred for 1.5 hr. The mixture was extracted 3 times with ethyl acetate, and washed with 1M hydrochloric acid, saturated-aqueous sodium hydrogen carbonate and saturated brine. After drying over anhydrous magnesium sulfate, the mixture was concentrated under reduced pressure. The residue was purified by silica gel column chromatography (FUJI SILYSIA CHEMICAL LTD. BW-300SP 100 g, ethyl acetate:hexane=2:1) to give N-(4-{2-[5-(3-hydroxypropyl)thiophen-3-yl]ethyl}-1,3-thiazol-2-yl)acetamide (499.9 mg, 1.610 mmol, yield 37.6%) as a white solid.

Step 9

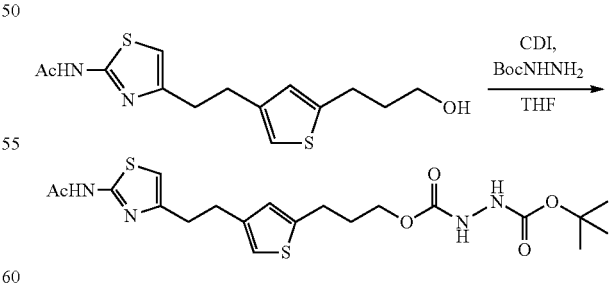

In a similar manner as in Production Example 2, step 1, 3-(4-{2-[2-(acetylamino)-1,3-thiazol-4-yl]ethyl}thiophen-2-yl)propyl tert-butyl hydrazine-1,2-dicarboxylate (362.9 mg, quantitative) was obtained as a colorless oil from N-(4-{2-[5-(3-hydroxypropyl)thiophen-3-yl]ethyl}-1,3-thiazol-2-yl)acetamide (205.0 mg, 0.660 mmol).

Step 10

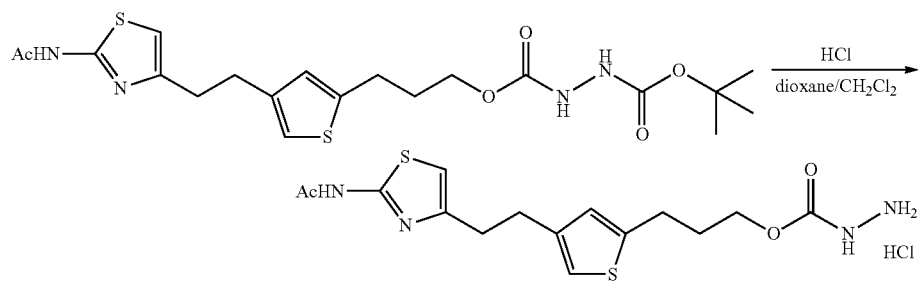

In a similar manner as in Production Example 2, step 2, the title compound (207.9 mg, 0.513 mmol, yield 77.7%) was obtained as a white solid from 3-(4-{2-[2-(acetylamino)-1,3-thiazol-4-yl]ethyl}thiophen-2-yl)propyl tert-butyl hydrazine-1,2-dicarboxylate (0.660 mmol).

melting point 150-153° C.

$^1$H-NMR (400 MHz, DMSO-d6): δ (ppm):12.06(1H, brs), 11.0-9.8(4H, br), 6.92(1H, s), 6.73(1H, s), 6.72(1H, s), 4.12 (2H, t, J=5.5 Hz), 2.90-2.80(4H, m), 2.80(2H, t, J=7.6 Hz), 2.11(3H, s), 1.90(2H, tt, J=7.6, 5.5 Hz)

$^{13}$C-NMR (100 MHz, DMSO-d6): δ (ppm):168.5, 157.7, 155.9, 150.3, 143.5, 141.6, 126.2, 118.5, 107.5, 65.0, 31.9, 30.5, 29.5, 25.7, 22.7

MS(ESI+):369.1006[M(free)+H]$^+$, 391.0827[M(free)+Na]$^+$

Production Example 16

3-(5-{2-[2-(acetylamino)-1,3-thiazol-4-yl] ethyl}thiophen-3-yl)propyl hydrazinecarboxylate hydrochloride Step 1

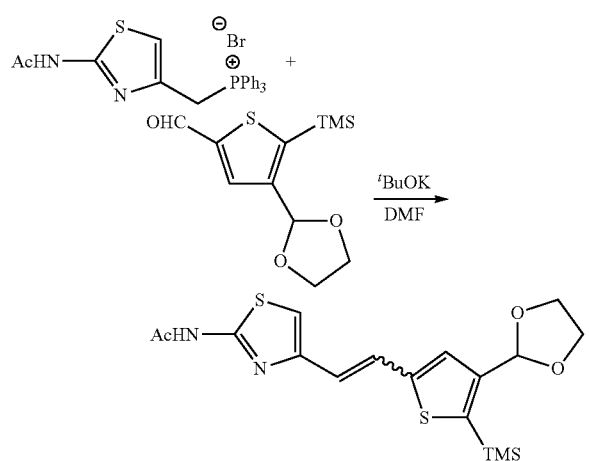

To a solution of {[2-(acetylamino)-1,3-thiazol-4-yl]methyl}(triphenyl)phosphoniumbromide (7.970 g, 16.03 mmol) in anhydrous N,N-dimethylformamide (32 ml) was added potassium tert-butoxide (3.687 g, 32.86 mmol) at 0° C., and the mixture was stirred for 1 hr. A solution of 4-(1,3-dioxolan-2-yl)-5-(trimethylsilyl)thiophene-2-carbaldehyde (2.740 g, 10.69 mmol) in anhydrous N,N-dimethylformamide (6 ml) was added dropwise, and the mixture was stirred for 1 hr. 1M Hydrochloric acid (17.0 ml) and iced water (170 ml) were added, and the mixture was extracted 3 times with ethyl acetate. The combined organic layer was washed with saturated brine, dried over anhydrous magnesium sulfate, and concentrated under reduced pressure. The residue was purified by silica gel column chromatography (FUJI SILYSIA CHEMICAL LTD. BW-300SP 200 g, ethyl acetate:dichloromethane=1:6) to give N-(4-{2-[4-(1,3-dioxolan-2-yl)-5-(trimethylsilyl)thiophen-2-yl]vinyl}-1,3-thiazol-2-yl)acetamide (4.010 g, 10.16 mmol, yield 95.0%) as an off-white solid.

Step 2

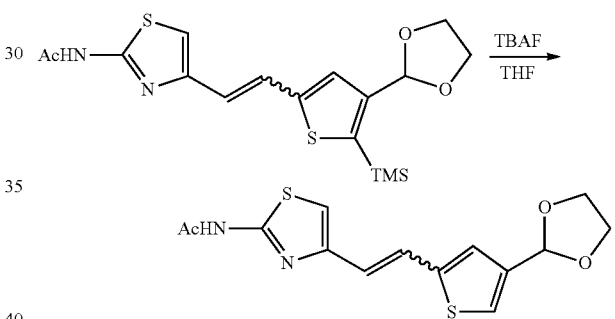

To a solution of N-(4-{2-[4-(1,3-dioxolan-2-yl)-5-(trimethylsilyl)thiophen-2-yl]vinyl}-1,3-thiazol-2-yl)acetamide (3.980 g, 10.09 mmol) in tetrahydrofuran (20 ml) was added 1M tetrabutylammoniumfluoride tetrahydrofuran solution (11.1 ml, 11.1 mmol) at room temperature, and the mixture was stirred for 1 hr. The reaction mixture was concentrated under reduced pressure, and the residue was purified by silica gel column chromatography (Merck 7734 100 g, ethyl acetate:dichloromethane=1:4→1:2) to give N-(4-{2-[4-(1,3-dioxolan-2-yl)thiophen-2-yl]vinyl}-1,3-thiazol-2-yl)acetamide (3.03 g, 9.40 mmol, yield 93.2%) as an off-white solid.

Step 3

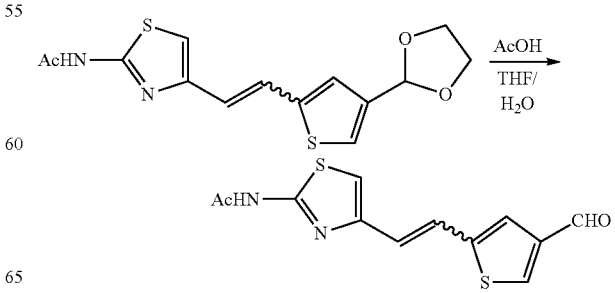

To N-(4-{2-[4-(1,3-dioxolan-2-yl)thiophen-2-yl]vinyl}-1,3-thiazol-2-yl)acetamide (1.418 g, 4.398 mmol) were added acetic acid (16.8 ml), tetrahydrofuran (5.6 ml) and water (5.6 ml), and the mixture was stirred at 55° C. for 2.5 hr. The reaction mixture was concentrated, and diisopropyl ether was added. The precipitated solid was collected by filtration, washed with diisopropyl ether and dried under reduced pressure to give N-{4-[2-(4-formylthiophen-2-yl)vinyl]-1,3-thiazol-2-yl}acetamide (1.136 g, 4.081 mmol, yield 92.8%) as a pale-yellow solid.

Step 4

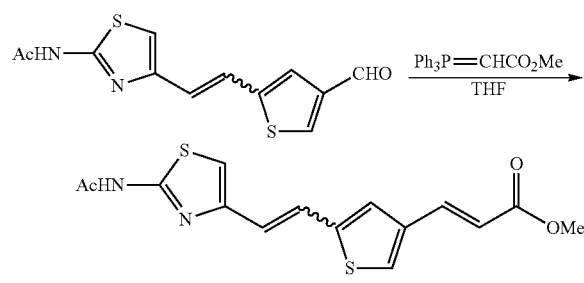

To a solution of N-{4-[2-(4-formylthiophene-2-yl)vinyl]-1,3-thiazol-2-yl}acetamide (1.133 g, 4.070 mmol) in anhydrous tetrahydrofuran (80 ml) was added methyl (triphenyl phosphanylidene)acetate (1.497 g, 4.477 mmol), and the mixture was stirred at room temperature for 1 hr. The reaction mixture was concentrated under reduced pressure, and the residue was purified by silica gel column chromatography (FUJI SILYSIA CHEMICAL LTD. FL60D 60 g, ethyl acetate:dichloromethane=1:5) to give methyl (2E)-3-(5-{2-[2-(acetylamino)-1,3-thiazol-2-yl]vinyl}thiophen-3-yl)-2-propenoate (2.320 g, containing triphenylphosphineoxide) as a pale-yellow solid.

Step 5

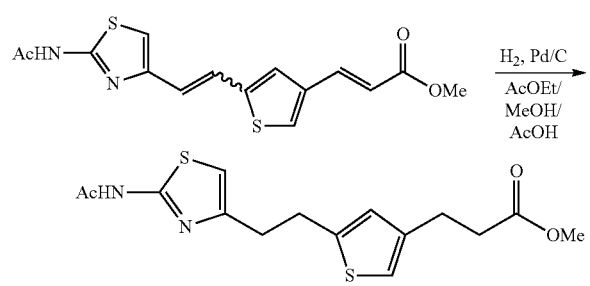

Methyl (2E)-3-(5-{2-[2-(acetylamino)-1,3-thiazol-2-yl]vinyl}thiophen-3-yl)-2-propenoate (corresponding to 4.070 mmol) was dissolved in a mixture of ethyl acetate (120 ml), methanol (40 ml) and acetic acid (40 ml). 10% Palladium carbon (700 mg, containing 50% water) was added, and the mixture was hydrogenated at room temperature under an atmospheric pressure. After the completion of the reaction, the reaction mixture was filtered through celite, and the filtrate was concentrated under reduced pressure. The residue was purified by silica gel column chromatography (FUJI SILYSIA CHEMICAL LTD. BW-300SP 60 g, ethyl acetate:dichloromethane=1:7), and the impure fractions insufficient in separation were purified again by column chromatography to give methyl 3-(5-{2-[2-(acetylamino)-1,3-thiazol-2-yl]ethyl}thiophen-3-yl)propionate (917.4 mg, 2.711 mmol, total yield from step 4 66.6%) as an off-white solid.

Step 6

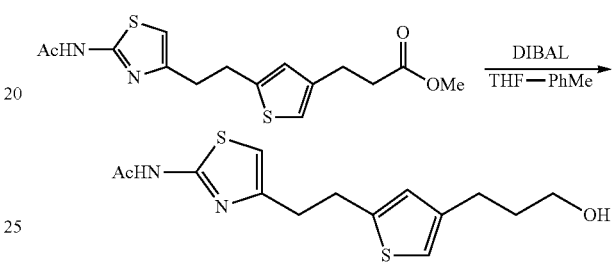

Methyl 3-(5-{2-[2-(acetylamino)-1,3-thiazol-2-yl]ethyl}thiophen-3-yl)propionate (845.0 mg, 2.497 mmol) was reduced by a method similar to that of Production Example 15, step 8, to give. N-(4-{2-[4-(3-hydroxypropyl)thiophen-2-yl]ethyl}-1,3-thiazol-2-yl)acetamide (555.1 mg, 1.788 mmol, yield 71.6%) as an off-white solid.

Step 7

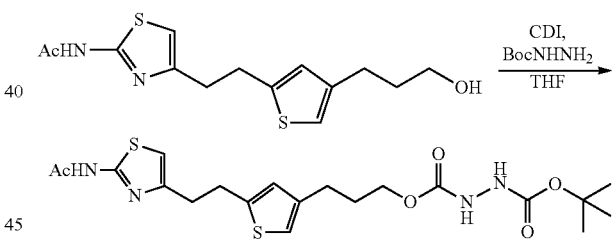

In a similar manner as in Production Example 2, step 1, 3-(5-{2-[2-(acetylamino)-1,3-thiazol-4-yl]ethyl}thiophen-3-yl)propyl tert-butyl hydrazine-1,2-dicarboxylate (277.4 mg, 0.592 mmol, yield 99.5%) was obtained as a pale-yellow solid from N-(4-{2-[4-(3-hydroxypropyl)thiophen-2-yl]ethyl}-1,3-thiazol-2-yl)acetamide (184.6 mg, 0.595 mmol).

Step 8

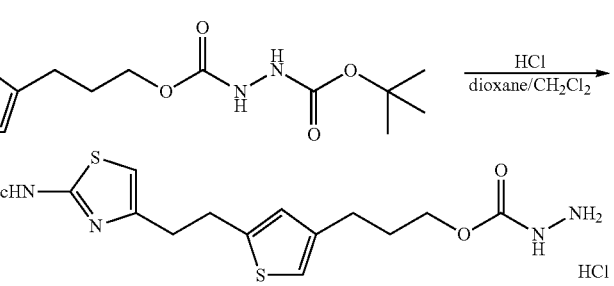

In a similar manner as in Production Example 2, step 2, the title compound (238.4 mg, 0.589 mmol, yield 99.7%) was obtained as a white solid from 3-(5-{2-[2-(acetylamino)-1,3-thiazol-4-yl]ethyl}thiophen-3-yl)propyl tert-butyl hydrazine-1,2-dicarboxylate (277.0 mg, 0.591 mmol).

melting point 98-102° C.

$^1$H-NMR (200 MHz, DMSO-d6): δ(ppm):12.07(1H, brs), 10.6-9.6(3H, br), 6.90(1H, s), 6.76(1H, s), 6.71(1H, s), 4.09 (2H, t, J=6.6 Hz), 3.09(2H, t, J=7.3 Hz), 2.88(2H, t, J=7.3 Hz), 2.55(2H, t, J=6.6 Hz), 2.10(3H, s), 1.85(2H, quint, J=6.6 Hz)

$^{13}$C-NMR (50 MHz, DMSO-d6): δ(ppm):168.4, 158.03, 157.79, 149.8, 144.1, 141.0, 126.0, 118.6, 108.0, 65.4, 33.17, 33.15, 29.1, 26.1, 22.7

MS(ESI+):369.1047[M(free)+H]$^+$, 391.0864[M(free)+Na]$^+$

Production Example 17

3-(5-{2-[2-(acetylamino)-1,3-thiazol-4-yl]ethyl}-3-methylthiophen-2-yl)propyl hydrazinecarboxylate hydrochloride Step 1

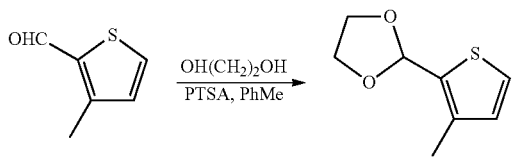

To a solution of 3-methylthiophene-2-carbaldehyde (3.53 g, 28.0 mmol) in toluene (75 ml) were added ethylene glycol (31.2 ml, 560 mmol) and a catalytic amount of para toluenesulfonic acid. The mixture was heated under reflux for 17 hr while separating generated water using Dean-Stark trap. The reaction mixture was cooled to room temperature, washed with saturated aqueous sodium hydrogen carbonate and saturated brine, and concentrated under reduced pressure. The residue was purified by silica gel column chromatography (Merck 7734 80 g, ethyl acetate:hexane=1:10) to give 2-(3-methylthiophen-2-yl)-1,3-dioxolane (3.93 g, 23.1 mmol, yield 82.5%) as a pale-yellow oil.

Step 2

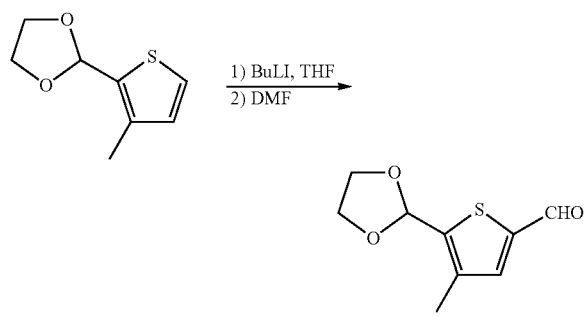

To a solution of 2-(3-methylthiophen-2-yl)-1,3-dioxolane (3.198 g, 18.79 mmol) in anhydrous tetrahydrofuran (30 ml) was added dropwise 1.55M butyllithium hexane solution (12.1 ml, 18.8 mmol) at −78° C. After stirring for 30 min, anhydrous N,N-dimethylformamide (4.36 ml, 56.3 mmol) was added dropwise. After stirring at −78° C. for 1 hr, the reaction mixture was warmed, saturated aqueous ammonium chloride was added, and the mixture was extracted twice with ethyl acetate. The combined organic layer was washed with saturated brine, dried over anhydrous magnesium sulfate and concentrated under reduced pressure, and the residue was purified by silica gel column chromatography (FUJI SILYSIA CHEMICAL LTD. BW-300SP 80 g, ethyl acetate:hexane=1:5) to give 5-(1,3-dioxolan-2-yl)-4-methylthiophene-2-carbaldehyde (3.309 g, 16.69 mmol, yield 88.8%) as a brown oil.

Step 3

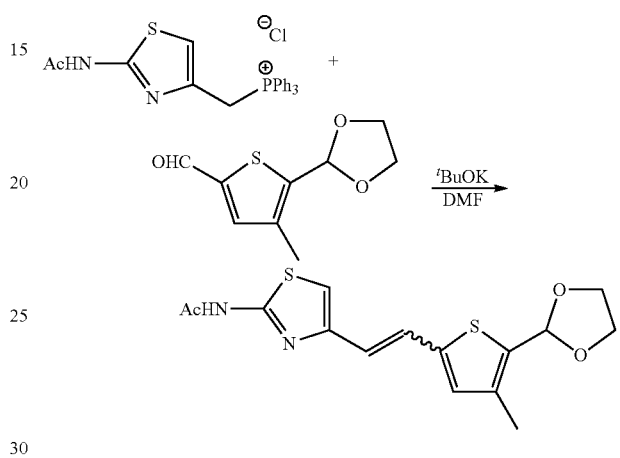

In a similar manner as in Production Example 16, step 1, {[2-(acetylamino)-1,3-thiazol-4-yl]methyl}(triphenyl)phosphonium chloride (12.03 g, 26.56 mmol) and 5-(1,3-dioxolan-2-yl)-4-methylthiophene-2-carbaldehyde (3.51 g, 17.7 mmol) were condensed to give N-(4-{2-[5-(1,3-dioxolan-2-yl)-4-methylthiophen-2-yl]vinyl}-1,3-thiazol-2-yl)acetamide (4.450 g, 13.23 mmol, yield 74.7%) as a yellow solid.

Step 4

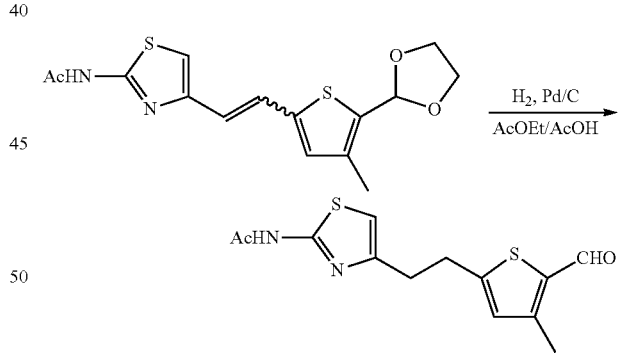

N-(4-{2-[5-(1,3-Dioxolan-2-yl)-4-methylthiophen-2-yl]vinyl}-1,3-thiazol-2-yl)acetamide (4.42 g, 13.1 mmol) was dissolved in a mixture of ethyl acetate (400 ml) and acetic acid (100 ml), and 10% palladium carbon (2.21 g, containing 50% water) was added. The mixture was hydrogenated at room temperature under an atmospheric pressure. The reaction mixture was filtered through celite, and the filtrate was concentrated. The residue was purified by silica gel column chromatography (FUJI SILYSIA CHEMICAL LTD. BW-300SP 200 g, ethyl acetate:dichloromethane=1:6) to give N-{4-[2-(5-formyl-4-methylthiophen-2-yl)ethyl]-1,3-thiazol-2-yl}acetamide (2.26 g, 7.68 mmol, yield 58.4%) as a yellow solid.

Step 5

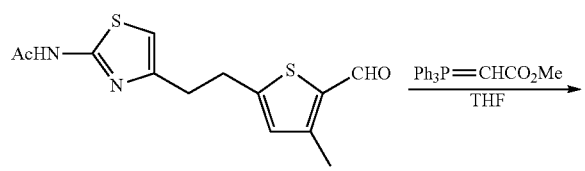

To a solution of N-{4-[2-(5-formyl-4-methylthiophen-2-yl)ethyl]-1,3-thiazol-2-yl}acetamide (468.0 mg, 1.590 mmol) in chloroform (4.7 ml) was added dropwise a solution of methyl (triphenyl phosphoranylidene)acetate (797.4 mg, 2.385 mmol) in chloroform (2 ml) at 0° C. The mixture was allowed to warm to room temperature and stirred for 2 hr. The reaction mixture was concentrated under reduced pressure, and the residue was purified by silica gel column chromatography (Merck 9385 60 g, ethyl acetate:dichloromethane=1:8) to give methyl (2E)-3-(5-{2-[2-(acetylamino)-1,3-thiazol-4-yl]ethyl}-3-methylthiophen-2-yl)-2-propenoate (591.6 mg, containing triphenylphosphineoxide) as a pale-yellow solid.

Step 6

To a solution of methyl (2E)-3-(5-{2-[2-(acetylamino)-1,3-thiazol-4-yl]ethyl}-3-methylthiophen-2-yl)-2-propenoate (corresponding to 1.590 mmol) in ethyl acetate (30 ml) was added 10% palladium carbon (296 mg, containing 50% water). The mixture was hydrogenated at room temperature under an atmospheric pressure. The reaction mixture was filtered through celite, and the filtrate was concentrated under reduced pressure to give methyl 3-(5-{2-[2-(acetylamino)-1,3-thiazol-4-yl]ethyl}-3-methylthiophen-2-yl)-2-propionate (376.9 mg, 1.069 mmol, total yield from step 5, 67.2%).

Step 7

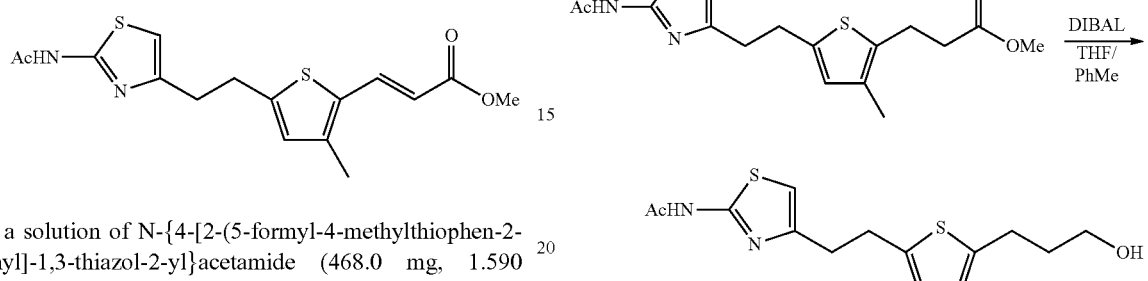

Methyl 3-(5-{2-[2-(acetylamino)-1,3-thiazol-4-yl]ethyl}-3-methylthiophen-2-yl)-2-propionate (214.7 mg, 0.609 mmol) was reduced by a method similar to that of Production Example 15, step 8, to give N-(4-{2-[5-(3-hydroxypropyl)-4-methylthiophen-2-yl]ethyl}-1,3-thiazol-2-yl)acetamide (105.9 mg, 0.326 mmol, yield 53.6%) as a white solid.

Step 8

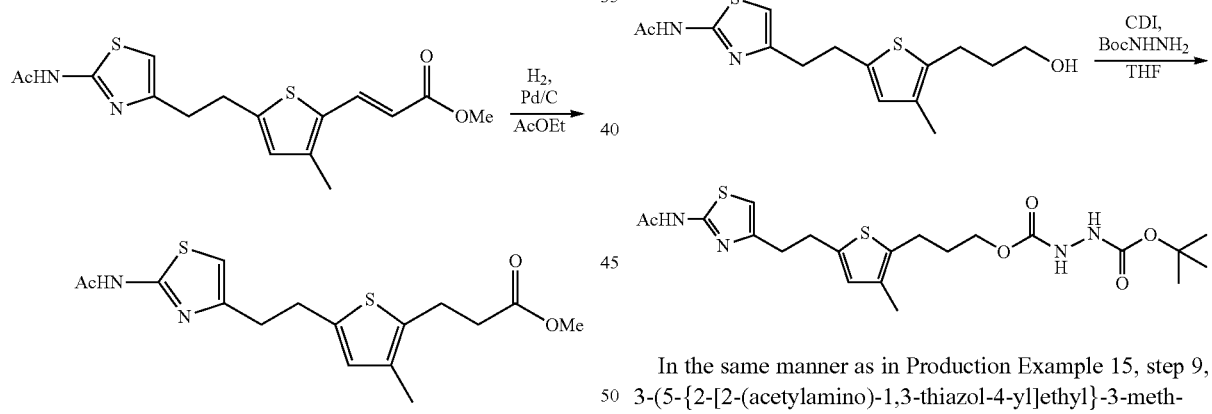

In the same manner as in Production Example 15, step 9, 3-(5-{2-[2-(acetylamino)-1,3-thiazol-4-yl]ethyl}-3-methylthiophen-2-yl)propyl tert-butyl hydrazine-1,2-dicarboxylate (155.7 mg, 0.323 mmol, yield 90.7%) was obtained as a white solid from N-(4-{2-[5-(3-hydroxypropyl)-4-methylthiophen-2-yl]ethyl}-1,3-thiazol-2-yl)acetamide (115.6 mg, 0.356 mmol).

Step 9

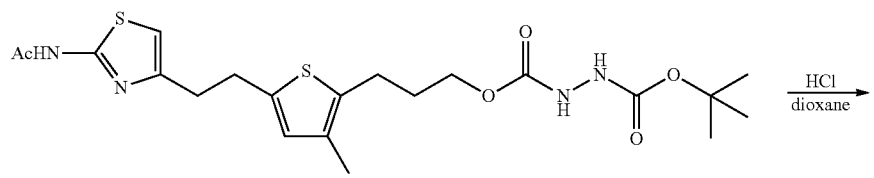

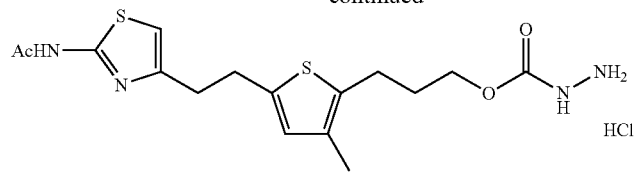

3-(5-{2-[2-(Acetylamino)-1,3-thiazol-4-yl]ethyl}-3-methylthiophen-2-yl)propyl tert-butyl hydrazine-1,2-dicarboxylate (155.7 mg, 0.323 mmol) was deprotected by a method similar to that of Production Example 15, step 10, to give the title compound (112.3 mg, 0.258 mmol, yield 79.9%) as a pale-yellow solid.

melting point 111-115° C.

$^1$H-NMR (400 MHz, DMSO-d6): δ(ppm):12.05(1H, brs), 10.8-9.8(4H, br), 6.75(1H, s), 6.53(1H, s), 4.09(2H, t, J=6.4 Hz), 3.00(2H, t, J=7.6 Hz), 2.84(2H, t, J=7.6 Hz), 2.67(2H, t, J=7.5 Hz), 2.10(3H, s), 2.01(3H, s), 1.80(2H, tt, J=7.5, 7.6 Hz)

$^{13}$C-NMR (100 MHz, DMSO-d6): δ(ppm): 168.2, 157.5, 155.8, 149.7, 139.6, 134.0, 132.2, 127.5, 107.7, 64.9, 32.9, 30.2, 28.8, 23.3, 22.5, 13.3

MS(ESI+):383.1227[M(free)+H]$^+$, 405.1058[M(free)+Na]$^+$

Production Example 18

N-(4-{2-[2-(acetylamino)-1,3-thiazol-4-yl]ethyl}benzyl)hydrazinecarboxamide hydrochloride Step 1

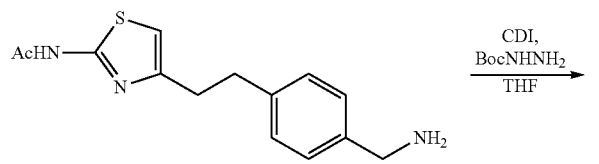

To a suspension of 1,1'-carbonyldiimidazole (332.1 mg, 2.048 mmol) in anhydrous tetrahydrofuran (1.3 ml) was added tert-butyl carbazate (270.7 mg, 2.048 mmol). After stirring at room temperature for 15 min, N-(4-{2-[4-(aminomethyl)phenyl]ethyl}-1,3-thiazol-2-yl)acetamide (282.6 mg, 1.024 mmol) was added, and the mixture was stirred at room temperature for 6 hr and concentrated under reduced pressure. Ethyl acetate and water were added to the residue, and the mixture was stirred, stood still and then partitioned. The aqueous layer was extracted with ethyl acetate, and the combined organic layer was washed with saturated brine, dried over anhydrous magnesium sulfate and concentrated under reduced pressure. The residue was purified by silica gel column chromatography (FUJI SILYSIA CHEMICAL LTD. BW-300SP 24 g, dichloromethane:methanol=30:1→20:1). The residue was further purified by silica gel column chromatography (FUJI SILYSIA CHEMICAL LTD. DM-2035 16 g, dichloromethane:methanol=30:1) to give tert-butyl 2-[(4-{2-[2-(acetylamino)-1,3-thiazol-4-yl]ethyl}benzyl)carbamoyl]hydrazinecarboxylate (348.3 mg, 0.803 mmol, yield 78.5%) as a white solid.

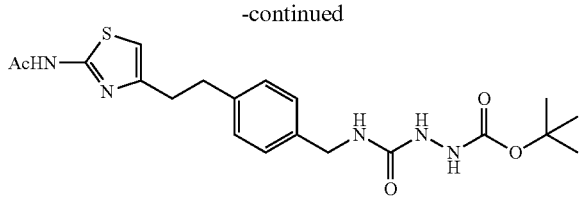

Step 2

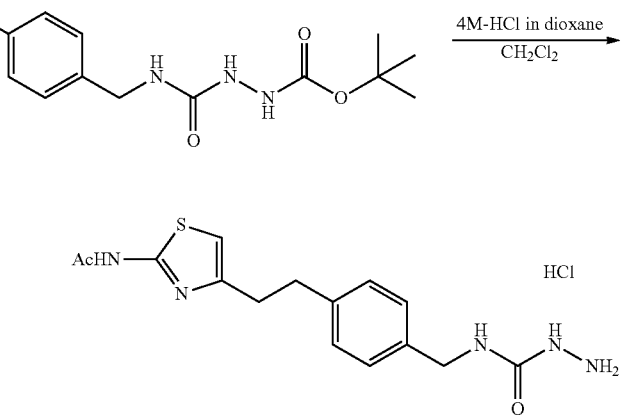

To a suspension of tert-butyl 2-[(4-{2-[2-(acetylamino)-1,3-thiazol-4-yl]ethyl}benzyl)carbamoyl]hydrazinecarboxylate (281.8 mg, 0.65 mmol) in anhydrous dichloromethane (3.25 ml) was added 4M-hydrogen chloride dioxane solution (3.25 ml, 13.0 mmol). After stirring at room temperature for 1 hr, the reaction mixture was concentrated under reduced pressure. Ethyl acetate was added to the residue, and the mixture was concentrated again under reduced pressure. The operation was performed 3 times to remove hydrogen chloride gas azeotropically. The residue was suspended in ethyl acetate and filtered. The filtered product was washed with ethyl acetate, and dried under reduced pressure to give the title compound (245.1 mg, quantitative) as a white solid.

melting point 167-169° C.

$^1$H-NMR (200 MHz, DMSO-d6): δ(ppm):12.08(1H, brs), 9.92(3H, brs), 8.87(1H, brs), 7.53(1H, t, J=5.7 Hz), 7.22-7.04 (4H, m), 6.71(1H, s), 4.22(2H, d, J=5.7 Hz), 2.98-2.75(4H, m), 2.10(3H, s)

$^{13}$C-NMR (50 MHz, DMSO-d6): δ(ppm):168.5, 157.7, 157.5, 150.3, 140.2, 137.3, 128.4, 127.3, 107.6, 42.8, 34.3, 33.0, 22.7

MS(ESI+):334.1316[M(free)+H]$^+$, 356.1129[M(free)+Na]$^+$

Production Example 19

N-[2-(4-{2-[2-(acetylamino)-1,3-thiazol-4-yl]ethyl}phenyl)ethyl]hydrazinecarboxamide hydrochloride Step 1

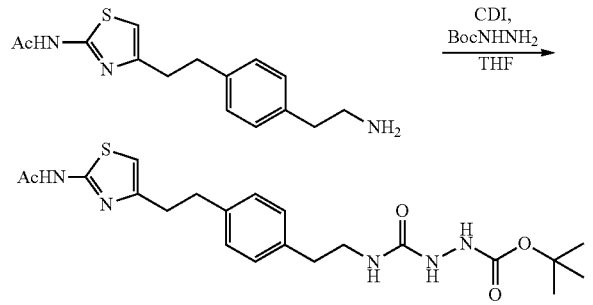

In a similar manner as in Production Example 3, step 1, tert-butyl 2-{[2-(4-{2-[2-(acetylamino)-1,3-thiazol-4-yl]ethyl}phenyl)ethyl]carbamoyl}hydrazinecarboxylate (674.7 mg, 1.508 mmol, yield 88.7%) was obtained as a white solid from N-(4-{2-[4-(2-aminoethyl)phenyl]ethyl}-1,3-thiazol-2-yl)acetamide (492.0 mg, 1.700 mmol).

Step 2

In a similar manner as in Production Example 3, step 2, the title compound (422.1 mg, 1.100 mmol, yield 95.8%) was obtained as a white solid from tert-butyl 2-{[2-(4-{2-[2-(acetylamino)-1,3-thiazol-4-yl]ethyl}phenyl)ethyl]carbamoyl}hydrazinecarboxylate (513.8 mg, 1.148 mmol).

melting point 171-173° C.

$^1$H-NMR (200 MHz, DMSO-d6): δ(ppm):12.12(1H, brs), 10.00(3H, brs), 8.82(1H, brs), 7.30-6.96(4H, m), 6.73(1H, s), 3.39-3.18(2H, m), 2.97-2.77(4H, m), 2.66(2H, t, J=7.2 Hz), 2.10(2H, s)

$^{13}$C-NMR (50 MHz, DMSO-d6): δ(ppm):168.5, 157.7, 157.3, 150.3, 139.4, 136.8, 128.8, 128.5, 107.6, 35.4, 34.4, 32.9, 22.7

MS(ESI+):348.1490[M(free)+H]$^+$, 370.1307[M(free)+Na]$^+$

Production Example 20

N-(4-{2-[2-(acetylamino)-1,3-thiazol-4-yl]ethyl}-2-fluorobenzyl)hydrazinecarboxamide hydrochloride Step 1

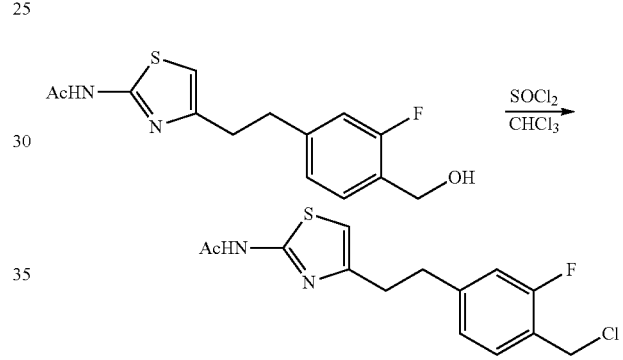

To a solution of N-(4-{2-[3-fluoro-4-(hydroxymethyl)phenyl]ethyl}-1,3-thiazol-2-yl)acetamide (196.6% mg, 0.668 mmol) in chloroform (10 ml) was added thionyl chloride (0.144 ml, 2.00 mmol), and the mixture was stirred at room temperature for 1 hr. Thionyl chloride (0.077 ml, 1.00 mmol) was added, and the mixture was stirred at room temperature for 1 hr and concentrated. Ethyl acetate (10 ml) was added to the residue, and the mixture was concentrated again under reduced pressure. The operation was performed 3 times to

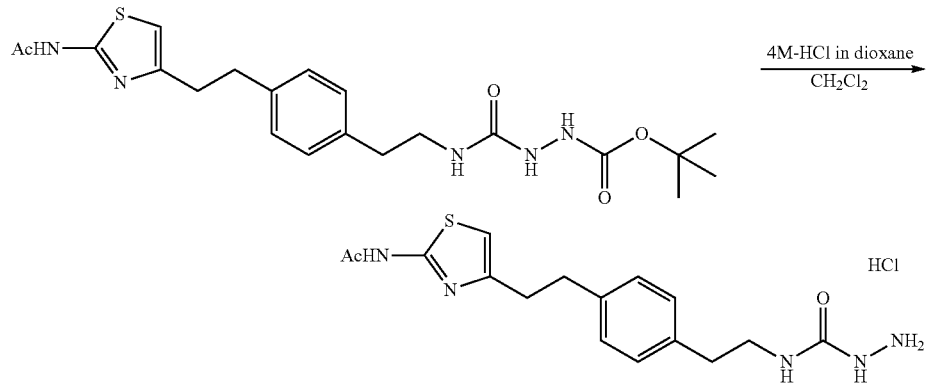

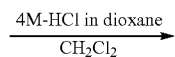

remove thionyl chloride azeotropically. A mixture of ethyl acetate (1 ml) and diisopropyl ether (10 ml) was added to the residue, and the precipitate was collected by filtration and dried under reduced pressure to give N-(4-{2-[4-(chloromethyl)-3-fluorophenyl]ethyl}-1,3-thiazol-2-yl)acetamide (205.3 mg, 0.656 mmol, yield 98.3%) as a slightly yellow solid.

Step 2

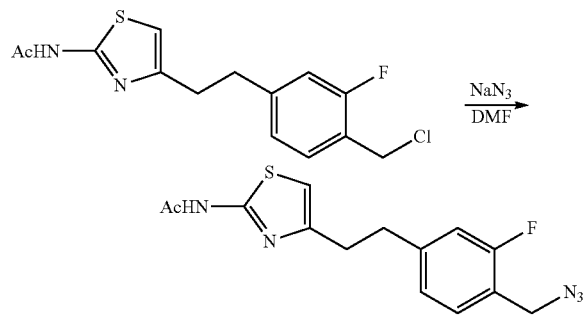

To a solution of N-(4-{2-[4-(chloromethyl)-3-fluorophenyl]ethyl}-1,3-thiazol-2-yl)acetamide (203.3 mg, 0.650 mmol) in anhydrous N,N-dimethylformamide (2 ml) was added sodium azide (233.7 mg, 3.595 mmol), and the mixture was stirred at room temperature for 3.5 hr. Water (20 ml) and ethyl acetate (20 ml) were added to the reaction mixture, and the mixture was stirred, stood still and then partitioned. The aqueous layer was extracted with ethyl acetate, and the combined organic layer was washed with water and saturated brine, dried over anhydrous magnesium sulfate, and concentrated under reduced pressure. Diisopropyl ether (10 ml) was added to the residue, and the mixture was filtered and dried under reduced pressure to give N-(4-{2-[4-(azidomethyl)-3-fluorophenyl]ethyl}-1,3-thiazol-2-yl)acetamide (160.5 mg, 0.503 mmol, yield 77.3%) as a white solid.

Step 3

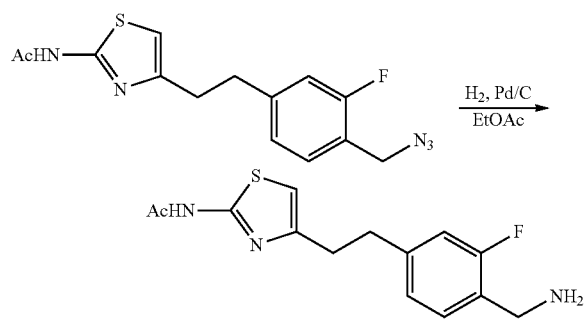

To a solution of N-(4-{2-[4-(azidomethyl)-3-fluorophenyl]ethyl}-1,3-thiazol-2-yl)acetamide (152.3 mg, 0.477 mmol) in ethyl acetate (21 ml) was added 10% palladium carbon (30.5 mg, containing 50% water), and the mixture was hydrogenated at room temperature under an atmospheric pressure. Ethyl acetate (5 ml) and methanol (5 ml) were added to the reaction mixture, and the mixture was filtered through celite. The filtrate was concentrated under reduced pressure, and the resulting solid was collected by filtration, washed with tert-butyl methyl ether (5 ml) and dried under reduced pressure to give N-(4-{2-[4-(aminomethyl)-3-fluorophenyl]ethyl}-1,3-thiazol-2-yl)acetamide (119.3 mg, 0.407 mmol, yield 85.3%) as a white solid.

Step 4

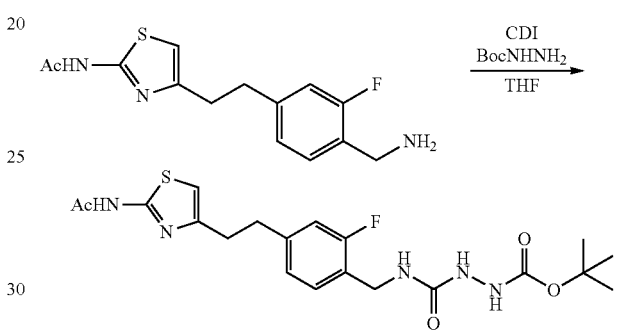

To a suspension of 1,1'-carbonyldiimidazole (129.7 mg, 0.800 mmol) in anhydrous tetrahydrofuran (0.8 ml) was added tert-butyl carbazate (105.7 mg, 0.800 mmol), and the mixture was stirred at room temperature for 15 min. N-(4-{2-[4-(Aminomethyl)-3-fluorophenyl]ethyl}-1,3-thiazol-2-yl)acetamide(114.2 mg, 0.389 mmol) was added, and the mixture was stirred at room temperature for 3 hr. Ethyl acetate (15 ml), water (12 ml) and 1M hydrochloric acid (3 ml) were added to the reaction mixture and the mixture was stirred. The mixture was stood still and partitioned, and the organic layer was washed with water (15 ml) and saturated brine (15 ml), dried over anhydrous magnesium sulfate and concentrated under reduced pressure. The residue was suspended in a mixture of ethyl acetate (5 ml) and hexane (5 ml), and the suspension was filtered and dried under reduced pressure to give tert-butyl 2-[(4{2-[2-(acetylamino)-1,3-thiazol-4-yl]ethyl}-2flouorobenzyl)carbamoyl]hydrazinecarboxylate(150.0 mg, 0.332 mmol, yield 85.3%) as a white solid.

Step 5

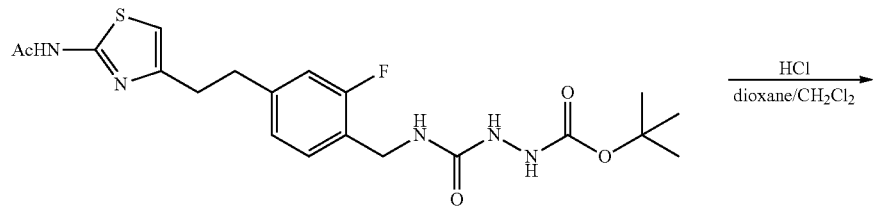

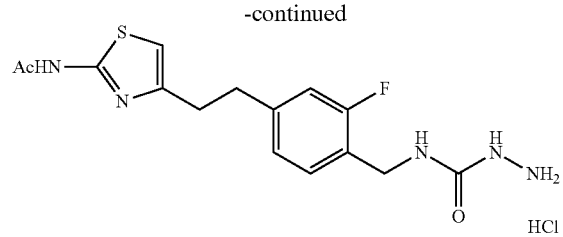

To a suspension of tert-butyl 2-[(4-{2-[2-(acetylamino)-1,3-thiazol-4-yl]ethyl}-2-fluorobenzyl)carbamoyl]hydrazinecarboxylate (141.6 mg, 0.314 mmol) in anhydrous dichloromethane (2 ml) was added 4M hydrogen chloride dioxane solution (2 ml). The mixture was stirred at room temperature for 2 hr, and concentrated under reduced pressure. Ethyl acetate (10 ml) was added to the residue, and the mixture was concentrated again under reduced pressure. This operation was repeated 3 times to remove hydrogen chloride gas azeotropically. The residue was suspended in a mixture of ethanol (2 ml) and ethyl acetate (4 ml), filtered, washed twice with ethyl acetate, and dried under reduced pressure to give N-(4-{2-[2-(acetylamino)-1,3-thiazol-4-yl]ethyl}-2-fluorobenzyl)hydrazinecarboxamide hydrochloride (123.6 mg, 0.319 mmol, quantitative) as a white solid.

melting point 172-175° C.

$^1$H-NMR (400 MHz, DMSO-d6): δ (ppm): 12.08(1H, brs), 9.96(3H, brs), 8.91(1H, brs), 7.53(1H, t, J=5.7 Hz), 7.23(1H, t, J=8.0 Hz), 7.03-6.99 (2H, m), 6.74(1H, s), 4.27(2H, d, J=5.7 Hz), 2.96-2.85(4H, m), 2.12(3H, s)

$^{13}$C-NMR (100 MHz, DMSO-d6): δ (ppm):168.2, 159.7(d, J=243.9 Hz), 157.4, 157.1, 149.8, 142.9(d, J=7.5 Hz), 129.1 (d, J=4.5 Hz), 124.0(d, J=3.0 Hz), 123.4(d, J=14.9 Hz), 114.7 (d, J=20.9 Hz), 107.4, 36.6(d, J=3.8 Hz), 33.7, 32.2, 22.4

$^{19}$F-NMR (376 Hz, DMSO-d6): δ (ppm):−121.0

MS(ESI+):352.1183[M(free)+H]$^+$, 374.1003[M(free)+Na]$^+$

Production Example 21

N-(4-{2-[2-(acetylamino)-1,3-thiazol-4-yl]ethyl}-3-fluorobenzyl)hydrazinecarboxamide hydrochloride Step 1

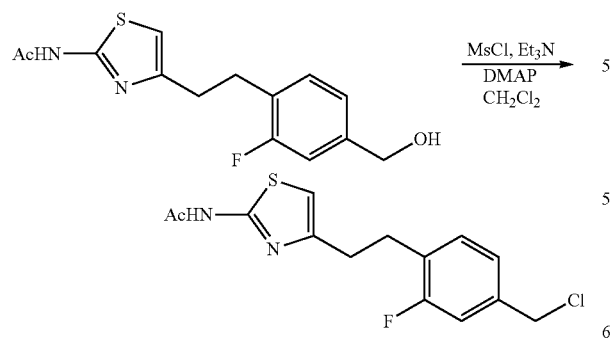

To a solution of N-(4-{2-[2-fluoro-4-(hydroxymethyl)phenyl]ethyl}-1,3-thiazol-2-yl)acetamide (194.7 mg, 0.665 mmol) in anhydrous dichloromethane (2 ml) were added triethylamine (0.17 ml, 1.20 mmol) and 4-dimethylaminopyridine (8.1 mg, 0.066 mmol), and the mixture was cooled to 0° C. Methanesulfonyl chloride (77 μl, 1.0 mmol) was added dropwise, and the mixture was stirred at room temperature for 1 hr. The mixture was cooled to 0° C., triethylamine (93 μl, 0.67 mmol) and methanesulfonyl chloride (51 μl, 0.67 mmol) were added, and the mixture was stirred at room temperature for 5 min. Iced water (2 ml) was added to the reaction mixture, and the mixture was stood still and partitioned. The aqueous layer was extracted 3 times with dichloromethane, and the combined organic layer was washed with 1M hydrochloric acid and saturated brine, dried over anhydrous magnesium sulfate, and concentrated under reduced pressure. The concentrated residue was purified by silica gel column chromatography (Merck 9385 16 g, ethyl acetate:hexane=2:3) to give N-(4-{2-[4-(chloromethyl)-2-fluorophenyl]ethyl}-1,3-thiazol-2-yl)acetamide (59.6 mg, 0.191 mmol, yield 28.7%) as a pale-yellow solid.

Step 2

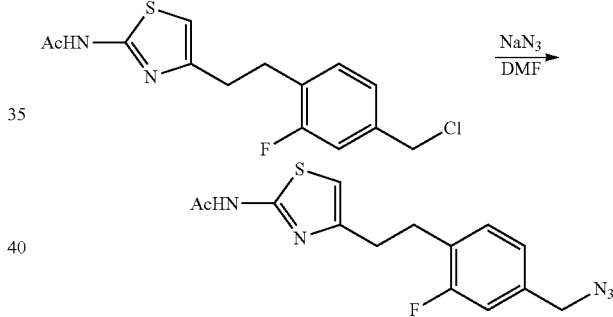

N-(4-{2-[4-(Chloromethyl)-2-fluorophenyl]ethyl}-1,3-thiazol-2-yl)acetamide (59.1 mg, 0.189 mmol) was azidated by a method similar to that of Production Example 20, step 2, to give N-(4-{2-[4-(azidomethyl)-2-fluorophenyl]ethyl}-1,3-thiazol-2-yl)acetamide (54.8 mg, 0.172 mmol, yield 91.0%) as a pale-yellow solid.

Step 3

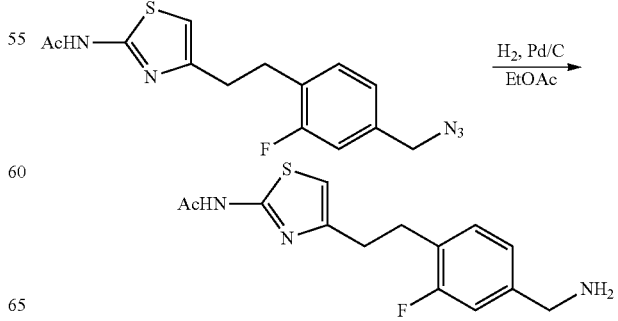

N-(4-{2-[4-(Azidomethyl)-2-fluorophenyl]ethyl}-1,3-thiazol-2-yl)acetamide (54.0 mg, 0.169 mmol) was hydrogenated by a method similar to that of Production Example 20, step 3, to give N-(4-{2-[4-(aminomethyl)-2-fluorophenyl]ethyl}-1,3-thiazol-2-yl)acetamide (48.8 mg, 0.166 mmol, yield 98.2%) as a white solid.

Step 4

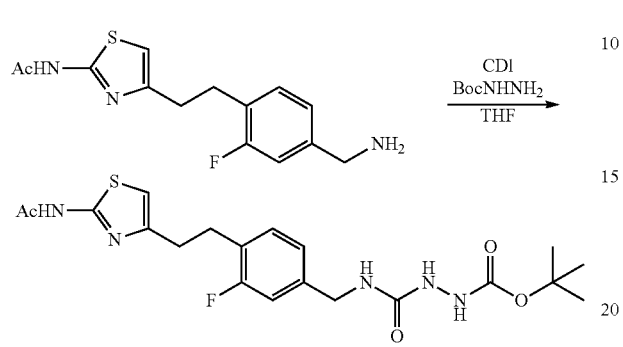

In a similar manner as in Production Example 20, step 3, tert-butyl 2-[(4-{2-[2-(acetylamino)-1,3-thiazol-4-yl]ethyl}-3-fluorobenzyl)carbamoyl]hydrazinecarboxylate (28.7 mg, 0.064 mmol, yield 38.3%) was obtained as a pale-yellow solid from N-(4-{2-[4-(aminomethyl)-2-fluorophenyl]ethyl}-1,3-thiazol-2-yl)acetamide (53.1 mg, 0.327 mmol).

Step 5

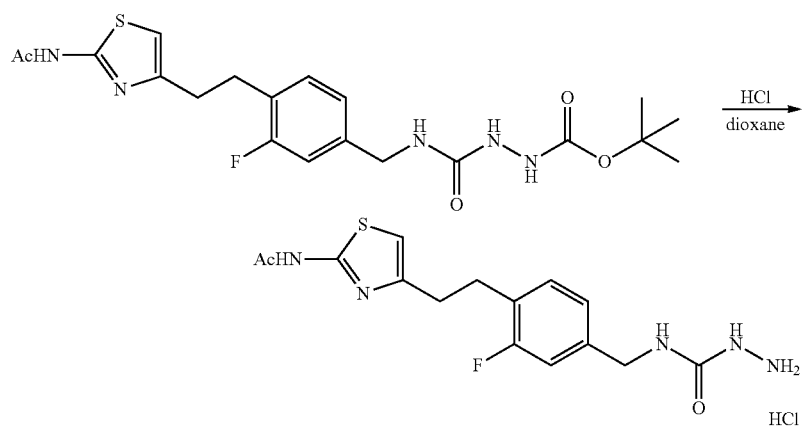

To a solution of tert-butyl 2-[(4-{2-[2-(acetylamino)-1,3-thiazol-4-yl]ethyl}-3-fluorobenzyl)carbamoyl]hydrazinecarboxylate (12.3 mg, 0.027 mmol) in dioxane (1.2 ml) was added 4M hydrogen chloride dioxane solution (0.1 ml), and the mixture was stirred at room temperature for 17 hr, and concentrated under reduced pressure. The residue was suspended in ethyl acetate (2 ml), and the mixture was filtered. The filtered product was washed 3 times with ethyl acetate, and dried under reduced pressure to give the title compound (10.2 mg, 0.026 mmol, yield 96.7%) as a white solid.

melting point 165-169° C.

$^1$H-NMR (400 MHz, DMSO-d6): δ(ppm):12.07(1H, brs), 10.5-9.0(3H, br), 8.83(1H, brs), 7.57(1H, t, J=2.0 Hz), 7.27-7.14(1H, m), 7.03-6.98(2H, m), 6.73(1H, s), 4.23(2H, d, J=6.0 Hz), 2.92-2.81(4H, m), 2.10(3H, s)

MS(ESI+):352.1210[M(free)+H]$^+$, 374.1038[M(free)+Na]$^+$

Production Example 22

N-(4-{2-[2-(acetylamino)-1,3-thiazol-4-yl]ethyl}-2,3-difluorobenzyl)hydrazinecarboxamide hydrochloride Step 1

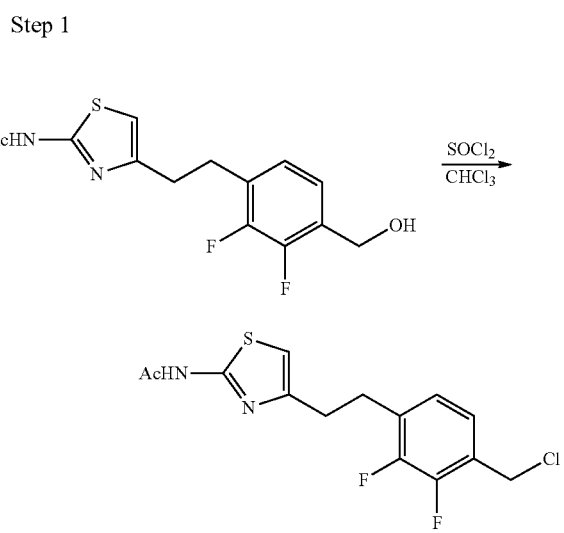

N-(4-{2-[2,3-Difluoro-4-(hydroxymethyl)phenyl]ethyl}-1,3-thiazol-2-yl)acetamide (193.2 mg, 0.619 mmol) was chlorinated by a method similar to that of Production Example 20, step 1, to give N-(4-{2-[4-(chloromethyl)-2,3-difluorophenyl]ethyl}-1,3-thiazol-2-yl)acetamide (212.7 mg) as a white solid.

Step 2

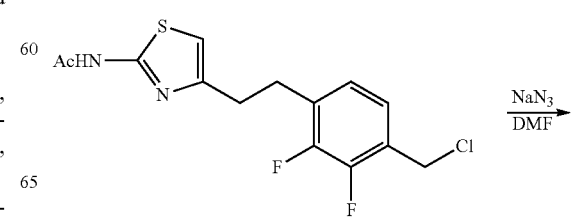

-continued

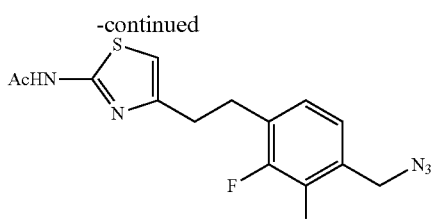

N-(4-{2-[4-(Chloromethyl)-2,3-difluorophenyl]ethyl}-1,3-thiazol-2-yl)acetamide (201.9 mg, 0.610 mmol) was azidated by a method similar to that of Production Example 20, step 2, to give N-(4-{2-[4-(azidomethyl)-2,3-difluorophenyl]ethyl}-1,3-thiazol-2-yl)acetamide (180.3 mg, 0.535 mmol, yield 87.6%) as a white solid.

Step 3

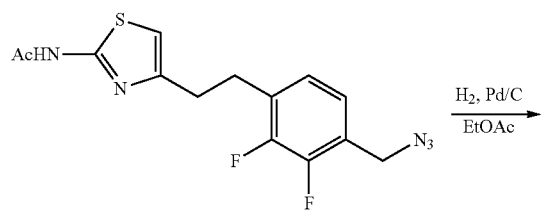

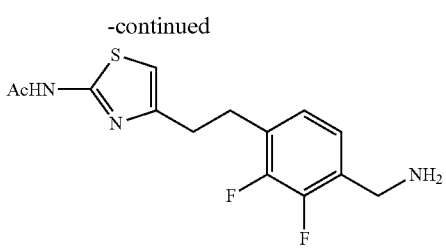

N-(4-{2-[4-(Azidomethyl)-2,3-difluorophenyl]ethyl}-1,3-thiazol-2-yl)acetamide (178.0 mg, 0.528 mmol) was hydrogenated by a method similar to that of Production Example 20, step 3, to give N-(4-{2-[4-(aminomethyl)-2,3-difluorophenyl]ethyl}-1,3-thiazol-2-yl)acetamide (132.1 mg, 0.424 mmol, yield 80.4%) as a white solid.

Step 4

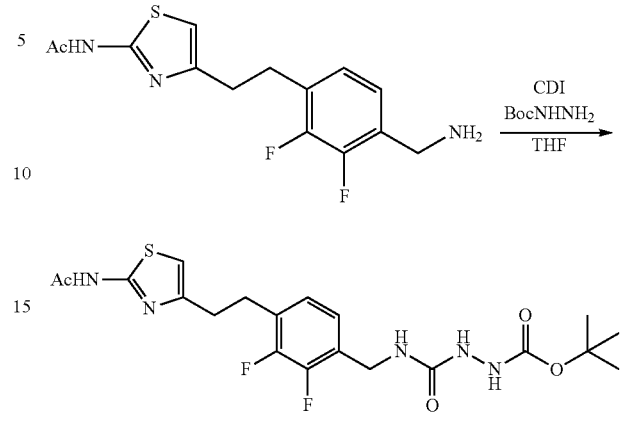

In a similar manner as in Production Example 20, step 4, tert-butyl 2-[(4-{2-[2-(acetylamino)-1,3-thiazol-4-yl]ethyl}-2,3-difluorobenzyl)carbamoyl]hydrazinecarboxylate (135.2 mg, 0.288 mmol, yield 73.7%) was obtained as a white solid from N-(4-{2-[4-(aminomethyl)-2,3-difluorophenyl]ethyl}-1,3-thiazol-2-yl)acetamide (126.7 mg, 0.781 mmol).

Step 5

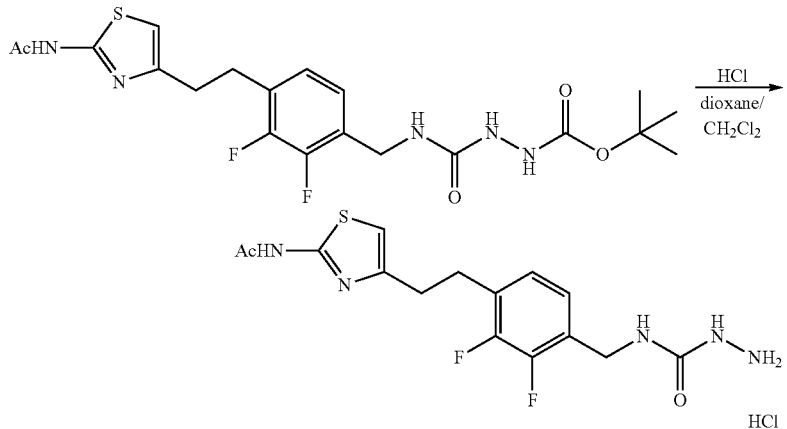

tert-Butyl 2-[(4-{2-[2-(acetylamino)-1,3-thiazol-4-yl]ethyl}-2,3-difluorobenzyl)carbamoyl]hydrazinecarboxylate (130.2 mg, 0.277 mmol) was deprotected by a method similar to that of Production Example 20, step 5, to give the title compound (101.4 mg, 0.250 mmol, yield 90.1%) as a white solid.

melting point 163-166° C.

$^1$H-NMR (400 MHz, DMSO-d6): δ (ppm):12.10(1H, brs), 9.95(3H, brs), 8.96(1H, brs), 7.61(1H, t, J=6.0 Hz), 7.23(1H, t, J=8.0 Hz), 7.08-7.03(2H, m), 6.76(1H, s), 4.31(2H, t, J=5.9 Hz), 2.96-2.85(4H, m), 2.13(3H, s)

$^{13}$C-NMR (100 MHz, DMSO-d6): δ (ppm):168.2, 157.5, 157.1, 149.5, 147.9(dd, J=243.1, 10.5 Hz), 147.5(dd, J=240.1, 7.5 Hz), 128.9(d, J=12.7 Hz), 126.3(d, J=11.2 Hz), 124.8, 123.6, 107.6, 36.5, 31.1, 27.4, 22.4

$^{19}$F-NMR (376 Hz, DMSO-d6): δ (ppm):−146.2(1F, d, $J_{FF}$=19.1 Hz), −146.7(1F, d, $J_{FF}$=19.1 Hz)

MS(ESI+):370.1101[M(free)+H]$^+$, 392.0915[M(free)+Na]$^+$

Production Example 23

N-[4-({[2-(acetylamino)-1,3-thiazol-4-yl]methyl}amino)benzyl]hydrazinecarboxamide dihydrochloride Step 1

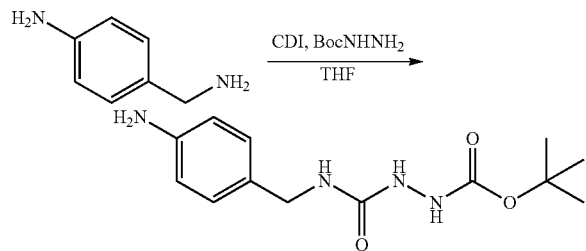

To a suspension of 1,1'-carbonyldiimidazole (1.783 g, 11.00 mmol) in anhydrous tetrahydrofuran (7 ml) was added tert-butyl carbazate (1.322 g, 10.00 mmol), and the mixture was stirred at room temperature for 30 min. A solution of 4-(aminomethyl)aniline (1.228 g, 10.05 mmol) in anhydrous tetrahydrofuran (3 ml) was added, and the mixture was stirred at room temperature for 1 hr. The solvent was evaporated under to reduced pressure, and ethyl acetate (50 ml) and water (50 ml) were added to the residue. The mixture was stirred, stood still and partitioned. The aqueous layer was extracted twice with ethyl acetate, and the combined organic layer was dried over anhydrous magnesium sulfate and concentrated under reduced pressure. The concentrated residue was purified by silica gel column chromatography (FUJI SILYSIA CHEMICAL LTD. BW-300SP 90 g, ethyl acetate:hexane=7:3→8:2→9:1) to give tert-butyl 2-[(4-aminobenzyl)carbamoyl]hydrazinecarboxylate (2.180 g, 7.778 mmol, yield 77.8%) as a white solid.

Step 2

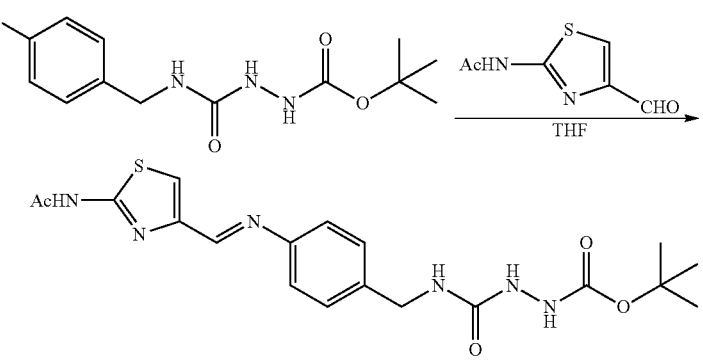

To a solution of tert-butyl 2-[(4-aminobenzyl)carbamoyl]hydrazinecarboxylate (700.7 mg, 2.500 mmol) in anhydrous tetrahydrofuran (10 ml) was added N-(4-formyl-1,3-thiazol-2-yl)acetamide (425.5 mg, 2.500 mmol). The mixture was heated under reflux for 1 hr, cooled to room temperature, and concentrated under reduced pressure. Tetrahydrofuran (5 ml) and tert-butyl methyl ether (10 ml) were added to the residue and the mixture was stirred. The resulting solid was collected by filtration, washed twice with tert-butyl methyl ether and dried under reduced pressure to give tert-butyl 2-{[4-({[2-(acetylamino)-1,3-thiazol-4-yl]methylidene}amino)benzoyl]carbamoyl}hydrazinecarboxylate (1.097 g, quantitative) as a white solid.

Step 3

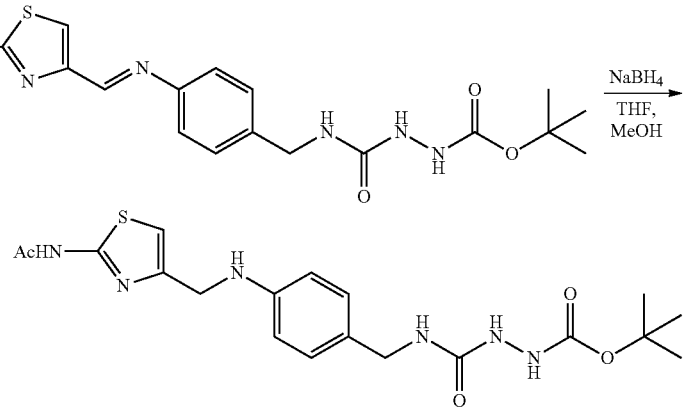

tert-Butyl 2-{[4-({[2-(acetylamino)-1,3-thiazol-4-yl]methylidene}amino)benzoyl]carbamoyl}hydrazinecarboxylate (778.5 mg, 1.800 mmol) was dissolved in a mixed solvent of anhydrous tetrahydrofuran (18 ml) and anhydrous methanol (9 ml), and the mixture was cooled to 0° C. Sodium borohydride (68.1 mg, 1.80 mmol) was added and the mixture was stirred at room temperature for 30 min. Acetic acid (0.22 ml, 3.85 mmol) was added and the mixture was stirred for 15 min and concentrated under reduced pressure. The residue was purified by silica gel column chromatography (FUJI SILYSIA CHEMICAL LTD. BW-300SP 40 g, dichloromethane:methanol=20:1→15:1). The pure fractions were concentrated under reduced pressure, ethyl acetate (30 ml) and tert-butyl methyl ether (10 ml) were added to the residue, and the resulting solid was collected by filtration and dried under reduced pressure to give tert-butyl 2-{[4-({[2-(acetylamino)-1,3-thiazol-4-yl]methyl}amino)benzoyl]carbamoyl}hydrazinecarboxylate (653.1 mg, 1.503 mmol, yield 83.5%) as a white solid.

Step 4

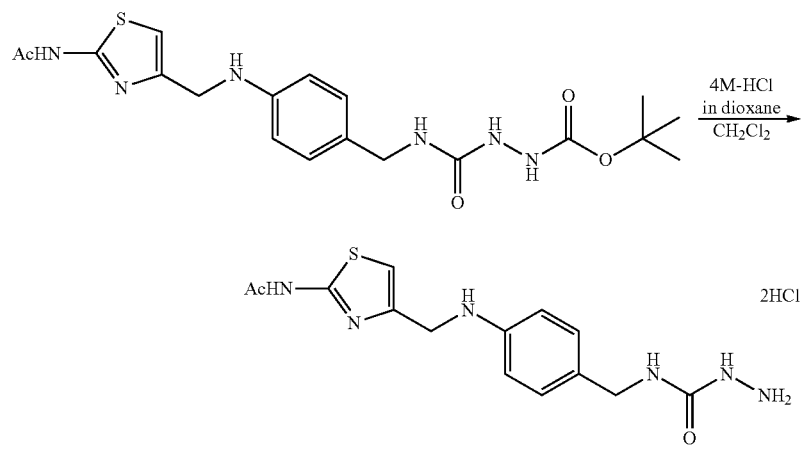

To a suspension of tert-butyl 2-{[4-({[2-(acetylamino)-1,3-thiazol-4-yl]methyl}amino)benzoyl]carbamoyl}hydrazinecarboxylate (306.2 mg, 0.705 mmol) in anhydrous dichloromethane (7 ml) was added 4M hydrogen chloride dioxane solution (7.0 ml, 28.0 mmol). The mixture was stirred at room temperature for 2 hr, and concentrated under reduced pressure. Ethyl acetate was added to the residue, and the mixture was concentrated again under reduced pressure. This operation was repeated 3 times to remove hydrogen chloride azeotropically. The residue was suspended in ethyl acetate, and the suspension was filtered, washed twice with ethyl acetate, and dried under reduced pressure. The residue was recrystallized by dissolving in methanol (3.6 ml) and then addition of ethyl acetate (12 ml). The crystals were collected by filtration, and dried under reduced pressure to give the title compound (272.8 mg, 0.670 mmol, yield 95.0%) as a white solid.

$^1$H-NMR (200 MHz, DMSO-d6): δ(ppm):12.07(1H, brs), 9.87(3H, brs), 8.75(1H, brs), 7.40(1H, t, J=5.7 Hz), 7.06(2H, d, J=8.2 Hz), 6.93(1H, s), 6.74(2H, d, J=8.2 Hz), 4.27(2H, s), 4.12(2H, J=5.7 Hz), 2.11(3H, s)

$^{13}$C-NMR (50 MHz, D$_2$O): δ(ppm):174.6, 162.2, 160.8, 143.1, 142.2, 135.8, 131.2, 125.7, 119.1, 57.1, 53.1, 24.9

MS(ESI+):335.1293[M(free)+H]$^+$

Production Example 24

2-(acetylamino)-N-(4-{[[hydrazinocarbonyl)amino]methyl}phenyl)-1,3-thiazole-4-carboxamide hydrochloride Step 1

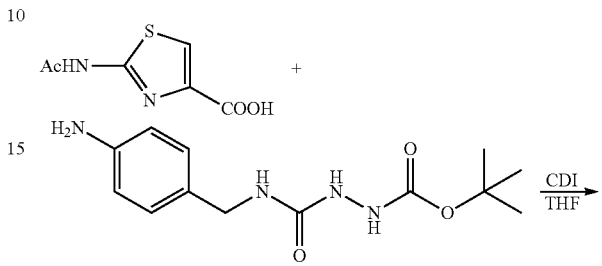

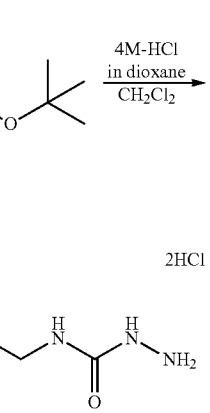

-continued

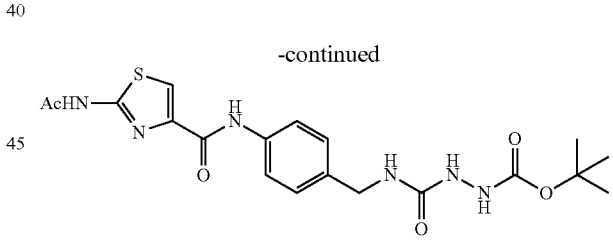

To a suspension of 2-(acetylamino)-1,3-thiazole-4-carboxylic acid (558.6 mg, 3.000 mmol) in anhydrous tetrahydrofuran (10 ml) were added 1,1'-carbonyldiimidazole (535.2 mg, 3.301 mmol) and anhydrous tetrahydrofuran (10 ml), and the mixture was stirred at 50° C. for 2 hr. tert-Butyl 2-[(4-aminobenzyl)carbamoyl]hydrazinecarboxylate (841.0 mg, 3.000 mmol) was added, and the mixture was stirred for 24 hr. To a solution of 2-(acetylamino)-1,3-thiazole-4-carboxylic acid (280.2 mg, 1.505 mmol) in anhydrous N,N-dimethylformamide (5 ml) was added 1,1'-carbonyldiimidazole (243.2 mg, 1.500 mmol), and the mixture was stirred at 50° C. for 30 min. This solution was added to the mixture obtained above, and the mixture was stirred at 50° C. for 3 hr, and at room temperature for 65 hr. Water and ethyl acetate were added to the reaction mixture and the mixture was stirred. The precipitated solid was filtered, washed with ethyl acetate, and dried under reduced pressure to give tert-butyl 2-{[4-({[2-(acetylamino)-1,3-thiazol-4-yl]carbonyl}amino)benzyl]carbamoyl}hydrazinecarboxylate (1.223 g, 2.728 mmol, yield 90.9%) as a white solid.

Step 2

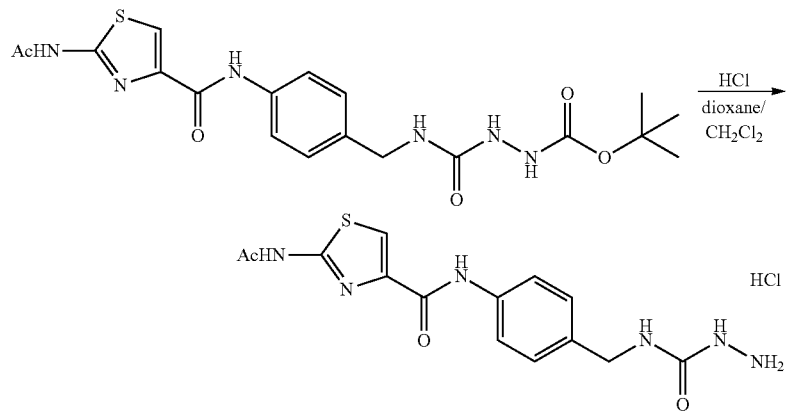

tert-Butyl 2-{[4-({[2-(acetylamino)-1,3-thiazol-4-yl]carbonyl}amino)benzyl]carbamoyl}hydrazinecarboxylate (298.0 mg, 0.664 mmol) was deprotected by a method similar to that of Production Example 20, step 5, to give the title compound (257.4 mg, quantitative) as a white solid.

melting point 231-234° C.

$^1$H-NMR (400 MHz, DMSO-d6): δ (ppm):12.33(1H, brs), 9.83(3H, brs), 9.72(1H, brs), 8.80(1H, brs), 7.93(1H, s), 7.68 (2H, d, J=8.6 Hz), 7.52(1H, t, J=5.9 Hz), 7.25 (2H, d, J=8.6 Hz), 4.24(2H, d, J=5.9 Hz), 2.18(3H, s)

$^{13}$C-NMR (100 MHz, DMSO-d6): δ (ppm):169.2, 159.3, 158.0, 157.4, 144.4, 137.2, 135.1, 127.7, 119.9, 118.3, 42.7, 22.5

MS(ESI+):371.0872[M(free)+Na]$^+$, 387.0612[M(free)+K]$^+$

Production Example 25

N-[2-(4-{[2-(acetylamino)-1,3-thiazol-4-yl]methoxy}phenyl)ethyl]hydrazinecarboxamide trifluoroacetate Step 1

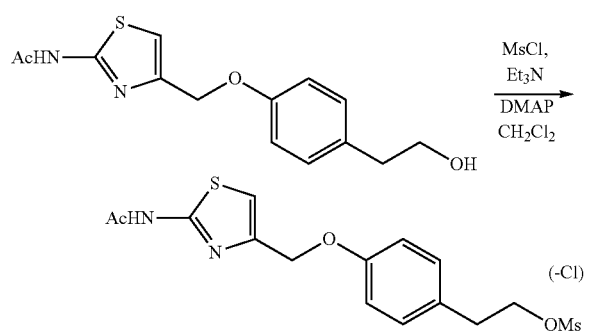

To a solution of N-(4-{[4-(2-hydroxyethyl)phenoxy]methyl}-1,3-thiazol-2-yl)acetamide (310.0 mg, 1.060 mmol) in anhydrous dichloromethane (8 ml) were added triethylamine (0.27 ml, 1.91 mmol) and 4-dimethylaminopyridine (13.0 mg, 0.106 mmol), and the mixture was cooled to 0° C. Methanesulfonyl chloride (0.12 ml, 1.60 mmol) was added dropwise at 0° C. The mixture was warmed to room temperature and stirred for 1 hr. Iced water (20 ml) was added to the reaction mixture and the mixture was stirred for 20 min, extracted 3 times with ethyl acetate. The combined organic layer was washed with 1M hydrochloric acid, saturated aqueous sodium hydrogen carbonate solution and saturated brine, dried over anhydrous magnesium sulfate and concentrated under reduced pressure to give 2-(4-{[2-(acetylamino)-1,3-thiazol-4-yl]methoxy}phenyl)ethyl methanesulfonate (410.8 mg, containing N-(4-{[4-(2-chloroethyl)phenoxy]methyl}-1,3-thiazol-2-yl)acetamide) as an orange solid.

Step 2

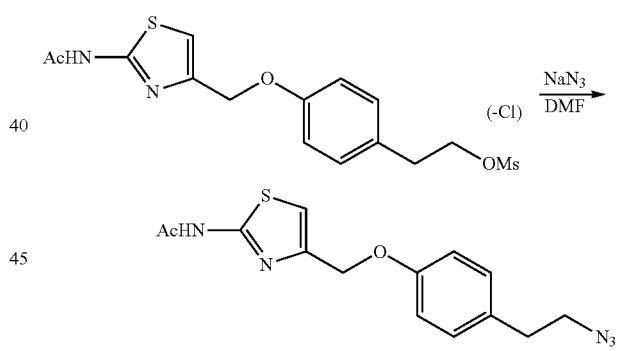

2-(4-{[2-(Acetylamino)-1,3-thiazol-4-yl]methoxy}phenyl)ethyl methanesulfonate (corresponding to 1.060 mmol) was azidated by a method similar to that of Production Example 20, step 2, to give N-(4-{[4-(2azidoethyl)phenoxy]methyl}-1,3-thiazol-2-yl)acetamide (240.7 mg, 0758 mmol, yield 71.5%) as a white solid.

Step 3

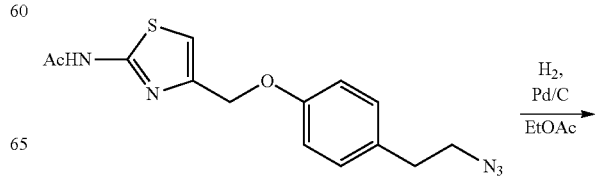

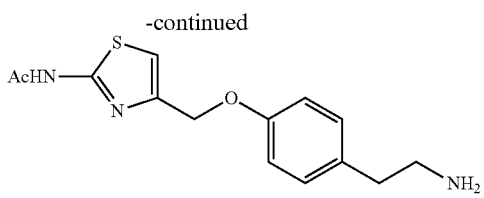

N-(4-{[4-(2-Azidoethyl)phenoxy]methyl}-1,3-thiazol-2-yl)acetamide (240.0 mg, 0.756 mmol) was hydrogenated by a method similar to that of Production Example 20, step 3, to give N-(4-{[4-(2-aminoethyl)phenoxy]methyl}-1,3-thiazol-2-yl)acetamide (217.6 mg, 0.747 mmol, yield 98.5%) as a white solid.

Step 4

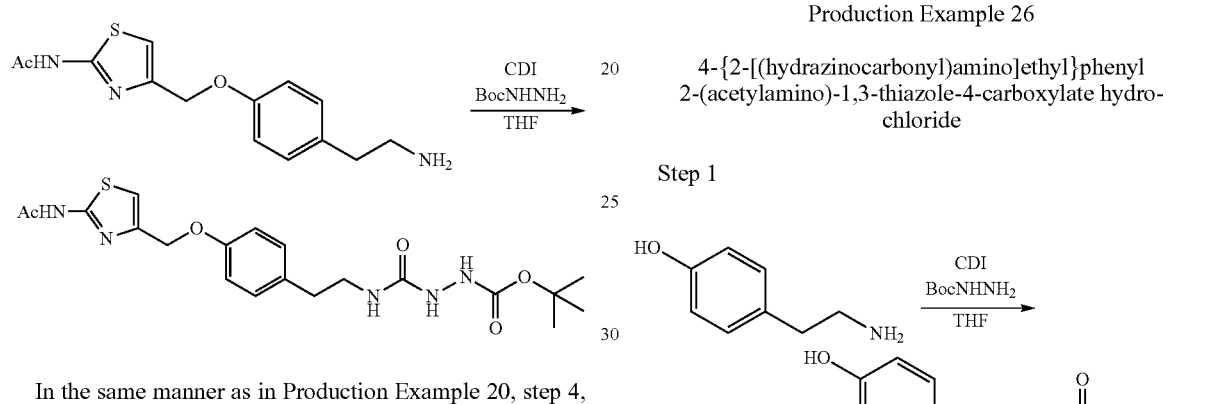

In the same manner as in Production Example 20, step 4, tert-butyl 2-{[2-(4-{[2-(acetylamino)-1,3-thiazol-4-yl]methoxy}phenyl)ethyl]carbamoyl}hydrazinecarboxylate (309.7 mg, 0.689 mmol, yield 97.9%) was obtained as a white solid from N-(4-{[4-(2-aminoethyl)phenoxy]methyl}-1,3-thiazol-2-yl)acetamide (205.0 mg, 0.704 mmol).

Step 5

To a solution of tert-butyl 2-{[2-(4-{[2-(acetylamino)-1,3-thiazol-4-yl]methoxy}phenyl)ethyl]carbamoyl}hydrazinecarboxylate (305.0 mg, 0.667 mmol) in anhydrous dichloromethane (20 ml) was added trifluoroacetic acid (2.48 ml, 33.4 mmol) at 0° C. The reaction mixture was stirred at room temperature for 2 hr, and concentrated under reduced pressure. Dichloromethane (20 ml) was added to the residue and the mixture was concentrated again under reduced pressure. This operation was repeated 3 times to remove trifluoroacetic acid azeotropically. Ethyl acetate (30 ml) was added to the residue and the mixture was stirred. The precipitate was collected by filtration, washed 5 times with ethyl acetate and 5 times with diethyl ether, and dried under reduced pressure to give the title compound (253.4 mg, 0.547 mmol, yield 81.9%) as a white solid.

melting point 195-197.5° C.

$^1$H-NMR (400 MHz, DMSO-d6): δ (ppm):12.14(1H, brs), 10.0-9.0(2H, br), 8.52(1H, brs), 7.16(1H, s), 7.03(1H, brs), 7.11(2H, d, J=8.6 Hz), 6.92(2H, d, J=8.6 Hz), 5.00(2H, s), 3.40-3.34(2H, m), 2.65(2H, t, J=7.3 Hz), 2.12(3H, s)

$^{13}$C-NMR (100 MHz, DMSO-d6): δ (ppm):168.6, 158.3, 157.5, 156.9, 146.7, 131.5, 129.8, 114.8, 111.4, 65.6, 41.3, 39.1, 34.8, 22.6 (peak of trifluoroacetic acid was weak in sensitivity and difficult to distinguish from the noise)

$^{19}$F-NMR (376 Hz, DMSO-d6): δ (ppm):−75.1

MS(ESI+):350.1262[M(free)+H]$^+$, 372.1085[M(free)+Na]$^+$

Production Example 26

4-{2-[(hydrazinocarbonyl)amino]ethyl}phenyl 2-(acetylamino)-1,3-thiazole-4-carboxylate hydrochloride Step 1

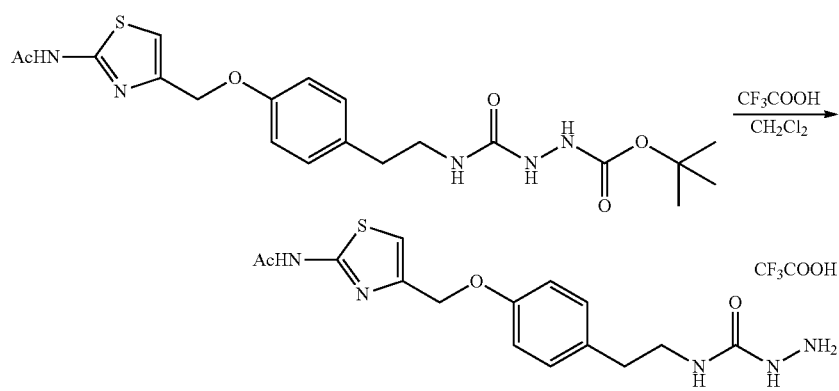

To a suspension of 1,1'-carbonyldiimidazole (1.621 g, 9.994 mmol) in anhydrous tetrahydrofuran (20 ml) was added tert-butyl carbazate (1.322 g, 10.00 mmol), and the mixture was stirred at room temperature for 1.5 hr. 4-(2-Aminoethyl)phenol (1.371 g, 9.991 mmol) was added and the mixture was stirred at room temperature for 6 hr. Water (40 ml) was added to the reaction mixture and the precipitate was collected by filtration, washed 3 times with water and twice with ethyl acetate, and dried under reduced pressure to give tert-butyl 2-{[2-(4-hydroxyphenyl)ethyl]carbamoyl}hydrazinecarboxylate (2.417 g, 8.184 mmol, yield 81.9%) as a white solid.

Step 2

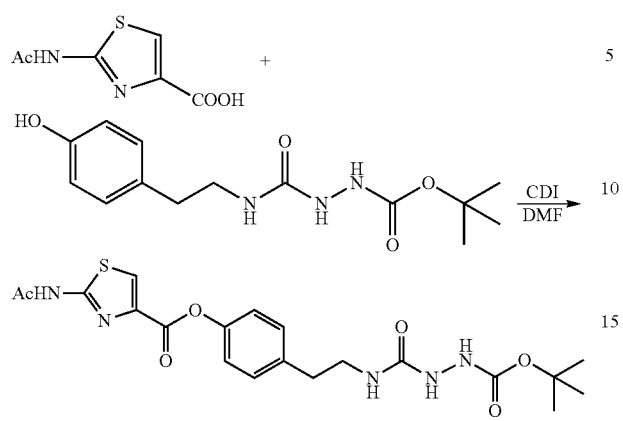

To a suspension of 2-(acetylamino)-1,3-thiazole-4-carboxylic acid (559.5 mg, 3.005 mmol) in anhydrous N,N-5 dimethylformamide (10 ml) was added 1,1'-carbonyldiimidazole (534.2 mg, 3.294 mmol), and the mixture was stirred at 50° C. for 2 hr. tert-Butyl 2-{[2-(4-hydroxyphenyl)ethyl]carbamoyl}hydrazinecarboxylate (591.6 mg, 2.003 mmol) was added, and the mixture was stirred at 50° C. for 24 hr and at room temperature for 17 hr. Water (50 ml) and ethyl acetate (50 ml) were added to the reaction mixture and the mixture was stirred, stood still and then partitioned. The aqueous layer was extracted with ethyl acetate. The combined organic layer was washed with 0.5M hydrochloric acid, saturated aqueous sodium hydrogen carbonate solution and saturated brine, dried over anhydrous magnesium sulfate, and concentrated under reduced pressure. Methanol (20 ml) and tert-butyl methyl ether (40 ml) were added to the residue and the precipitated solid was collected by filtration and dried under reduced pressure to give 4-[2-({[2-(tert-butoxycarbonyl)hydrazino]carbonyl}amino)ethyl]phenyl 2-(acetylamino)-1,3-thiazole-4-carboxylate (417.7 mg, 0.890 mmol, yield 44.5%) as a white solid.

Step 3

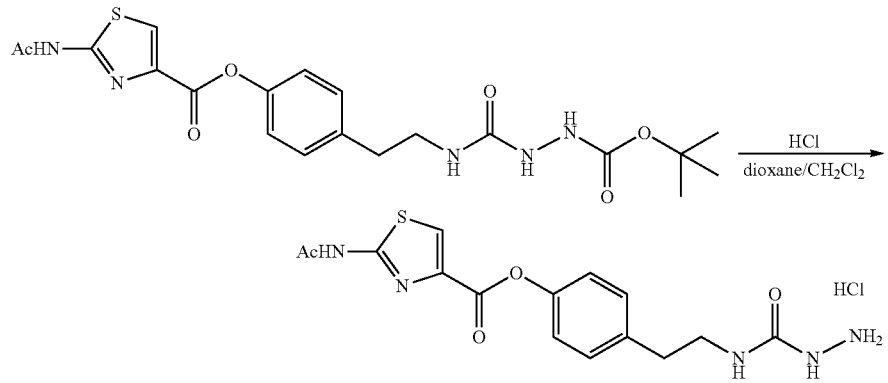

4-[2-({[2-(tert-Butoxycarbonyl)hydrazino]carbonyl}amino)ethyl]phenyl 2-(acetylamino)-1,3-thiazole-4-carboxylate (375.2 mg, 0.810 mmol) was deprotected by a method similar to that of Production Example 20, step 5, to give the title compound (300.8 mg, 0.752 mmol, yield 92.9%).

melting point 204-207° C.

$^1$H-NMR (400 MHz, DMSO-d6): δ (ppm):12.56(1H, brs), 9.87(3H, brs), 8.74(1H, brs), 8.28(1H, s), 7.30(2H, d, J=8.6 Hz), 7.17(2H, d, J=8.4 Hz), 7.07(1H, t, J=5.5 Hz), 3.35-3.30 (2H, m), 2.76(2H, t, J=7.1 Hz), 2.16(3H, s)

$^{13}$C-NMR (100 MHz, DMSO-d6): δ (ppm):169.1, 159.4, 158.2, 157.1, 148.6, 139.7, 136.9, 129.6, 124.4, 121.5, 40.8, 34.7, 22.3

MS(ESI+):386.0897[M(free)+Na]$^+$, 402.0639[M(free)+K]$^+$

Production Example 27

N-(3-{2-[2-(acetylamino)-1,3-thiazol-4-yl]ethyl}benzyl)hydrazinecarboxamide hydrochloride Step 1

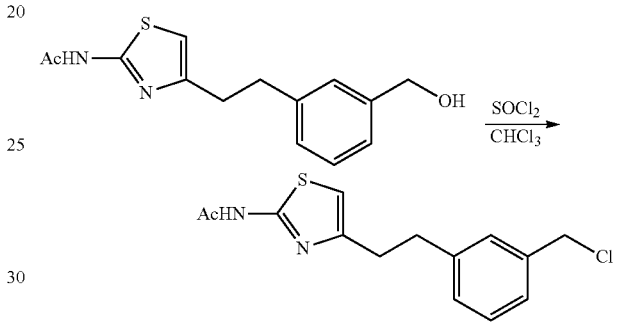

N-(4-{2-[3-(Hydroxymethyl)phenyl]ethyl}-1,3-thiazol-2-yl)acetamide (2.909 mmol) was chlorinated by a method similar to that of Production Example 20, step 1, to give N-(4-{2-[3-(chloromethyl)phenyl]ethyl}-1,3-thiazol-2-yl)acetamide (718.7 mg, 2.438 mmol, yield 83.8%) as a slightly yellow solid.

Step 2

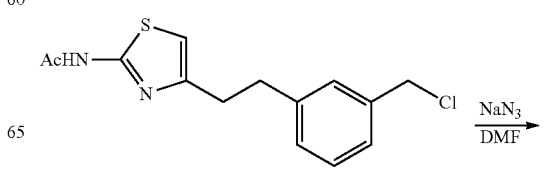

-continued

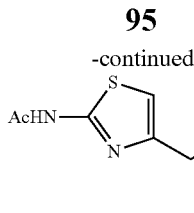

N-(4-{2-[3-(Chloromethyl)phenyl]ethyl}-1,3-thiazol-2-yl)acetamide (716.0 mg, 2.429 mmol) was azidated by a method similar to that of Production Example 20, step 2, to give N-(4-{2-[3-(azidomethyl)phenyl]ethyl}-1,3-thiazol-2-yl)acetamide (555.9 mg, 2.019 mmol, yield 83.1%) as a white solid.

Step 3

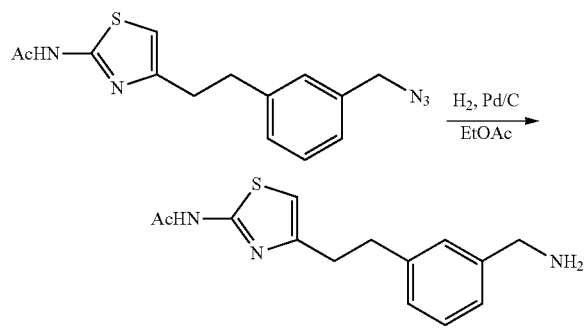

N-(4-{2-[3-(Azidomethyl)phenyl]ethyl}-1,3-thiazol-2-yl)acetamide (553.0 mg, 1.835 mmol) was hydrogenated by a method similar to that of Production Example 20, step 3, to give N-(4-{2-[3-(aminomethyl)phenyl]ethyl}-1,3-thiazol-2-yl)acetamide (467.5 mg, 1.698 mmol, yield 92.5%) as a white solid.

Step 4

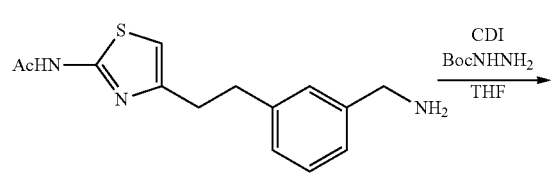

-continued

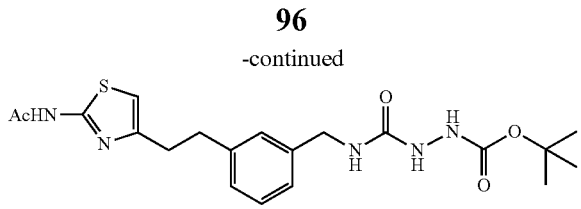

In a similar manner as in Production Example 20, step 4, tert-butyl 2-[(3-{2-[2-(acetylamino)-1,3-thiazol-4-yl]ethyl}benzyl)carbamoyl]hydrazinecarboxylate (483.2 mg, 1.115 mmol, yield 69.0%) was obtained as a white solid from N-(4-{2-[3-(aminomethyl)phenyl]ethyl}-1,3-thiazol-2-yl)acetamide (444.7 mg, 1.615 mmol).

Step 5

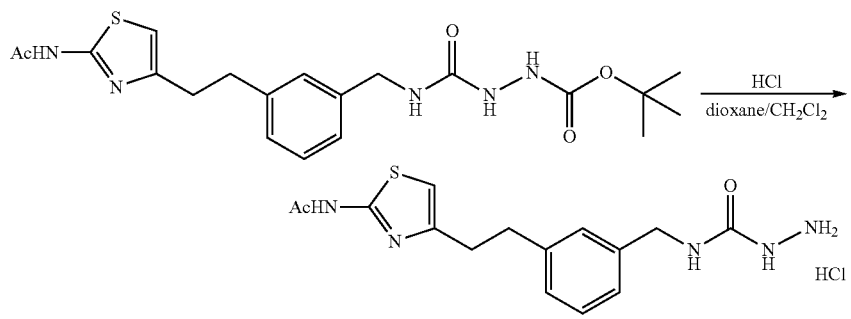

tert-Butyl 2-[(3-{2-[2-(acetylamino)-1,3-thiazol-4-yl]ethyl}benzyl)carbamoyl]hydrazinecarboxylate (412.6 mg, 0.952 mmol) was deprotected by a method similar to that of Production Example 20, step 5, to give the title compound (341.0 mg, 0.922 mmol, yield 96.8%) as a white solid.

melting point 123-127° C.

$^1$H-NMR (400 MHz, DMSO-d6): δ (ppm): 12.08(1H, brs), 9.96(3H, brs), 8.93(1H, brs), 7.56(1H, brt, J=5.8 Hz), 7.21 (1H, t, J=7.6 Hz), 7.14(1H, s), 7.09-7.05(2H, m), 6.75(1H, s), 4.24(2H, d, J=5.8 Hz), 2.91-2.83(4H, m), 2.11(3H, s)

$^{13}$C-NMR (100 MHz, DMSO-d6): δ (ppm): 168.4, 157.7, 157.5, 150.3, 141.6, 139.7, 128.4, 127.2, 126.9, 124.9, 107.6, 43.0, 34.8, 32.9, 22.6

MS(ESI+):334.1328[M(free)+H]$^+$, 356.1147[M(free)+Na]$^+$

Production Example 28

N-[2-(3-{2-[2-(acetylamino)-1,3-thiazol-4-yl]ethyl}phenyl)ethyl]hydrazinecarboxamide hydrochloride Step 1

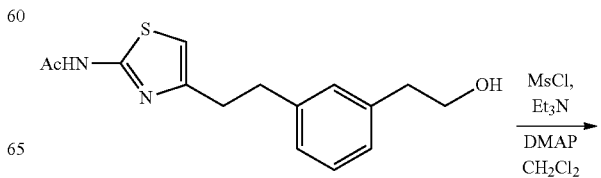

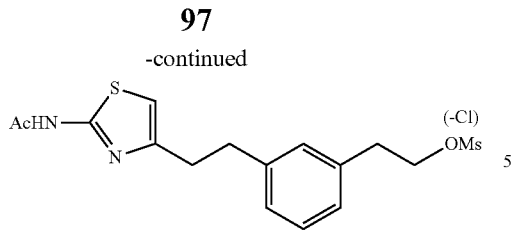

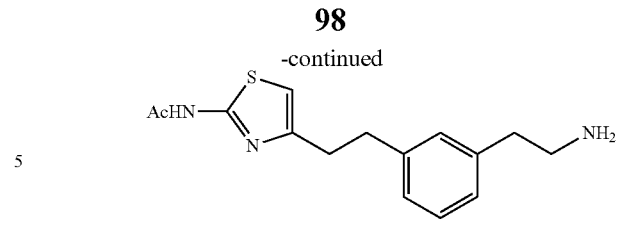

N-(4-{2-[3-(2-Hydroxyethyl)phenyl]ethyl}-1,3-thiazol-2-yl)acetamide (360.0 mg, 1.240 mmol) was mesylated by a method similar to that of Production Example 25, step 1, to give 2-(3-{2-[2-(acetylamino)-1,3-thiazol-4-yl]ethyl}phenyl)ethyl methanesulfonate (454.9 mg, containing N-(4-{2-[3-(2-chloroethyl)phenyl]ethyl}-1,3-thiazol-2-yl)acetamide) as a yellow solid.

Step 2

N-(4-{2-[3-(2-Azidoethyl)phenyl]ethyl}-1,3-thiazol-2-yl)acetamide (300.0 mg, 0.951 mmol) was hydrogenated by a method similar to that of Production Example 20, step 3, to give N-(4-{2-[3-(2-aminoethyl)phenyl]ethyl}-1,3-thiazol-2-yl)acetamide (329.8 mg) as a white solid.

Step 4

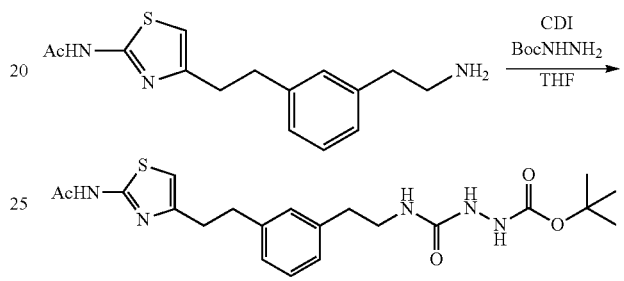

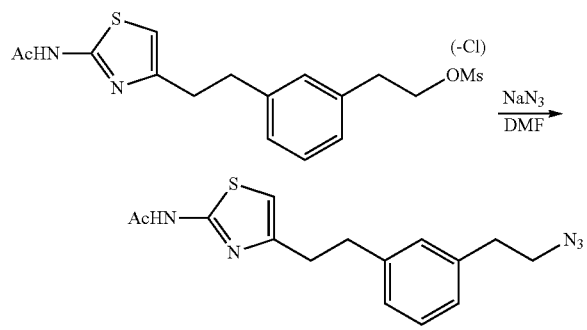

2-(3-{2-[2-(Acetylamino)-1,3-thiazol-4-yl]ethyl}phenyl)ethyl methanesulfonate (corresponding to 1.240 mmol) was azidated by a method similar to that of Production Example 20, step 2, to give N-(4-{2-[3-(2-azidoethyl)phenyl]ethyl}-1,3-thiazol-2-yl)acetamide (304.7 mg, 0.966 mmol, total yield from step 1 77.9%) as a white solid.

Step 3

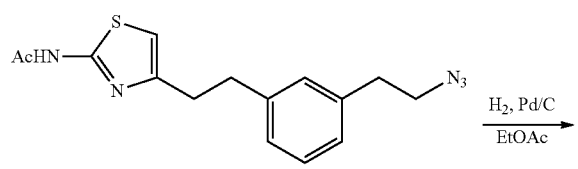

In a similar manner as in Production Example 20, step 4, tert-butyl 2-{[2-(3-{2-[2-(acetylamino)-1,3-thiazol-4-yl]ethyl}phenyl)ethyl]carbamoyl}hydrazinecarboxylate (238.2 mg, 0.532 mmol, total yield from step 3 55.9%) was obtained as a white solid from N-(4-{2-[3-(2-aminoethyl)phenyl]ethyl}-1,3-thiazol-2-yl)acetamide (corresponding to 0.951 mmol).

Step 5

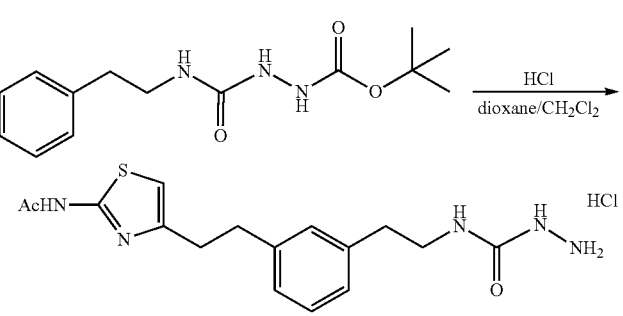

tert-Butyl 2-{[2-(3-{2-[2-(acetylamino)-1,3-thiazol-4-yl]ethyl}phenyl)ethyl]carbamoyl}hydrazinecarboxylate (225.0 mg, 0.503 mmol) was deprotected by a method similar to that of Production Example 20, step 5, to give the title compound (191.6 mg, 0.499 mmol, yield 99.2%) as a white solid.

melting point 176-179° C.

$^1$H-NMR (400 MHz, DMSO-d6): δ (ppm):12.09(1H, brs), 9.95(3H, brs), 8.79(1H, brs), 7.18(1H, t, J=7.6 Hz), 7.06-7.01 (4H, m), 6.73(1H, s), 3.40-3.20(2H, m), 2.91-2.84(4H, m), 2.68(2H, t, J=7.3 Hz), 2.11(3H, s)

$^{13}$C-NMR (100 MHz, DMSO-d6): δ (ppm):168.4, 157.6, 157.3, 150.4, 141.6, 139.2, 128.8, 128.5, 126.4, 126.3, 107.5, 41.1, 35.7, 34.8, 33.0, 22.6

MS(ESI+):348.1429[M(free)+H]$^+$, 370.1252[M(free)+Na]$^+$

Production Example 29

N-[2-(5-{2-[2-(acetylamino)-1,3-thiazol-4-yl]ethyl}thiophen-2-yl)methyl]hydrazinecarboxamide hydrochloride Step 1

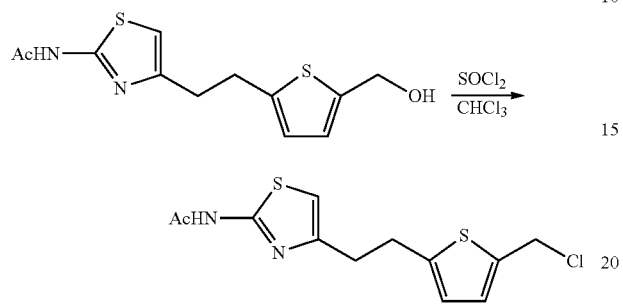

In a water bath at about 20° C., to a suspension of N-(4-{2-[5-(hydroxymethyl)thiophen-2-yl]ethyl}-1,3-thiazol-2-yl)acetamide (500.0 mg, 1.771 mmol) in anhydrous chloroform (2.5 ml) was added dropwise thionyl chloride (0.77 ml, 10.6 mmol). After stirring at room temperature for 1 hr, the reaction mixture was concentrated under reduced pressure. Anhydrous chloroform (5 ml) was added to the residue and the mixture was concentrated again under reduced pressure. This operation was repeated 3 times to remove thionyl chloride azeotropically. The residue was dried under reduced pressure to give N-(4-{2-[5-(chloromethyl)thiophen-2-yl]ethyl}-1,3-thiazol-2-yl)acetamide (633.2 mg) as a pale-brown solid.

Step 2

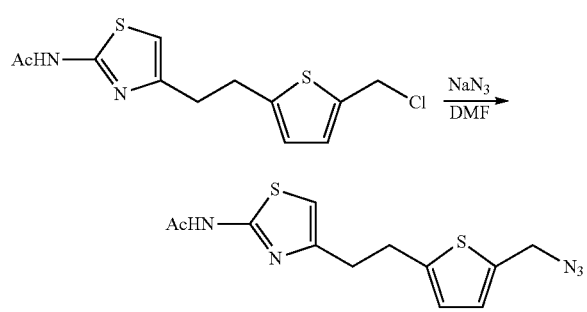

N-(4-{2-[5-(Chloromethyl)thiophen-2-yl]ethyl}-1,3-thiazol-2-yl)acetamide (corresponding to 1.771 mmol) was azidated by a method similar to that of Production Example 20, step 2, to give N-(4-{2-[5-(azidomethyl)thiophen-2-yl]ethyl}-1,3-thiazol-2-yl)acetamide (489.8 mg, 1.593 mmol, yield 90.0%) as a slightly yellow solid.

Step 3

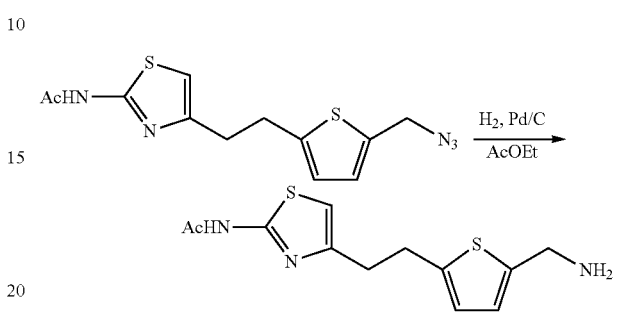

N-(4-{2-[5-(Azidomethyl)thiophen-2-yl]ethyl}-1,3-thiazol-2-yl)acetamide (480.0 mg, 1.562 mmol) was hydrogenated by a method similar to that of Production Example 20, step 3, to give N-(4-{2-[5-(aminomethyl)thiophen-2-yl]ethyl}-1,3-thiazol-2-yl)acetamide (376.1 mg, 1.337 mmol, yield 85.6%) as a white solid.

Step 4

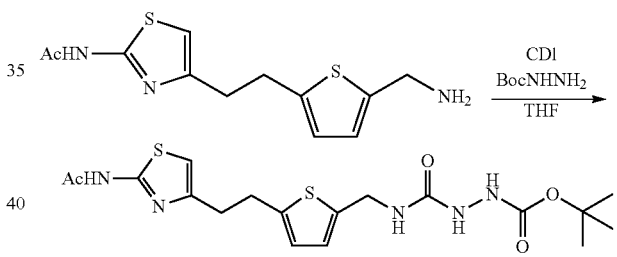

In a similar manner as in Production Example 20, step 4, tert-butyl 2-{[2-(5-{2-[2-(acetylamino)-1,3-thiazol-4-yl]ethyl}thiophen-2-yl)methyl]carbamoyl}hydrazinecarboxylate (307.9 mg, 0.700 mmol, yield 56.3%) was obtained as a white solid from N-(4-{2-[5-(aminomethyl)thiophen-2-yl]ethyl}-1,3-thiazol-2-yl)acetamide (350.0 mg, 1.244 mmol).

Step 5

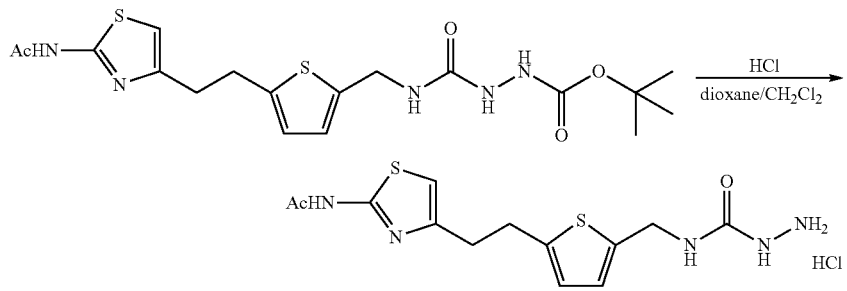

tert-Butyl 2-{[2-(5-{2-[2-(acetylamino)-1,3-thiazol-4-yl]ethyl}thiophen-2-yl)methyl]carbamoyl}hydrazinecarboxylate (250.0 mg, 0.569 mmol) was deprotected by a method similar to that of Production Example 20, step 5, to give the title compound (208.7 mg, 0.555 mmol, yield 97.6%) as a white solid.

melting point 158-161° C.

¹H-NMR (400 MHz, DMSO-d6): δ(ppm):12.08(1H, brs), 9.98(3H, brs), 8.93(1H, brs), 7.54(1H, brt, J=5.6 Hz), 6.77 (1H, s), 6.74(2H, d, J=3.2 Hz), 6.64(2H, d, J=3.2 Hz), 4.32 (2H, d, J=5.6 Hz), 3.08(2H, d, J=7.5 Hz), 2.87(2H, d, J=7.5 Hz), 2.10(3H, s)

¹³C-NMR (100 MHz, DMSO-d6): δ(ppm):168.5, 157.7, 157.1, 149.8, 143.3, 140.2, 125.3, 124.2, 108.0, 38.4, 33.1, 29.0, 22.7

MS(ESI+):340.0855[M(free)+H]⁺, 362.0670[M(free)+Na]⁺

Production Example 30

N-[2-(5-{2-[2-(acetylamino)-1,3-thiazol-4-yl]ethyl}thiophen-2-yl)ethyl]hydrazinecarboxamide hydrochloride Step 1

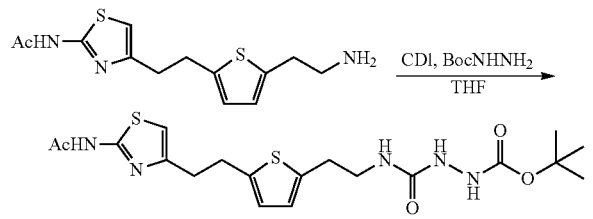

In a similar manner as in Production Example 20, step 4, tert-butyl 2-{[2-(5-{2-[2-(acetylamino)-1,3-thiazol-4-yl]ethyl}thiophen-2-yl)ethyl]carbamoyl}hydrazinecarboxylate (658.6 mg, 1.452 mmol, yield 90.3%) was obtained as a white solid from N-(4-{2-[5-(2-aminoethyl)thiophen-2-yl]ethyl}-1,3-thiazol-2-yl)acetamide (475.0 mg, 1.608 mmol).

Step 2

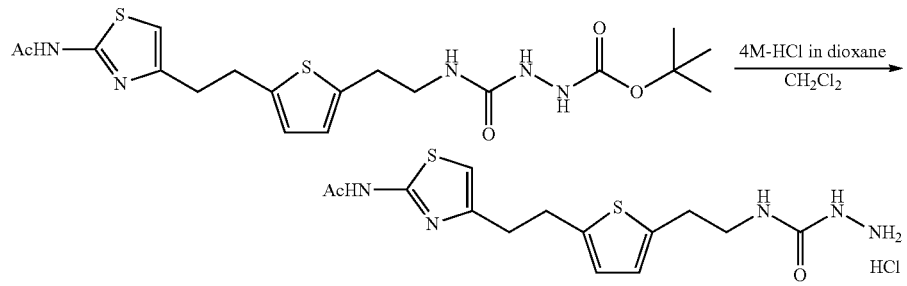

tert-Butyl 2-{[2-(5-{2-[2-(acetylamino)-1,3-thiazol-4-yl]ethyl}thiophen-2-yl)ethyl]carbamoyl}hydrazinecarboxylate (650.0 mg, 1.433 mmol) was deprotected by a method similar to that of Production Example 20, step 5. The crude product was dissolved in water, and recrystallized by addition of acetonitrile. The precipitate was collected by filtration, washed 3 times with acetonitrile and dried under reduced pressure to give the title compound (485.1 mg, 1.244 mmol, yield 86.8%) as a white solid.

melting point 178-181° C.

¹H-NMR (200 MHz, DMSO-d6): δ(ppm):12.09(1H, brs), 9.97(3H, brs), 8.85(1H, brs), 7.11(1H, brt, J=5.0 Hz), 6.78 (1H, s), 6.70-6.60(2H, m), 3.35-5.15(2H, m), 3.15-3.00(2H, m), 2.95-2.80(4H, m), 2.11(3H, s)

¹³C-NMR (50 MHz, DMSO-d6): δ(ppm):168.7, 158.0, 157.6, 150.8, 142.4, 139.4, 125.3, 124.8, 108.3, 41.5, 38.7, 30.4, 29.3, 22.9

MS(ESI+):354.1049[M(free)+H]⁺, 370.1252[M(free)+Na]⁺

Production Example 31

N-[3-(4-{2-[2-(acetylamino)-1,3-thiazol-4-yl]ethyl}thiophen-2-yl)propyl]hydrazinecarboxamide hydrochloride Step 1

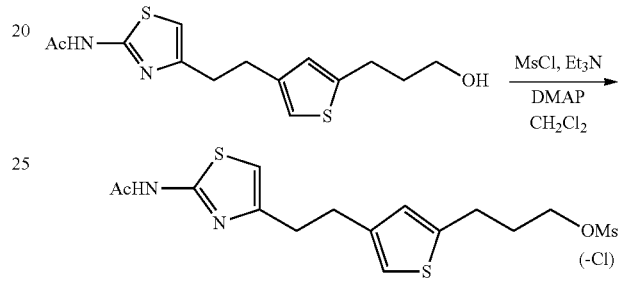

N-(4-{2-[5-(3-Hydroxypropyl)thiophen-3-yl]ethyl}-1,3-thiazol-2-yl)acetamide (290.0 mg, 0.934 mmol) was mesylated by a method similar to that of Production Example 25, step 1, to give 3-(4-{2-[2-(acetylamino)-1,3-thiazol-4-yl]ethyl}thiophen-3-yl)propyl methanesulfonate (362.4 mg, containing a small amount of N-(4-{2-[5-(3-chloropropyl)thiophen-3-yl]ethyl}-1,3-thiazol-2-yl)acetamide, 0.933 mmol as sulfonate, yield 99.8%) as a pale-orange solid.

Step 2

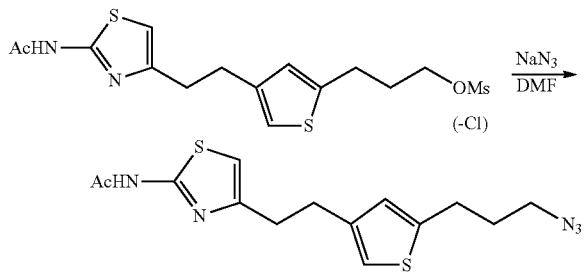

3-(4-{2-[2-(Acetylamino)-1,3-thiazol-4-yl]ethyl}thiophen-3-yl)propyl methanesulfonate (360.0 mg, 0.927 mmol) was azidated by a method similar to that of Production Example 20, step 2, to give N-(4-{2-[5-(3-azidopropyl)thiophen-3-yl]ethyl}-1,3-thiazol-2-yl)acetamide (286.4 mg, 0.854 mmol, yield 92.1%) as a white solid.

Step 3

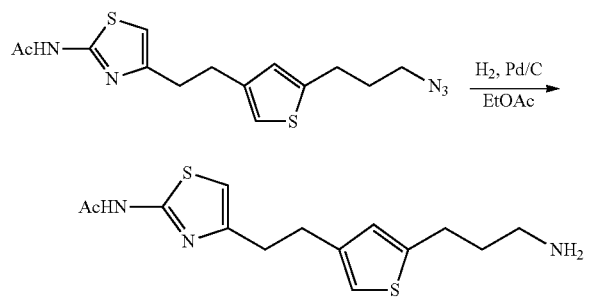

N-(4-{2-[5-(3-Azidopropyl)thiophen-3-yl]ethyl}-1,3-thiazol-2-yl)acetamide (280.0 mg, 0.843 mmol) was hydrogenated by a method similar to that of Production Example 20, step 3, to give N-(4-{2-[5-(3-aminopropyl)thiophen-3-yl]ethyl}-1,3-thiazol-2-yl)acetamide (247.1 mg, 0.799 mmol, yield 94.7%) as a white solid.

Step 4

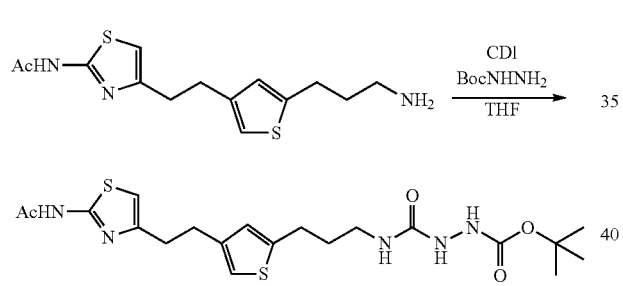

In a similar manner as in Production Example 20, step 4, tert-butyl 2-{[3-(4-{2-[2-(acetylamino)-1,3-thiazol-4-yl]ethyl}thiophen-2-yl)propyl]carbamoyl}hydrazinecarboxylate (180.3 mg, 0.386 mmol, yield 70.2%) was obtained as a white solid from N-(4-{2-[5-(3-aminopropyl)thiophen-3-yl]ethyl}-1,3-thiazol-2-yl)acetamide (170.0 mg, 0.549 mmol).

Step 5

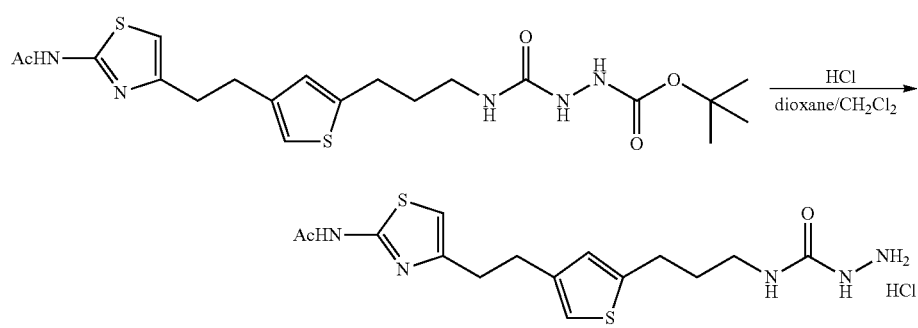

tert-Butyl 2-{[3-(4-{2-[2-(acetylamino)-1,3-thiazol-4-yl]ethyl}thiophen-2-yl)propyl]carbamoyl}hydrazinecarboxylate (180.0 mg, 0.385 mmol) was deprotected by a method similar to that of Production Example 20, step 5, to give the title compound (102.7 mg, 0.254 mmol, yield 66.0%) as a white solid.

melting point 153-156° C.

$^1$H-NMR (400 MHz, DMSO-d6): δ (ppm):12.04(1H, brs), 9.72(3H, brs), 8.61(1H, brs), 7.10(1H, brt), 6.91(1H, s), 6.73 (1H, s), 6.71(1H, s), 3.12-3.06(2H, m), 2.90-2.80(4H, m), 2.73(2H, t, J=7.6 Hz), 2.10(3H, s), 1.72(2H, tt, J=7.6, 6.4 Hz)

$^{13}$C-NMR (100 MHz, DMSO-d6): δ (ppm):168.4, 157.6, 150.6, 144.1, 141.6, 126.0, 118.4, 107.4, 32.0, 31.7, 29.5, 26.9, 22.6

MS(ESI+):368.1182[M(free)+H]$^+$, 390.0097[M(free)+Na]$^+$

Production Example 32

N-[3-(5-{2-[2-(acetylamino)-1,3-thiazol-4-yl]ethyl}thiophen-3-yl)propyl]hydrazinecarboxamide hydrochloride Step 1

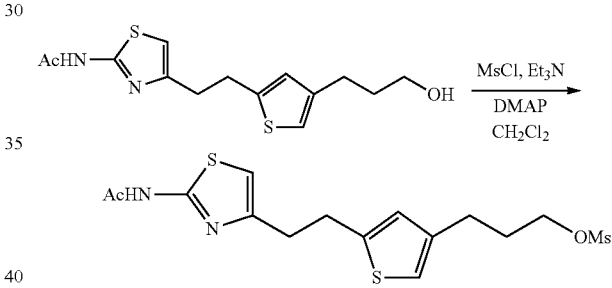

N-(4-{2-[5-(3-Hydroxypropyl)thiophen-3-yl]ethyl}-1,3-thiazol-2-yl)acetamide (380.0 mg, 1.224 mmol) was mesylated by a method similar to that of Production Example 25, step 1. The crude product was purified by silica gel column chromatography (FUJI SILYSIA CHEMICAL LTD. BW-300SP 70 g, dichloromethane:methanol=40:1) to give 3-(5-{2-[2-(acetylamino)-1,3-thiazol-4-yl]ethyl}thiophen-3-yl)propyl methanesulfonate (461.3 mg, 1.187 mmol, yield 97.0%) as an off-white solid.

Step 2

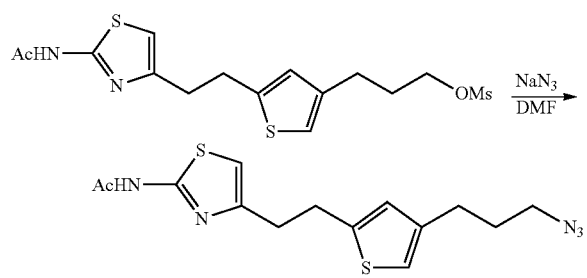

3-(5-{2-[2-(Acetylamino)-1,3-thiazol-4-yl]ethyl}thiophen-3-yl)propyl methanesulfonate (460.0 mg, 1.184 mmol) was azidated by a method similar to that of Production Example 20, step 2, to give N-(4-{2-[4-(3-azidopropyl)thiophen-2-yl]ethyl}-1,3-thiazol-2-yl)acetamide (322.8 mg, 0.962 mmol, yield 81.3%) as a white solid.

Step 3

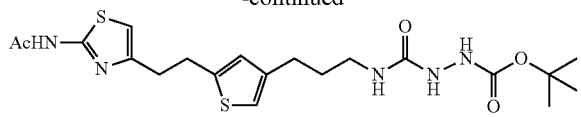

N-(4-{2-[4-(3-Azidopropyl)thiophen-2-yl]ethyl}-1,3-thiazol-2-yl)acetamide (310.4 mg, 0.925 mmol) was hydrogenated by a method similar to that of Production Example 20, step 3, to give N-(4-{2-[4-(3-aminopropyl)thiophen-2-yl]ethyl}-1,3-thiazol-2-yl)acetamide (284.5 mg, 0.919 mmol, yield 99.4%) as a white solid.

Step 4

In the same manner as in Production Example 20, step 4, tert-butyl 2-{[3-(5-{2-[2-(acetylamino)-1,3-thiazol-4-yl]ethyl}thiophen-3-yl)propyl]carbamoyl}hydrazinecarboxylate (423.0 mg, 0.905 mmol, yield 100%) was obtained as an off-white solid from N-(4-{2-[4-(3-aminopropyl)thiophen-2-yl]ethyl}-1,3-thiazol-2-yl)acetamide (280.1 mg, 0.905 mmol).

Step 5

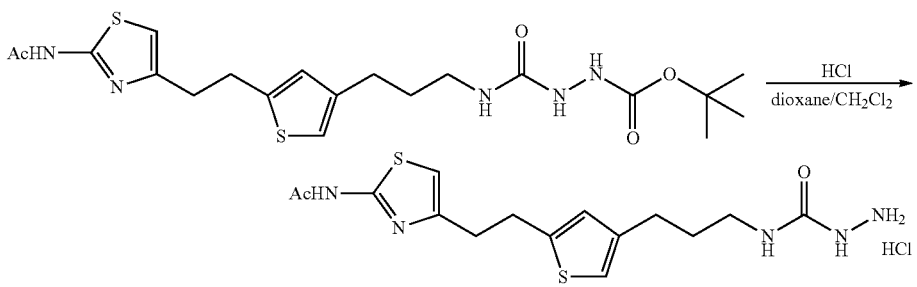

tert-Butyl 2-{[3-(5-{2-[2-(acetylamino)-1,3-thiazol-4-yl]ethyl}thiophen-3-yl)propyl]carbamoyl}hydrazinecarboxylate (420.1 mg, 0.898 mmol) was deprotected by a method similar to that of Production Example 20, step 5, to give the title compound (333.5 mg, 0.831 mmol, yield 92.5%) as a white solid.

melting point 111-115° C.

$^1$H-NMR (200 MHz, DMSO-d6): δ (ppm): 12.08(1H, brs), 9.96(3H, brs), 8.80(1H, brs), 7.15(1H, brs), 6.89(1H, s), 6.77(1H, s), 6.70(1H, s), 3.30-2.95(6H, m), 2.95-2.80(2H, m), 2.11(3H, s), 1.98-1.64(2H, m)

$^{13}$C-NMR (50 MHz, DMSO-d6): δ (ppm):168.4, 157.7, 157.4, 149.8, 143.9, 141.5, 126.1, 118.4, 108.0, 33.2, 30.3, 29.1, 27.2, 22.7

MS(ESI+):368.1194[M(free)+H]$^+$, 390.1015[M(free)+Na]$^+$

Production Example 33

N-[3-(5-{2-[2-(acetylamino)-1,3-thiazol-4-yl]ethyl}-3-methylthiophen-2-yl)propyl]hydrazinecarboxamide hydrochloride Step 1

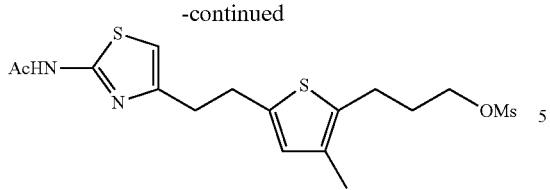

N-(4-{2-[5-(3-Hydroxypropyl)-4-methylthiophen-2-yl]ethyl}-1,3-thiazol-2-yl)acetamide (102.1 mg, 0.315 mmol) was mesylated by a method similar to that of Production Example 25, step 1. The crude product was purified by silica gel column chromatography (FUJI SILYSIA CHEMICAL LTD. BW-300SP 15 g, dichloromethane:methanol=30:1) to give 3-(5-{2-[2-(acetylamino)-1,3-thiazol-4-yl]ethyl}-3-methylthiophen-2-yl)propyl methanesulfonate (93.0 mg, 0.231 mmol, yield 73.3%) as a pale-yellow solid.

Step 2

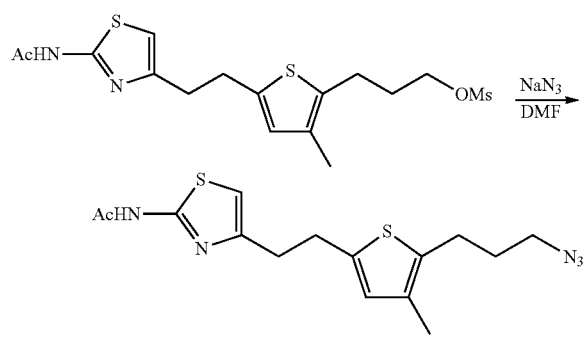

3-(5-{2-[2-(Acetylamino)-1,3-thiazol-4-yl]ethyl}-3-methylthiophen-2-yl)propyl methanesulfonate (88.0 mg, 0.219 mmol) was azidated by a method similar to that of Production Example 20, step 2, to give N-(4-{2-[5-(3-azidopropyl)-4-methylthiophen-2-yl]ethyl}-1,3-thiazol-2-yl)acetamide (52.0 mg, 0.149 mmol, yield 68.0%) as a pale-yellow solid.

Step 3

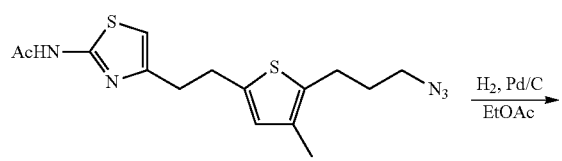

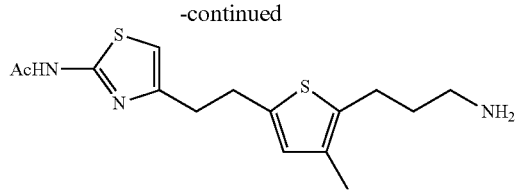

N-(4-{2-[5-(3-Azidopropyl)-4-methylthiophen-2-yl]ethyl}-1,3-thiazol-2-yl)acetamide (47.2 mg, 0.135 mmol) was hydrogenated by a method similar to that of Production Example 20, step 3, to give N-(4-{2-[5-(3-aminopropyl)-4-methylthiophen-2-yl]ethyl}-1,3-thiazol-2-yl)acetamide (42.7 mg, 0.132 mmol, yield 97.8%) as a pale-yellow solid.

Step 4

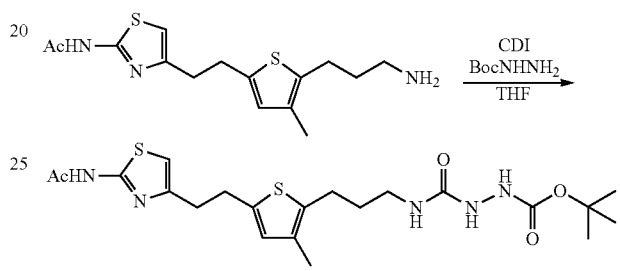

In a similar manner as in Production Example 20, step 4, tert-butyl 2-{[3-(5-{2-[2-(acetylamino)-1,3-thiazol-4-yl]ethyl}-3-methylthiophen-2-yl)propyl]carbamoyl}hydrazinecarboxylate (60.9 mg, 0.126 mmol, yield 96.2%) was obtained as a pale-yellow solid from N-(4-{2-[5-(3-aminopropyl)-4-methylthiophen-2-yl]ethyl}-1,3-thiazol-2-yl)acetamide (42.5 mg, 0.131 mmol).

Step 5

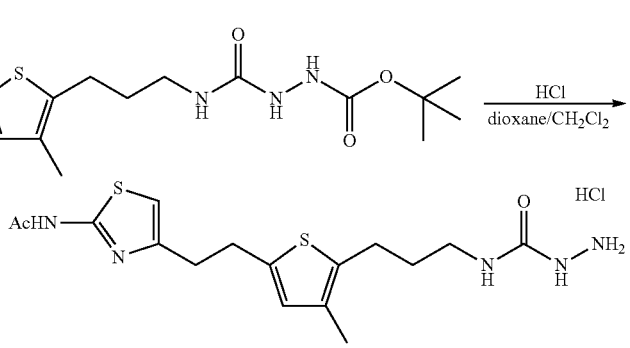

tert-Butyl 2-{[3-(5-{2-[2-(acetylamino)-1,3-thiazol-4-yl]ethyl}-3-methylthiophen-2-yl)propyl]carbamoyl}hydrazinecarboxylate (48.4 mg, 0.101 mmol) was deprotected by a method similar to that of Production Example 20, step 5, to give the title compound (41.9 mg, 0.100 mmol, yield 99.0%) as a white solid.

melting point 152-157° C.

$^1$H-NMR (400 MHz, DMSO-d6): δ(ppm):12.06(1H, brs), 9.87(3H, brs), 8.72(1H, brs), 7.13(1H, brt), 6.76(1H, s), 6.51(1H, s), 3.11-3.05(2H, m), 3.01(2H, t, J=7.4 Hz), 2.85(2H, t, J=7.4 Hz), 2.60(2H, t, J=7.6 Hz), 2.10(3H, s), 2.01(3H, s), 1.63(2H, quint, J=7.6 Hz)

$^{13}$C-NMR (100 MHz, DMSO-d6): δ(ppm):168.3, 157.5, 157.3, 149.8, 139.3, 134.8, 131.9, 127.5, 107.8, 33.0, 31.5, 28.9, 24.6, 22.5, 13.4

MS(ESI+):382.1351[M(free)+H]$^+$, 405.1098[M(free)+Na]$^+$

Production Example 34

S-(4-{2-[2-(acetylamino)-1,3-thiazol-4-yl]ethyl}benzyl) hydrazinecarbothioate hydrochloride Step 1

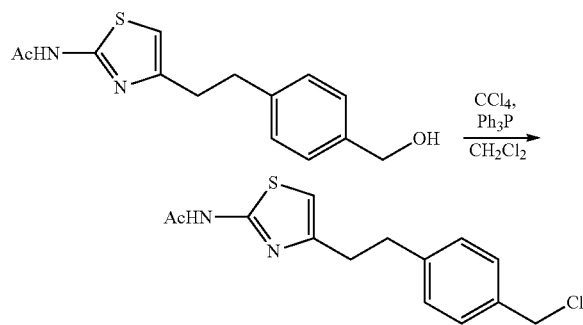

To a suspension of N-(4-{2-[4-(hydroxymethyl)phenyl]ethyl}-1,3-thiazol-2-yl)acetamide (1.383 g, 5.005 mmol) in anhydrous dichloromethane (60 ml) were added carbon tetrachloride (5.8 ml, 60 mmol) and triphenylphosphine (1.574 g, 6.000 mmol), and the mixture was stirred at room temperature for 22.5 hr. Triphenylphosphine (786.0 mg, 2.997 mmol) was added, and the mixture was stirred at room temperature for 1.5 hr. The reaction mixture was concentrated under reduced pressure. The residue was purified by silica gel column chromatography (FUJI SILYSIA CHEMICAL LTD. BW-300SP 100 g, ethyl acetate:hexane=2:3) to give N-(4-{2-[4-(chloromethyl)phenyl]ethyl}-1,3-thiazol-2-yl)acetamide (1.224 g, 4.153 mmol, yield 83.0%) as a white solid.

Step 2

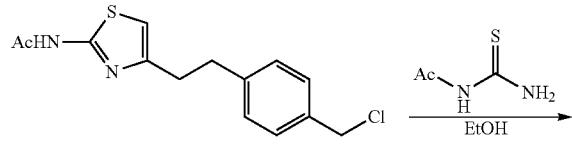

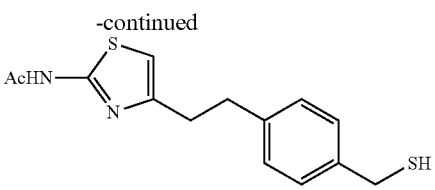

To a suspension of N-(4-{2-[4-(chloromethyl)phenyl]ethyl}-1,3-thiazol-2-yl)acetamide (589.7 mg, 2.000 mmol) in ethanol (10 ml) was added 1-acetyl-2-thiourea (472.6 mg, 4.000 mmol), and the mixture was heated under reflux for 19 hr. After cooling to room temperature, the mixture was concentrated under reduced pressure. The residue was purified by silica gel column chromatography (FUJI SILYSIA CHEMICAL LTD. BW-300SP 30 g, ethyl acetate:hexane=2:3) to give N-(4-{2-[4-(sulfanylmethyl)phenyl]ethyl}-1,3-thiazol-2-yl)acetamide (507.7 mg, 1.736 mmol, yield 86.8%) as a white solid.

Step 3

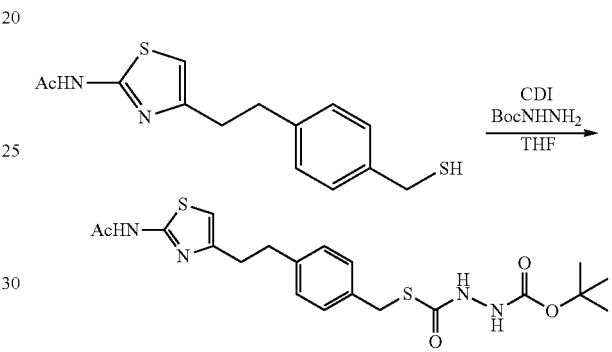

To a solution of N-(4-{2-[4-(sulfanylmethyl)phenyl]ethyl}-1,3-thiazol-2-yl)acetamide (468.9 mg, 1.604 mmol) in anhydrous tetrahydrofuran (5 ml) was added 1,1'-carbonyldiimidazole (390.6 mg, 2.409 mmol), and the mixture was stirred at room temperature for 3 hr. tert-Butyl carbazate (422.4 mg, 3.196 mmol) was added, and the mixture was stirred at room temperature for 21 hr. Water (15 ml), 1M hydrochloric acid (15 ml) and ethyl acetate (30 ml) were added, and the mixture was stirred, stood still and then partitioned. The organic layer was washed with water, dried over anhydrous magnesium sulfate, and concentrated under reduced pressure. The residue was suspended in dichloromethane (15 ml), and the suspension was filtered, washed with dichloromethane, and dried under reduced pressure to give tert-butyl 2-({[2-(4-{2-[(acetylamino)-1,3-thiazol-4-yl]ethyl}phenyl)methyl]sulfanyl}carbonyl)hydrazinecarboxylate (602.2 mg, 1.337 mmol, yield 83.3%) as a white solid.

Step 4

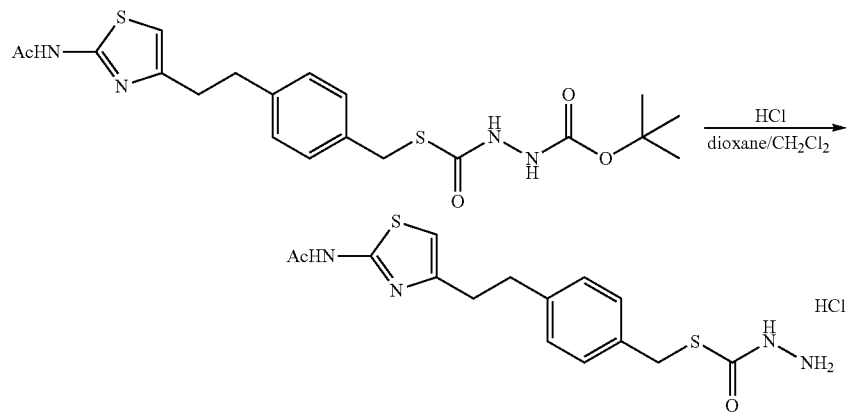

To a suspension of tert-butyl 2-({[2-(4-{2-[2-(acetylamino)-1,3-thiazol-4-yl]ethyl}phenyl)methyl]sulfanyl}carbonyl)hydrazinecarboxylate (450.4 mg, 1.000 mmol) in anhydrous dichloromethane (5 ml) was added 4M hydrogen chloride dioxane solution (5 ml) and the mixture was stirred at room temperature for 2 hr. The reaction mixture was concentrated under reduced pressure. Ethyl acetate (20 ml) was added to the residue and the mixture was concentrated again under reduced pressure. This operation was repeated 3 times to remove hydrogen chloride azeotropically. The residue was suspended in a mixture of ethanol (5 ml) and ethyl acetate (15 ml), and the suspension was filtered, washed twice with ethyl acetate, and dried under reduced pressure to give the title compound (375.6 mg, 0.971 mmol, yield 97.1%) as a white solid.

melting point 149-158° C.

$^1$H-NMR (400 MHz, DMSO-d6): δ (ppm):12.03(1H, brs), 10.99(1H, brs), 10.8-9.6(3H, br), 7.22(2H, d, J=8.2 Hz), 7.13 (2H, d, J=8.1 Hz), 6.72(1H, s), 4.11(2H, s), 2.92-2.81(4H, m), 2.10(3H, s)

$^{13}$C-NMR (100 MHz, DMSO-d6): δ (ppm):168.1, 167.2, 157.4, 150.0, 140.3, 135.3, 128.6, 128.3, 107.3, 34.0, 32.5, 32.4, 22.4

MS(ESI+):351.0931[M(free)+H]$^+$, 373.0757[M(free)+Na]$^+$

Production Example 35

S-[2-(4-{2-[2-(acetylamino)-1,3-thiazol-4-yl]ethyl}phenyl)ethyl]hydrazinecarbothioate hydrochloride Step 1

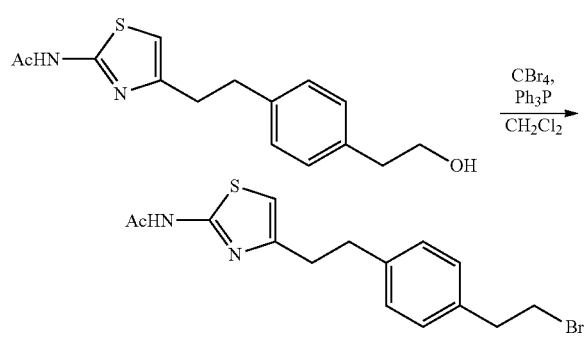

To a suspension of N-(4-{2-[4-(2-hydroxyethyl)phenyl]ethyl}-1,3-thiazol-2-yl)acetamide (1.452 g, 4.998 mmol) in anhydrous dichloromethane (60 ml) were added carbon tetrabromide (2.001 g, 6.035 mmol) and triphenylphosphine (1.571 g, 5.989 mmol) and the mixture was stirred at room temperature for 3 hr. The reaction mixture was concentrated under reduced pressure and the residue was purified by silica gel column chromatography (BW-300SP 10 g, ethyl acetate:hexane=2:3→1:1) to give N-(4-{2-[4-(2-bromoethyl)phenyl]ethyl}-1,3-thiazol-2-yl)acetamide (1.553 g, 4.396 mmol, yield 88.0%) as a white solid.

Step 2

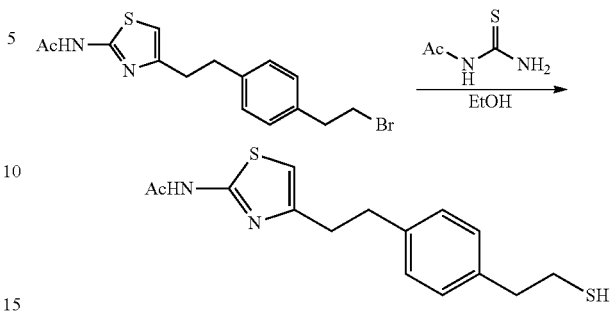

To a suspension of N-(4-{2-[4-(2-bromoethyl)phenyl]ethyl}-1,3-thiazol-2-yl)acetamide (353.3 mg, 1.000 mmol) in ethanol (4 ml) was added 1-acetyl-2-thiourea (177.4 mg, 1.501 mmol), and the mixture was heated under reflux for 7 hr. 1-Acetyl-2-thiourea (176.6 mg, 1.495 mmol) was added, and the mixture was heated under reflux for 17 hr. The mixture was cooled to room temperature, ethyl acetate (10 ml) was added, and the precipitated solid was filtered off. The filtrate was concentrated under reduced pressure, and purified twice by silica gel column chromatography (FUJI SILYSIA CHEMICAL LTD. DM-2035 21 g, ethyl acetate:hexane=2:3→1:1) to give N-(4-{2-[4-(2-sulfanylethyl)phenyl]ethyl}-1,3-thiazol-2-yl)acetamide (210.4 mg, 0.687 mmol, 68.7%) as a white solid.

Step 3

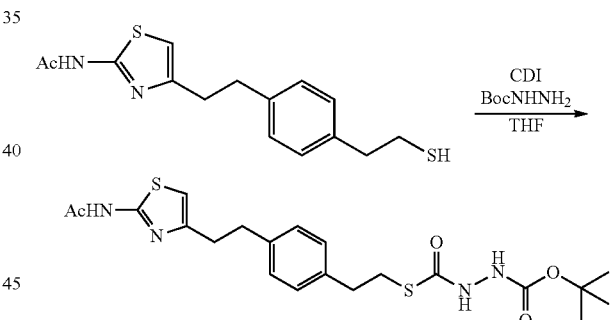

To a solution of N-(4-{2-[4-(2-sulfanylethyl)phenyl]ethyl}-1,3-thiazol-2-yl)acetamide (368.0 mg, 1.201 mmol) in anhydrous tetrahydrofuran (30 ml) was added 1,1'-carbonyldiimidazole (291.4 mg, 1.797 mmol), and the mixture was stirred at room temperature for 1 hr. tert-Butyl carbazate (477.9 mg, 3.616 mmol), anhydrous tetrahydrofuran (2 ml) was added, and the mixture was stirred at room temperature for 19 hr. Water (20 ml), 1M hydrochloric acid (10 ml) and ethyl acetate (30 ml) were added, and the mixture was stirred, stood still and partitioned. The organic layer was washed with saturated brine, dried over anhydrous magnesium sulfate, and concentrated under reduced pressure. The residue was purified by silica gel column chromatography (FUJI SILYSIA CHEMICAL LTD. BW-300SP 30 g, ethyl acetate:hexane=1:1) to give tert-butyl 2-({[2-(4-{2-[2-(acetylamino)-1,3-thiazol-4-yl]ethyl}phenyl)ethyl]sulfanyl}carbonyl)hydrazinecarboxylate (469.9 mg, 1.011 mmol, yield 84.2%) as a white solid.

Step 4

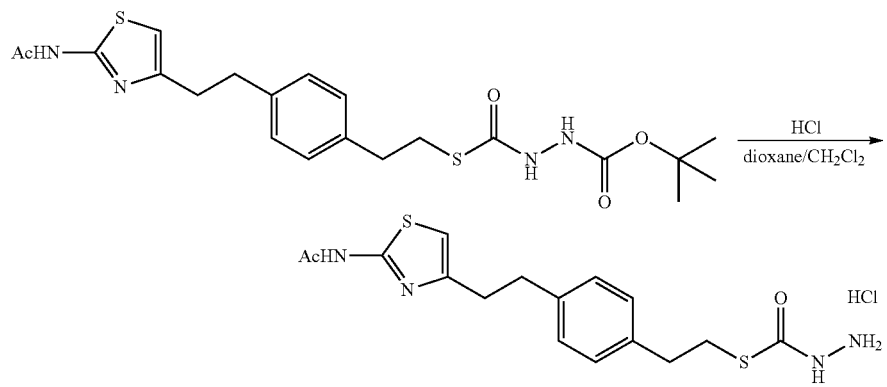

tert-Butyl 2-({[2-(4-{2-[2-(acetylamino)-1,3-thiazol-4-yl]ethyl}phenyl)ethyl]sulfanyl}carbonyl)hydrazinecarboxylate (449.3 mg, 0.967 mmol) was deprotected by a method similar to that of Production Example 33, step 4, to give the title compound (308.0 mg, 0.769 mmol, yield 79.5%) as a white solid.

melting point 146-149° C.

$^1$H-NMR (400 MHz, DMSO-d6): δ (ppm):12.05(1H, brs), 11.22(1H, brs), 11.0-9.8(3H, br), 7.13(4H, s), 6.72(1H, s), 3.10(2H, t, J=7.5 Hz), 2.92-2.78(6H, m), 2.11(3H, s)

$^{13}$C-NMR (100 MHz, DMSO-d6): δ (ppm):168.1, 167.5, 157.4, 150.1, 139.4, 137.1, 128.3, 128.2, 107.2, 35.2, 34.1, 32.6, 30.1, 22.4

MS(ESI+):365.1057[M(free)+H]$^+$, 387.0875[M(free)+Na]$^+$

Production Example 36

S-[(5-{2-[2-(acetylamino)-1,3-thiazol-4-yl]ethyl}thiophen-2-yl)methyl]hydrazinecarbothioate hydrochloride Step 1

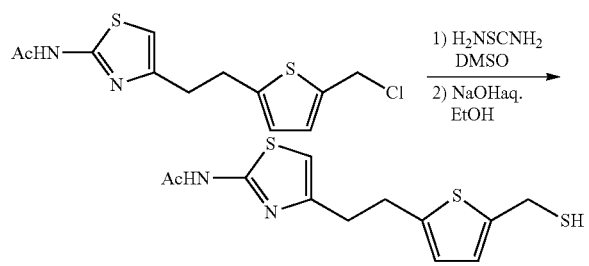

To a suspension of N-(4-{2-[5-(chloromethyl)thiophen-2-yl]ethyl}-1,3-thiazol-2-yl)acetamide in anhydrous dimethyl sulfoxide (1.5 ml) was added thiourea (479.9 mg, 6.304 mmol), and the mixture was stirred at room temperature for 21 hr. Ethyl acetate (200 ml) was added to the reaction mixture and placed in an ultrasonic bath at 20-40° C. for 1 hr. After stirring at room temperature for 45 min, the precipitate was collected by filtration, washed 5 times with ethyl acetate and dried under reduced pressure to give yellowish white solid (1.489 g). The solid was dissolved in a mixed solvent of ethanol (150 ml) and water (30 ml), and cooled to 0° C. Ice-cooled 8M aqueous sodium hydroxide (30 ml, 240 mmol) was added and stirred at 0° C. for 30 min. To acidify the reaction mixture, ice-cooled 1M hydrochloric acid (600 ml, 600 mmol) was added. After stirring at 0° C. for 30 min, the mixture was concentrated to about 350 ml. The mixture was extracted 5 times with ethyl acetate, and the combined organic layer was washed with saturated brine, dried over anhydrous magnesium sulfate, and concentrated under reduced pressure. The residue was purified by silica gel column chromatography (FUJI SILYSIA CHEMICAL LTD. BW-300SP 120 g, ethyl acetate:hexane=1:1) to give N-(4-{2-[5-(sulfanylmethyl)thiophen-2-yl]ethyl}-1,3-thiazol-2-yl)acetamide (493.3 mg, 1.653 mmol, yield 52.4%) as a white solid.

Step 2

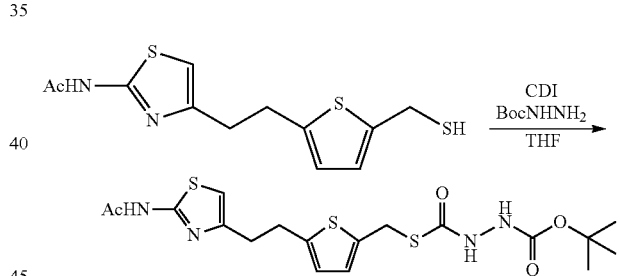

To a solution of 1,1'-carbonyldiimidazole (326.0 mg, 2.010 mmol) in anhydrous tetrahydrofuran (8 ml), a solution of N-(4-{2-[5-(sulfanylmethyl)thiophen-2-yl]ethyl}-1,3-thiazol-2-yl)acetamide (400.0 mg, 1.340 mmol) in anhydrous tetrahydrofuran (10 ml) was added dropwise at 0° C. The mixture was stirred at 0° C. for 15 min and at room temperature for 1 hr. tert-Butyl carbazate (351.4 mg, 4.021 mmol) was added, and the mixture was stirred at room temperature for 16 hr. The mixture was concentrated, and residue was added water (40 ml) and extracted 3 times with ethyl acetate. The combined organic layer was washed with ice-cooled 1M hydrochloric acid, saturated aqueous sodium hydrogen carbonate and saturated brine, dried over anhydrous magnesium sulfate and concentrated under reduced pressure. The residue was purified by silica gel column chromatography (FUJI SILYSIA CHEMICAL LTD. BW-300SP 100 g, ethyl acetate:hexane=1:1) to give tert-butyl 2-({[(5-{2-[2-(acetylamino)-1,3-thiazol-4-yl]ethyl}thiophen-2-yl)methyl]sulfanyl}carbonyl)hydrazinecarboxylate (316.7 mg, 0.694 mmol, yield 51.8%) as a white solid.

Step 3

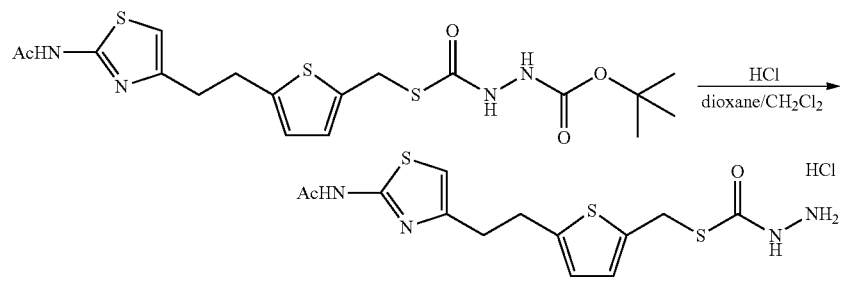

Tert-Butyl 2-({[(5-{2-[2-(acetylamino)-1,3-thiazol-4-yl]ethyl}thiophen-2-yl)methyl]sulfanyl}carbonyl)hydrazinecarboxylate (315.0 mg, 0.690 mmol) was deprotected by a method similar to that of Production Example 1, step 4, to give the title compound (222.8 mg, 0.567 mmol, yield 82.2%) as a slightly yellow-white solid.

melting point 147-153° C.

$^1$H-NMR (400 MHz, DMSO-d6): δ (ppm): 12.07(1H, brs), 11.36(1H, brs), 11.0-9.8(3H, br), 6.80(1H, d, J=3.3 Hz), 6.77(1H, s), 6.63(1H, d, J=3.3 Hz), 4.31(2H, s), 3.07(2H, t, J=7.6 Hz), 2.87(2H, t, J=7.6 Hz), 2.11(3H, s)

$^{13}$C-NMR (100 MHz, DMSO-d6): δ (ppm): 168.5, 167.1, 157.1, 149.7, 144.1, 138.4, 126.8, 124.4, 108.0, 33.0, 29.1, 28.0, 22.7

MS(ESI+):357.0485[M(free)+H]$^+$

Experimental Example 1

Enzyme Activity Inhibitory Effect on Human and Rat VAP-1 Enzyme (SSAO)

The compounds of the present invention obtained in Production Examples were examined for the enzyme activity inhibitory effect on human and rat VAP-1 enzyme (SSAO) by the following method.

The VAP-1 enzyme (SSAO) activity in both human and rat was measured by a radiochemical-enzyme assay using $^{14}$C-benzylamine as an artificial substrate. Human or rat VAP-1 was cloned from the cDNA library and expressed in a cell. The cell extract was preincubated with a test compound solution (final concentration $1\times10^{-7}$-$1\times10^{-11}$ mol/l) at room temperature for 20 minutes. Then, $^{14}$C-benzylamine (final concentration $1\times10^{-5}$ mol/l) was added, and the mixture was incubated at a final volume of 200 μl at 37° C. for 2 hours. The enzyme reaction was stopped by addition of 2 mol/l (200 μl) citric acid. The oxidation product was extracted with 1 ml toluene/ethyl acetate (1:1), and the radioactivity thereof was measured by a liquid scintillation counter. The results are shown in Table 1.

As shown in Table 1, the compound of the present invention markedly inhibited the enzyme activity of human and rat SSAO.

TABLE 1

| Enzyme activity inhibitory effect on human and rat VAP-1 enzyme (SSAO) | | | |
|---|---|---|---|
| Production Example | Chemical structure | IC$_{50}$ (nM) human | rat |
| 1 | 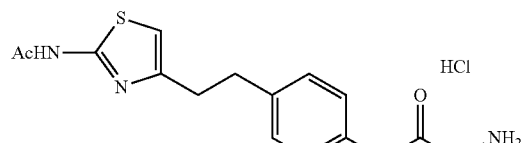 | 2.5 | 0.2 |
| 2 | 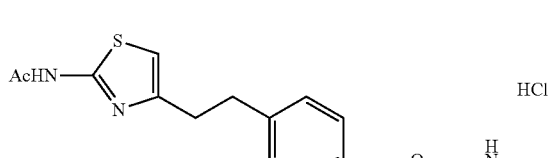 | 0.9 | 0.7 |

TABLE 1-continued

Enzyme activity inhibitory effect on human and rat VAP-1 enzyme (SSAO)

| Production Example | Chemical structure | IC$_{50}$ (nM) human | rat |
|---|---|---|---|
| 3 | AcHN-thiazole-CH₂CH₂-C₆H₄-CH₂CH₂-O-C(=O)-NH-NH₂ · HCl | 11.7 | 2.3 |
| 4 | AcHN-thiazole-CH₂CH₂-C₆H₃(F)-CH₂-O-C(=O)-NH-NH₂ · HCl | 0.8 | 0.4 |
| 5 | AcHN-thiazole-CH₂CH₂-C₆H₃(F)-CH₂-O-C(=O)-NH-NH₂ · HCl | 1.2 | 1.1 |
| 6 | AcHN-thiazole-CH₂CH₂-C₆H₂(F)(F)-CH₂-O-C(=O)-NH-NH₂ · HCl | 1.3 | 0.6 |
| 7 | AcHN-thiazole-CH₂-O-C₆H₄-CH₂CH₂-O-C(=O)-NH-NH₂ | 57.0 | 7.1 |
| 8 | AcHN-thiazole-C(=O)-O-C₆H₄-CH₂CH₂-O-C(=O)-NH-NH₂ · HCl | 6.4 | 1.7 |
| 9 | AcHN-thiazole-C(=O)-NH-C₆H₄-CH₂CH₂-O-C(=O)-NH-NH₂ · HCl | 17.1 | 1.0 |

TABLE 1-continued

Enzyme activity inhibitory effect on human and rat VAP-1 enzyme (SSAO)

| Production Example | Chemical structure | IC$_{50}$ (nM) human | rat |
|---|---|---|---|
| 11 | 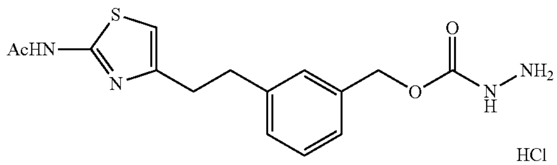 [SMILES: CC(=O)Nc1nc(CCc2cccc(COC(=O)NN)c2)cs1 ; Cl] | 1.3 | 0.2 |
| 12 | 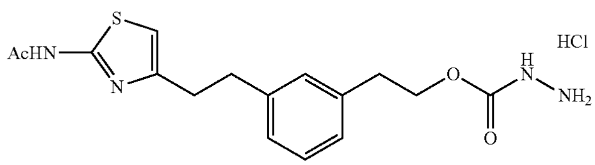 [SMILES: CC(=O)Nc1nc(CCc2cccc(CCOC(=O)NN)c2)cs1 ; Cl] | 3.2 | 0.5 |
| 13 | 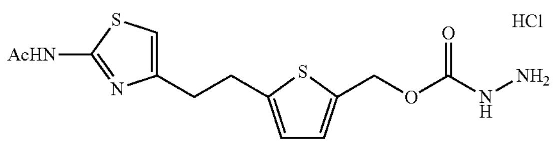 [SMILES: CC(=O)Nc1nc(CCc2ccc(COC(=O)NN)s2)cs1 ; Cl] | 3.4 | 0.7 |
| 14 | 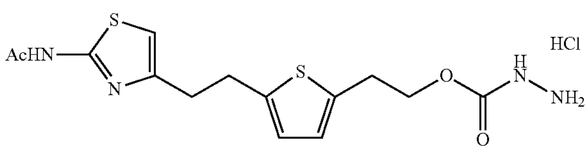 [SMILES: CC(=O)Nc1nc(CCc2ccc(CCOC(=O)NN)s2)cs1 ; Cl] | 5.1 | 5.3 |
| 15 | 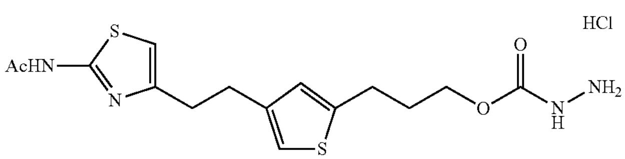 [SMILES: Cl ; CC(=O)Nc1nc(CCc2csc(CCCOC(=O)NN)c2)cs1] | 13.4 | 0.6 |
| 16 | 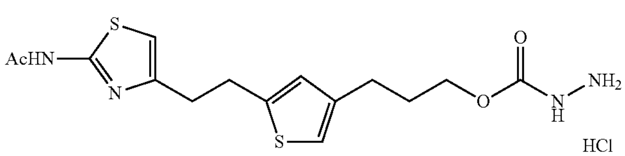 [SMILES: CC(=O)Nc1nc(CCc2cc(CCCOC(=O)NN)cs2)cs1 ; Cl] | 16.7 | 10.5 |
| 17 | 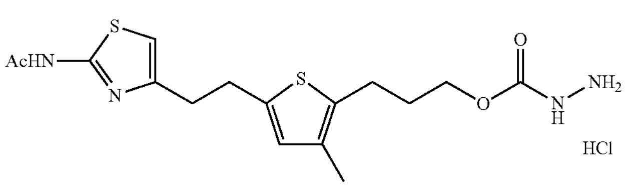 [SMILES: CC(=O)Nc1nc(CCc2cc(C)c(CCCOC(=O)NN)s2)cs1 ; Cl] | 68.7 | 5.0 |
| 18 | 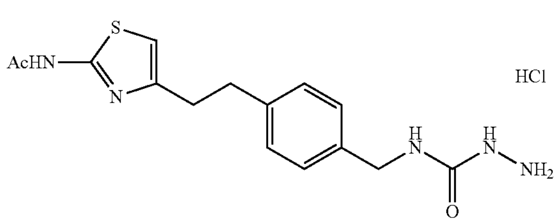 [SMILES: CC(=O)Nc1nc(CCc2ccc(CNC(=O)NN)cc2)cs1 ; Cl] | 4.0 | 1.3 |

TABLE 1-continued
Enzyme activity inhibitory effect on human and rat VAP-1 enzyme (SSAO)
| Production Example | Chemical structure | IC$_{50}$ (nM) human | rat |
|---|---|---|---|
| 19 | 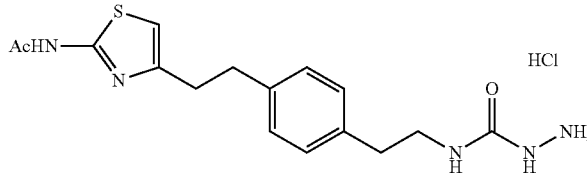 | 12.2 | 2.3 |
| 20 | 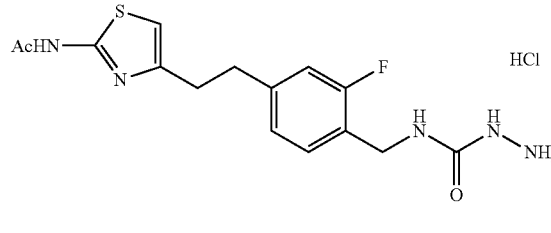 | 2.8 | 1.6 |
| 22 | 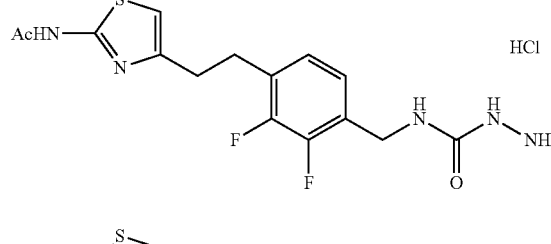 | 5.5 | 2.2 |
| 23 | 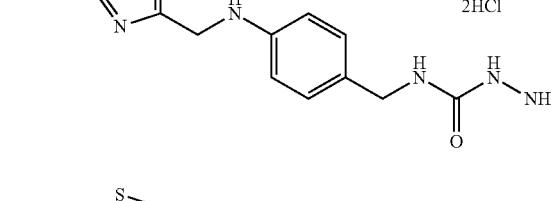 | 16.8 | 8.4 |
| 24 | 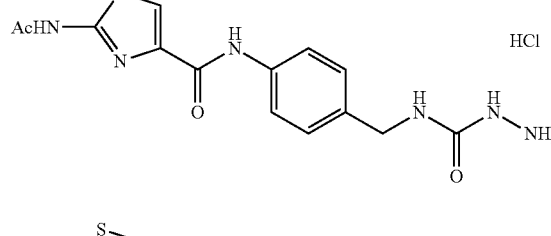 | 7.3 | 1.0 |
| 25 | 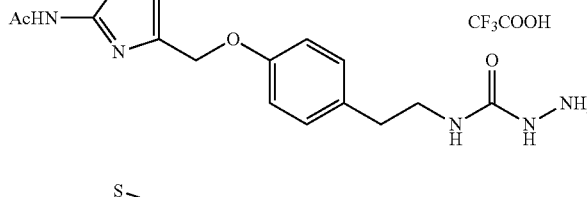 | 48.5 | 1.5 |
| 26 | 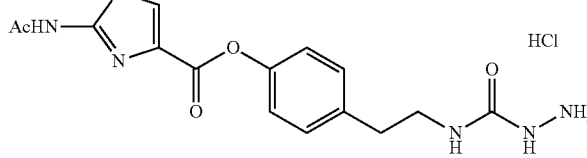 | 13.3 | 3.3 |

TABLE 1-continued
Enzyme activity inhibitory effect on human and rat VAP-1 enzyme (SSAO)
| Production Example | Chemical structure | IC$_{50}$ (nM) human | rat |
|---|---|---|---|
| 27 | 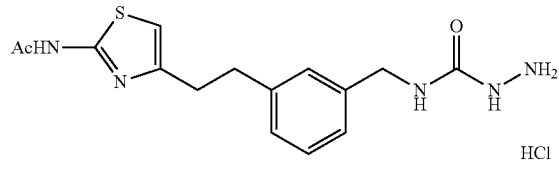 [SMILES: CC(=O)Nc1nc(CCc2cccc(CNC(=O)NN)c2)cs1 ; Cl] | 2.1 | 0.6 |
| 28 | 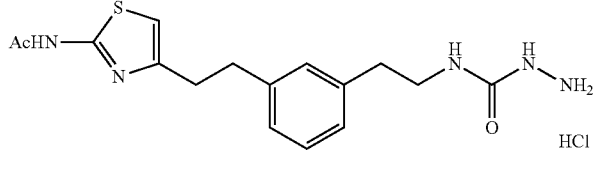 [SMILES: CC(=O)Nc1nc(CCc2cccc(CCNC(=O)NN)c2)cs1 ; Cl] | 44.3 | 5.6 |
| 29 | 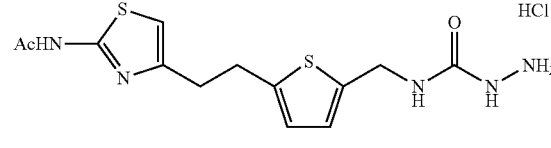 | 1.8 | 0.6 |
| 30 | 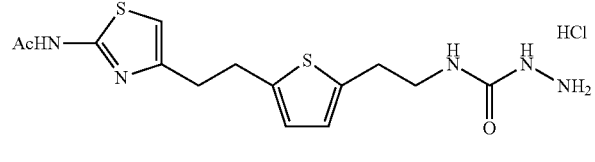 [SMILES: CC(=O)Nc1nc(CCc2ccc(CCNC(=O)NN)s2)cs1 ; Cl] | 18.8 | 3.8 |
| 33 | 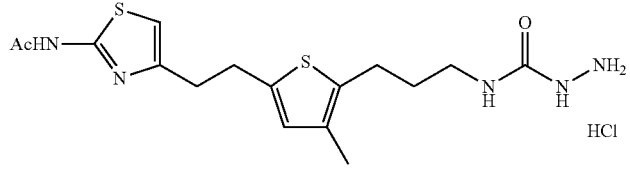 [SMILES: CC(=O)Nc1nc(CCc2cc(C)c(CCCNC(=O)NN)s2)cs1 ; Cl] | 108 | 2.1 |
| 34 | 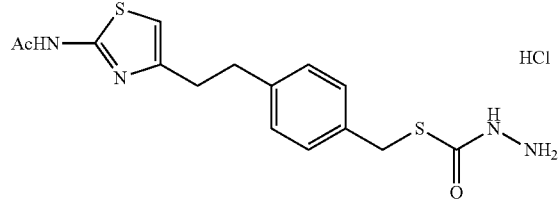 [SMILES: CC(=O)Nc1nc(CCc2ccc(CSC(=O)NN)cc2)cs1 ; Cl] | 23.2 | 4.6 |
| 36 | 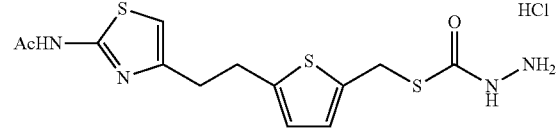 [SMILES: CC(=O)Nc1nc(CCc2ccc(CSC(=O)NN)s2)cs1 ; Cl] | 2.3 | 0.6 |

Experimental Example 2

Enzyme Activity Inhibitory Effect on Human Monoamine Oxidase Enzymes (MAO-A and MAO-B)

The compounds of the present invention obtained in Production Examples were examined for the enzyme activity inhibitory effect on human monoamine oxidase enzymes (MAO-A and MAO-B) by the following method.

Recombinant human MAO-A and MAO-B enzymes were purchased from Sigma Ltd. Human MAO-A and MAO-B activities were measured using MAO Detection Kit (Fluoro MAO, Cell Technology Inc.). The assay was performed using a 96-well plate. 1× Reaction buffer (40 μl) was added to each well, and 50 μl of MAO-A or MAO-B was further added. Then, a test compound solution (10 μl, final concentration $1\times10^{-5}$-$1\times10^{-10}$ mol/l) was added, and the mixture was incubated at 37° C. for 20 minutes. The reaction cocktail (100 μl) was added, and the mixture was incubated at a final volume of 200 μl at 37° C. for 2 hours. Then, the fluorescence at 590 nm was detected by a multispectro microplate reader (Varioskan, Thermo Fisher Scientific K.K.) using an excitation light at 570 nm. The results are shown in Table 2.

As shown in Table 2, the compound of the present invention did not show a marked inhibitory action on human MAO-A or MAO-B. Since the compound does not substantially show an inhibitory action on other monoamine oxidases, it is clear that the compound of the present invention shows a selective and specific inhibitory action on SSAO.

TABLE 2

Enzyme activity inhibitory effect on human monoamine oxidase enzymes (MAO-A and MAO-B)

| Compound | Chemical structure | MAO-A inhibition $IC_{50}$ (μM) | MAO-B inhibition $IC_{50}$ (μM) |
|---|---|---|---|
| Production Example 1 | AcHN-thiazole-CH₂CH₂-phenyl-O-C(O)-NH-NH₂ · HCl | >100 | >100 |
| Production Example 2 | AcHN-thiazole-CH₂CH₂-phenyl-CH₂-O-C(O)-NH-NH₂ · HCl | >100 | >100 |
| Production Example 18 | AcHN-thiazole-CH₂CH₂-phenyl-CH₂-NH-C(O)-NH-NH₂ · HCl | >100 | >100 |
| Clorgyline | (structure shown) | 0.0011 | No Data |
| Pargyline | (structure shown) | No data | 0.103 |

Industrial Applicability

The present invention provides a compound represented by the formula (I)

$$R^1\text{—NH—X—Y—Z} \qquad (I)$$

wherein each symbol is as defined above, useful as a VAP-1 inhibitor, or a pharmaceutically acceptable salt thereof, a pharmaceutical composition, a pharmaceutical agent for the prophylaxis or treatment of VAP-1 associated diseases such as macular edema, vascular hyperpermeable disease, ophthalmic diseases associated with hypoxia or ischemia and cataract and the like, and the like.

This application is based on a patent application No. 2008-021588 filed in Japan, the contents of which are incorporated in full herein by this reference.

The invention claimed is:
1. A compound represented by the formula (I):

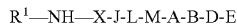

wherein
R¹ is acyl;
X is a divalent optionally substituted thiazole;
J is a bond, lower alkylene, lower alkenylene, lower alkynylene, or —(CH$_2$)$_n$—CO—, where n is 0;
L is a bond, —O—, —NH—, —CO— or —SO$_2$—;
M is a bond, lower alkylene, lower alkenylene or lower alkynylene,
A is a divalent optionally substituted benzene, or a divalent optionally substituted thiophene;
B is —(CH$_2$)$_l$—NR²—CO— wherein R² is hydrogen, lower alkyl or acyl, and l is an integer of 1 to 6, —(CH$_2$)$_m$—O—CO— or —(CH$_2$)$_m$—S—CO— wherein m is an integer of 0 to 6;
D is —NR³— wherein R³ is hydrogen, lower alkyl, alkoxycarbonyl or acyl; and
E is optionally substituted amino; or a pharmaceutically acceptable salt thereof.

2. The compound of claim 1, wherein the compound is
4-{2-[2-(acetylamino)-1,3-thiazol-4-yl]ethyl}phenyl hydrazinecarboxylate,
4-{2-[2-(acetylamino)-1,3-thiazol-4-yl]ethyl}benzyl hydrazinecarboxylate,
2-(4-{2-[2-(acetylamino)-1,3-thiazol-4-yl]ethyl}phenyl) ethyl hydrazinecarboxylate,
4-{2-[2-(acetylamino)-1,3-thiazol-4-yl]ethyl}-2-fluorobenzyl hydrazinecarboxylate,
4-{2-[2-(acetylamino)-1,3-thiazol-4-yl]ethyl}-3-fluorobenzyl hydrazinecarboxylate,
4-{2-[2-(acetylamino)-1,3-thiazol-4-yl]ethyl}-2,3-difluorobenzyl hydrazinecarboxylate,
2-(4-{[2-(acetylamino)-1,3-thiazol-4-yl]methoxy}phenyl)ethyl hydrazinecarboxylate,
4-{2-[(hydrazinocarbonyl)oxy]ethyl}phenyl 2-(acetylamino)-1,3-thiazole-4-carboxylate,
2-[4-({[2-(acetylamino)-1,3-thiazol-4-yl]carbonyl}amino)phenyl]ethyl hydrazinecarboxylate,
3-{2-[2-(acetylamino)-1,3-thiazol-4-yl]ethyl}phenyl hydrazinecarboxylate,
3-{2-[2-(acetylamino)-1,3-thiazol-4-yl]ethyl}benzyl hydrazinecarboxylate,
2-(3-{2-[2-(acetylamino)-1,3-thiazol-4-yl]ethyl}phenyl) ethyl hydrazinecarboxylate,
{5-[2-(2-acetylamino-1,3-thiazol-4-yl)ethyl]thiophen-2-yl}methyl hydrazinecarboxylate,
2-(5-{2-[2-(acetylamino)-1,3-thiazol-4-yl]ethyl}thiophen-2-yl)ethyl hydrazinecarboxylate,
3-(4-{2-[2-(acetylamino)-1,3-thiazol-4-yl]ethyl}thiophen-2-yl)propyl hydrazinecarboxylate,
3-(5-{2-[2-(acetylamino)-1,3-thiazol-4-yl]ethyl}thiophen-3-yl)propyl hydrazinecarboxylate,
3-(5-{2-[2-(acetylamino)-1,3-thiazol-4-yl]ethyl}-3-methylthiophen-2-yl)propyl hydrazinecarboxylate,
N-(4-{2-[2-(acetylamino)-1,3-thiazol-4-yl]ethyl}benzyl) hydrazinecarboxamide,
N-[2-(4-{2-[2-(acetylamino)-1,3-thiazol-4-yl]ethyl}phenyl)ethyl]hydrazinecarboxamide,
N-(4-{2-[2-(acetylamino)-1,3-thiazol-4-yl]ethyl}-2-fluorobenzyl)hydrazinecarboxamide,
N-(4-{2-[2-(acetylamino)-1,3-thiazol-4-yl]ethyl}-3-fluorobenzyl)hydrazinecarboxamide,
N-(4-{2-[2-(acetylamino)-1,3-thiazol-4-yl]ethyl}-2,3-difluorobenzyl)hydrazinecarboxamide,
N-[4-({[2-(acetylamino)-1,3-thiazol-4-yl]methyl}amino) benzyl]hydrazinecarboxamide,
2-(acetylamino)-N-(4-{[(hydrazinocarbonyl)amino] methyl}phenyl)-1,3-thiazole-4-carboxamide,
N-[2-(4-{[2-(acetylamino)-1,3-thiazol-4-yl] methoxy}phenyl)ethyl]hydrazinecarboxamide,
4-{2-[(hydrazinocarbonyl)amino]ethyl}phenyl 2-(acetylamino)-1,3-thiazole-4-carboxylate,
N-(3-{2-[2-(acetylamino)-1,3-thiazol-4-yl]ethyl}benzyl) hydrazinecarboxamide,
N-[2-(3-{2-[2-(acetylamino)-1,3-thiazol-4-yl] ethyl}phenyl)ethyl]hydrazinecarboxamide,
N-[2-(5-{2-[2-(acetylamino)-1,3-thiazol-4-yl] ethyl}thiophen-2-yl)methyl]hydrazinecarboxamide,
N-[2-(5-{2-[2-(acetylamino)-1,3-thiazol-4-yl] ethyl}thiophen-2-yl)ethyl]hydrazinecarboxamide,
N-[3-(4-{2-[2-(acetylamino)-1,3-thiazol-4-yl] ethyl}thiophen-2-yl)propyl]hydrazinecarboxamide,
N-[3-(5-{2-[2-(acetylamino)-1,3-thiazol-4-yl] ethyl}thiophen-3-yl)propyl]hydrazinecarboxamide,
N-[3-(5-{2-[2-(acetylamino)-1,3-thiazol-4-yl]ethyl}-3-methylthiophen-2-yl)propyl]hydrazinecarboxamide,
S-(4-{2-[2-(acetylamino)-1,3-thiazol-4-yl]ethyl}benzyl) hydrazinecarbothioate,
S-[2-(4-{2-[2-(acetylamino)-1,3-thiazol-4-yl] ethyl}phenyl)ethyl]hydrazinecarbothioate, or
S-[(5-{2-[2-(acetylamino)-1,3-thiazol-4-yl] ethyl}thiophen-2-yl)methyl]hydrazinecarbothioate, or a pharmaceutically acceptable salt thereof.

3. The compound of claim 1, wherein the compound is 4-{2-[2-(acetylamino)-1,3-thiazol-4-yl]ethyl}phenyl hydrazinecarboxylate, 4-{2-[2-(acetylamino)-1,3-thiazol-4-yl] ethyl}benzyl hydrazinecarboxylate or N-(4-{2-[2-(acetylamino)-1,3-thiazol-4-yl]ethyl}benzyl) hydrazinecarboxamide, or a pharmaceutically acceptable salt thereof.

4. A VAP-1 inhibitor comprising the compound of claim 1 or a pharmaceutically acceptable salt thereof as an active ingredient.

5. A method for the treatment of VAP-1 associated disease in a subject, which method comprises administering an effective amount of the compound of claim 1 or a pharmaceutically acceptable salt thereof to a subject in need thereof, wherein VAP-1 in the subject is inhibited, thereby treating a VAP-1 associated disease in the subject,
wherein the VAP-1 associated disease is macular edema, aged macular degeneration, aged disciform macular degeneration, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, ocular inflammatory disease or a symptom thereof, erythema, erythema exsudativum multiforme, erythema nodosum, erythema annulare, scleredema, dermatitis, angioneurotic edema, laryngeal edema, glottic edema, subglottic laryngitis, bronchitis, rhinitis, pharyngitis, sinusitis, otitis media, cirrhosis, essential stabilized hypertension, diabetes, arteriosclerosis, endothelial injury relating to diabetes, arteriosclerosis and hypertension, cardiovascular disease relating to diabetes or uremia, pain relating to gout and arthritis, inflammatory disease of connective tissue or symptom thereof, inflammatory disease of gastrointestinal tract or a symptom thereof, inflammatory disease of central nervous system or a symptom thereof, pulmonary inflammatory disease or a symptom thereof, disease relating to carbohydrate metabolism, disease relating to abnormality in the differentiation or function of adipocyte or function of smooth muscle cell, vascular disease, chronic arthritis, inflammatory bowel disease, SSAO-mediated complications, ophthalmic disease associated with hypoxia or ischemia, or cataract.

6. A method for the treatment of VAP-1 associated disease in a subject, which method comprises administering an effective amount of the compound of claim 2 or a pharmaceutically acceptable salt thereof to a subject in need thereof, wherein VAP-1 in the subject is inhibited, thereby treating a VAP-1 associated disease in the subject, wherein the VAP-1 associated disease is macular edema, aged macular degeneration, aged disciform macular degeneration, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, ocular inflammatory disease or a symptom thereof, erythema, erythema exsudativum multiforme, erythema nodosum, erythema annulare, scleredema, dermatitis, angioneurotic edema, laryngeal edema, glottic edema, subglottic laryngitis, bronchitis, rhinitis, pharyngitis, sinusitis, otitis media, cirrhosis, essential stabilized hypertension, diabetes, arteriosclerosis, endothelial injury relating to diabetes, arteriosclerosis and hypertension, cardiovascular disease relating to diabetes or uremia, pain relating to gout and arthritis, inflammatory disease of connective tissue or symptom thereof, inflammatory disease of gastrointestinal tract or a symptom thereof, inflammatory disease of central nervous system or a symptom thereof, pulmonary inflammatory disease or a symptom thereof, disease relating to carbohydrate metabolism, disease relating to abnormality in the differentiation or function of adipocyte or function of smooth muscle cell, vascular disease, chronic arthritis, inflammatory bowel disease, SSAO-mediated complications, ophthalmic disease associated with hypoxia or ischemia, or cataract.

7. A method for the treatment of VAP-1 associated disease in a subject, which method comprises administering an effective amount of the compound of claim 3 or a pharmaceutically acceptable salt thereof to a subject in need thereof, wherein VAP-1 in the subject is inhibited, thereby treating a VAP-1 associated disease in the subject, wherein the VAP-1 associated disease is macular edema, aged macular degeneration, aged disciform macular degeneration, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, ocular inflammatory disease or a symptom thereof, erythema, erythema exsudativum multiforme, erythema nodosum, erythema annulare, scleredema, dermatitis, angioneurotic edema, laryngeal edema, glottic edema, subglottic laryngitis, bronchitis, rhinitis, pharyngitis, sinusitis, otitis media, cirrhosis, essential stabilized hypertension, diabetes, arteriosclerosis, endothelial injury relating to diabetes, arteriosclerosis and hypertension, cardiovascular disease relating to diabetes or uremia, pain relating to gout and arthritis, inflammatory disease of connective tissue or symptom thereof, inflammatory disease of gastrointestinal tract or a symptom thereof, inflammatory disease of central nervous system or a symptom thereof, pulmonary inflammatory disease or a symptom thereof, disease relating to carbohydrate metabolism, disease relating to abnormality in the differentiation or function of adipocyte or function of smooth muscle cell, vascular disease, chronic arthritis, inflammatory bowel disease, SSAO-mediated complications, ophthalmic disease associated with hypoxia or ischemia, or cataract.

8. A pharmaceutical composition comprising (a) the compound of claim 1 or a pharmaceutically acceptable salt thereof and (b) a pharmaceutically acceptable carrier.

9. A pharmaceutical composition comprising (a) the compound of claim 2 or a pharmaceutically acceptable salt thereof and (b) a pharmaceutically acceptable carrier.

10. A pharmaceutical composition comprising (a) the compound of claim 3 or a pharmaceutically acceptable salt thereof and (b) a pharmaceutically acceptable carrier.

11. The compound of claim 1, wherein A is a divalent optionally substituted benzene; and B is —$(CH_2)_m$—O—CO—wherein m is an interger of 0 to 6 ; or a pharmaceutically acceptable salt thereof.

12. The compound of claim 11 wherein L is a bond; or a pharmaceutically acceptable salt therof.

13. The method of claim 5, wherein the VAP-1 associated disease is macular edema, and the macular edema is diabetic macular edema, nondiabetic macular edema, or crystiod macular edema.

14. The method of claim 5, wherein the VAP-1 associated disease is ocular inflammatory disease or a symptom thereof, wherein the ocular inflammatory disease is caused by physical injury to the eye, bacterial infection, viral infection, or ophthalmic operation, and wherein the symptom of the ocular inflammatory disease is itching, flare, edema, or ulcer.

15. The method of claim 5, wherein the VAP-1 associated disease is dermatitis, and the dermatitis is psoriasis, allergic lesion, lichen planus, pityriasis rosea, contact dermatitis, atopic dermatitis, or pityriasis rubra pilaris.

16. The method of claim 5, wherein the VAP-1 associated disease is dermatitis, and the dermatitis is psoriasis or atopic dermatitis.

17. The method of claim 5, wherein the VAP-1 associated disease is inflammatory disease of connective tissue or a symptom thereof, and the inflammatory disease of connective tissue or symptom thereof is rheumatoid arthritis, ankylosing spondylitis, psoriatic arthritis, osteoarthritis, degenerative joint disease, Reiter's syndrome, Sjogren's syndrome, Behcet's syndrome, relapsing polychrondritis, systemic lupus erythmatosus, discoid lupus erythmatodes, systemic sclerosis, eosinophilic fasciitis, polymyosiitis, dermatomyositis, polymyalgia rheumatica, vasculitis, temporal arthritis, polyarteritis nodosa, Wegener's granulamatosis, mixed connective tissue diseases, or juvenile rheumatoid arthritis.

18. The method of claim 5, wherein the VAP-1 associated disease is inflammatory disease of gastrointestinal tract or a symptom thereof, and the inflammatory disease of the gastrointestinal tract or symptom thereof is Chrohn's disease, ulcerative colitis, irritable bowel syndrome, spastic colon, inflammatory bowel disease, fibrosis of the liver, inflammation of the oral mucous membrane, stomatitis, or recurrent aphthous stomatitis.

19. The method of claim 5, wherein the VAP-1 associated disease is inflammatory disease of gastrointestinal tract or sympyom thereof, and the inflammatory disease of gastrointestinal tract or symptom thereof is ulcerative colitis.

20. The method of claim 5, wherein the VAP-1 associated disease is inflammatory disease of central nervous system or a symptom thereof, and the inflammatory disease of central nervous system or symptom thereof is multiple sclerosis, Alzheimer's disease, or ischemia-reperfusion injury related to ischemic stroke.

21. The new method of claim 5, wherein the VAP-1 disease is pulmonary inflammatory disease or a symptom thereof, and the pulmonary inflammatory disease or symptom thereof is asthma, adult respiratory distress syndrome, or chronic obliterative pulmonary disease.

22. The method of claim 5, wherein the VAP-1 associated disease is disease relating to carbohydrate metabolism, and the disease relating carbohydrate metabolism is diabetes, complications derived from diabetes, diabetic neuropathy, diabetic nephropathy, disease of microvessel and large vessel, arterisclerosis, retinopathy, nephropathy, nephrotic syndrome, neuropathy, multiple neuropathy, mononeuropathy, autonomic neuropathy, foot ulcer, articular problem, or increase in infection risk.

23. The new method of claim 5, wherein the VAP-1 associated disease is disease relating to carbohydrate metabolism, and the disease relating to carbohydrate metabolism is diabetic neuropathy.

24. The new method of claim 5, wherein the VAP-1 associated disease is disease relating to abnormality in the differentiation or function of adipocyte or function of smooth muscle cell, and the disease relating to abnormality in the differentiation or function of adipocyte or function of smooth muscle cell is arteriosclerosis or obesity.

25. The method of claim 5, wherein the VAP-1 associated disease is vascular disease, and the vascular disease is artheromatous atherosclerosis, nonartheromatous atherosclerotic disease, ischemic cardiac diseases, myocardial infarction, peripheral arterial obstruction, Raynaud's disease, Raynaud's phenomenon, or thromboangiitis obliterans.

26. The method of claim 5, wherein the VAP-1 associated disease is SSAO-mediated complications, and the SSAO-mediated complications are diabetes, insulin-dependent diabetes, noninsulin-dependent diabetes, vascular complications, heart attack, angina pectoris, apoplexy, amputation, blindness, or renal failure.

27. The method of claim 5, wherein the VAP-1 associated disease is ophthalmic disease associated with hypoxia or ischemia, and the ophthalmic disease associated with hypoxia or ischemia is retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease, Eales disease, antiphospholipid antibody syndrome, leukemic retinopathy, blood hyperviscosity syndrome, macroglobulinemia, interferon-associated retinopathy, hypertensive retinopathy, radiation retinopathy, or corneal epithelial deficiency.

28. The new method of claim 6, wherein the VAP-1 associated disease is dermatitis, and the dermatitis is psoriasis, allergic lesion, lichen planus, pityriasis rosea, contact dermatitis, atopic dermatitis, or pityriasis rubra pilaris.

29. The method of claim 6, wherein the VAP-1 associated disease is dermatitis, and the dermatitis is psoriasis or atopic dermatitis.

30. The method of claim 6, wherein the VAP-1 associated disease is inflammatory disease of gastrointestinal tract or a symptom thereof, and the inflammatory disease of gastrointestinal tract or symptom thereof is ulcerative colitis.

31. The method of claim 6, wherein the VAP-1 associated disease is disease relating to carbohydrate metabolism, and the disease relating to carbohydrate metabolism is diabetic neuropathy.

32. The method of claim 7, wherein the VAP-1 associated disease is dermatitis, and the dermatitis is psoriasis, allergic lesion, lichen planus, pityriasis rosea, contact dermatitis, atopic dermatitis, or pityriasis rubra pilaris.

33. The method of claim 7, wherein the VAP-1 associated disease is dermatitis, and the dermatitis is psoriasis or atopic dermatitis.

34. The method of claim 7, wherein the VAP-1 associated disease is inflammatory disease of gastrointestinal tract or a symptom thereof, and the inflammatory disease of gastrointestinal tract or a symptom thereof is ulcerative colitis.

35. The method of claim 7, wherein the VAP-1 associated disease is disease relating to carbohydrate metabolism, and the disease relating to carbohydrate metabolism is diabetic neuropathy.

\* \* \* \* \*

UNITED STATES PATENT AND TRADEMARK OFFICE
CERTIFICATE OF CORRECTION

PATENT NO. : 8,507,690 B2
APPLICATION NO. : 12/864773
DATED : August 13, 2013
INVENTOR(S) : Matsukawa et al.

It is certified that error appears in the above-identified patent and that said Letters Patent is hereby corrected as shown below:

IN THE CLAIMS

Claim 17, column 130, line 62, "polychrondritis" should read "polychondritis"

Claim 17, column 130, line 63, "erythmatosus" should read "erythematosus"

Claim 17, column 130, line 63, "erythmatodes" should read "erythematodes"

Claim 17, column 130, line 64, "polymyosiitis" should read "polymyositis"

Claim 17, column 130, line 66, "granulamatosis" should read "granulomatosis"

Claim 18, column 131, line 4, "Chrohn's" should read "Crohn's"

Claim 19, column 131, line 11, "sympyon thereof" should read "symptom thereof"

Claim 20, column 131, line 17, "related" should read "relating"

Claim 21, column 131, line 19, "The new method" should read "The method"

Claim 21, column 131, line 19, "VAP-1 disease" should read "VAP-1 associated disease"

Claim 22, column 131, line 26, "relating carbohydrate" should read "relating to carbohydrate"

Claim 22, column 131, line 29, "arterisclerosis" should read "arteriosclerosis"

Claim 23, column 131, line 33, "The new method" should read "The method"

Claim 24, column 131, line 37, "The new method" should read "The method"

Signed and Sealed this
Twentieth Day of May, 2014

Michelle K. Lee
*Deputy Director of the United States Patent and Trademark Office*

CERTIFICATE OF CORRECTION (continued)
U.S. Pat. No. 8,507,690 B2

Claim 25, column 131, lines 45-46, "artherosclerotic" should read "atherosclerotic"

Claim 27, column 132, line 18, "epithelial deficiency" should read "epithelial stem cell deficiency"

Claim 28, column 132, line 19, "The new method" should read "The method"